(12) United States Patent
Zhu et al.

(10) Patent No.: US 8,969,049 B2
(45) Date of Patent: Mar. 3, 2015

(54) YARROWIA DIACYLGLYCEROL ACYLTRANSFERASE PROMOTER REGIONS FOR GENE EXPRESSION IN YEAST

(75) Inventors: Quinn Qun Zhu, West Chester, PA (US); Zhixiong Xue, Chadds Ford, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 273 days.

(21) Appl. No.: 13/435,246

(22) Filed: Mar. 30, 2012

(65) Prior Publication Data
US 2012/0252079 A1 Oct. 4, 2012

Related U.S. Application Data

(60) Provisional application No. 61/469,933, filed on Mar. 31, 2011.

(51) Int. Cl.

| | |
|---|---|
| C12P 21/06 | (2006.01) |
| C12P 7/64 | (2006.01) |
| C12N 1/20 | (2006.01) |
| C12N 15/00 | (2006.01) |
| C07H 21/04 | (2006.01) |
| C12N 15/81 | (2006.01) |
| C12N 9/10 | (2006.01) |

(52) U.S. Cl.
CPC ............ *C12N 15/815* (2013.01); *C12N 9/1029* (2013.01); *C12P 7/6427* (2013.01); *C12Y 203/0102* (2013.01); *C12P 7/6463* (2013.01); *C12P 7/6472* (2013.01)
USPC ....... 435/134; 435/69.1; 435/183; 435/252.3; 435/320.1; 536/23.2

(58) Field of Classification Search
None
See application file for complete search history.

(56) References Cited

U.S. PATENT DOCUMENTS 7,521,223 B2 4/2009 Yadav et al.

FOREIGN PATENT DOCUMENTS

| WO | 2005003310 A2 | 1/2005 |
|---|---|---|
| WO | 2005003322 A2 | 1/2005 |
| WO | 2006052754 A2 | 5/2006 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
International Search Report, International Patent Application PCT/US2012/031706, Mailed Aug. 7, 2012.
Database Accession No. AZT93124, *Yarrowia lipolytica* DGAT2M Promotor DNA, Seq:94, Apr. 26, 2012, Retrieved From EBI Accession No. GSN: AZT93124.
Database Accession No. FP690623, *Yarrowia lipolytica* 5-Prime EST From Close TQOAAC9YE14, Jun. 17, 2010, Retrieved From EBI Accession No. EM_EST:FP69023.
Database Accession No. FP688108, *Yarrowia lipolytica* 5-Prime EST From Close TQOAAB15Y024, Jun. 17, 2010, Retrieved From EBI Accession No. EM_EST:FP688108.
Madzak et al., Protein Expression and Secretion in the Non-Conventional Yeast *Yarrowia lipolytica*: A Review, Journal of Biotechnology, vol. 109 (2004), pp. 63-81.
Mekouar et al., Detection and Analysis of Alternative Splicing in *Yarrowia lipolytica* Reveal Structural Constraints Facilitating Nonsense-Mediated Decay of Intron-Retaining Transcripts, Genome Biology, vol. 11, No. 6 (2010), pp. 1-17.
Zhang et al., Three Diacylglycerol Acyltransferases Contribute to Oil Biosynthesis and Normal Growth in *Yarrowia lipolytica*, Yeast, vol. 29 (2012), pp. 25-38.

* cited by examiner

*Primary Examiner* — Christian Fronda

(57) ABSTRACT

Promoter regions associated with the *Yarrowia lipolytica* diacylglycerol acyltransferase 2 (dgat2) gene are disclosed and have been found to be particularly effective for the expression of heterologous genes in yeast. These promoter regions will be useful for driving high-level expression of genes involved in the production of omega-3 and omega-6 fatty acids.

11 Claims, 7 Drawing Sheets

FIG. 2C

Figure 1:
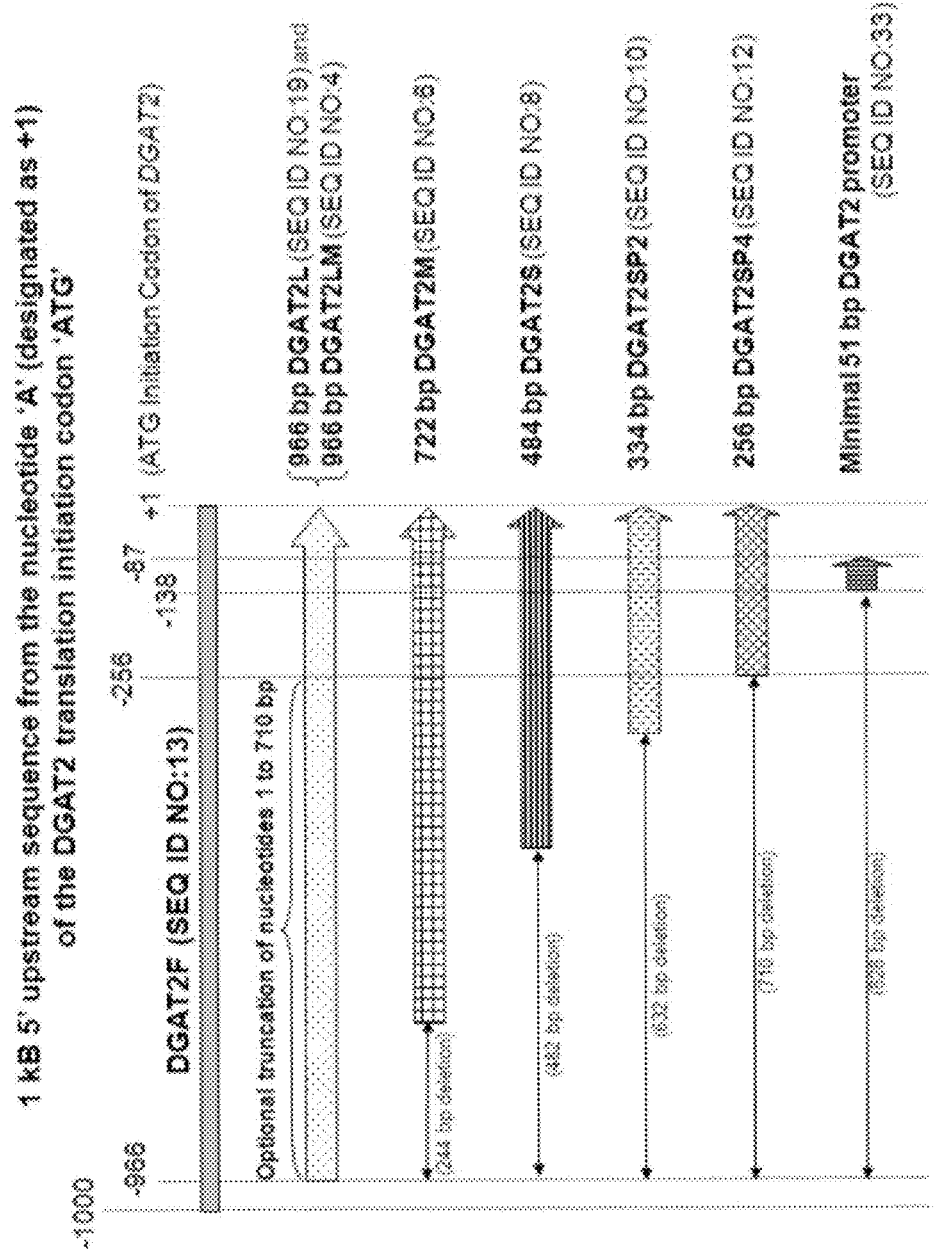

YARROWIA DIACYLGLYCEROL ACYLTRANSFERASE PROMOTER REGIONS FOR GENE EXPRESSION IN YEAST

This application claims the benefit of U.S. Provisional Application No. 61/469,933, filed Mar. 31, 2011, which is incorporated herein by reference in its entirety.

FIELD OF THE INVENTION

This invention is in the field of biotechnology. More specifically, this invention pertains to diacylglycerol acyltransferase ["DGAT"] promoter regions derived from *Yarrowia lipolytica* that are useful for gene expression in yeast.

BACKGROUND OF THE INVENTION

Oleaginous yeast are defined as those organisms that are naturally capable of oil synthesis and accumulation, wherein oil accumulation ranges from at least about 25% up to about 80% of the dry cell weight. The technology for growing oleaginous yeast with high oil content is well developed (for example, see EP 0 005 277B1; Ratledge, C., *Prog. Ind. Microbiol.*, 16:119-206 (1982)). And, these organisms have been commercially used for a variety of purposes in the past.

Recently, the natural abilities of oleaginous yeast have been enhanced by advances in genetic engineering, resulting in organisms capable of producing polyunsaturated fatty acids ["PUFAs"], carotenoids, resveratrol and sterols. For example, significant efforts by Applicants' Assignee have demonstrated that *Yarrowia lipolytica* can be engineered for production of omega-3 and omega-6 fatty acids, by introducing and expressing genes encoding the omega-3/omega-6 biosynthetic pathway (U.S. Pat. No. 7,238,482; U.S. Pat. No. 7,465,564; U.S. Pat. No. 7,550,286; U.S. Pat. No. 7,588,931; and U.S. Pat. No. 7,932,077; U.S. Pat. Appl. Publ. Nos. 2009-0093543-A1 and 2010-0317072-A1).

Recombinant production of any heterologous protein is generally accomplished by constructing an expression cassette in which the DNA coding for the protein of interest is placed under the control of a promoter suitable for the host cell. The expression cassette is then introduced into the host cell (i.e., usually by plasmid-mediated transformation or targeted integration into the host genome) and production of the heterologous protein is achieved by culturing the transformed host cell under conditions necessary for the proper function of the promoter contained within the expression cassette. Thus, the development of new host cells (e.g., transformed yeast) for recombinant production of proteins generally requires the availability of promoters that are suitable for controlling the expression of a protein of interest in the host cell.

A variety of strong promoters have been isolated from *Yarrowia lipolytica* that are useful for heterologous gene expression in yeast, as shown in the Table below.

TABLE 1

Characterized *Yarrowia lipolytica* Promoters

| Promoter Name | Native Gene | Reference |
|---|---|---|
| XPR2 | alkaline extracellular protease | U.S. Pat. No. 4,937,189; EP220864 |
| TEF | translation elongation factor EF1-α (tef) | U.S. Pat. No. 6,265,185 |
| GPD, GPM | glyceraldehyde-3-phosphate-dehydrogenase (gpd), phosphoglycerate mutase (gpm) | U.S. Pat. Nos. 7,259,255 and 7,459,546; U.S. patent application Pub. No. 2011-0059496-A1 |
| GPDIN | glyceraldehyde-3-phosphate-dehydrogenase (gpd) | U.S. Pat. No. 7,459,546 |
| GPM/FBAIN | chimeric phosphoglycerate mutase (gpm)/fructose-bisphosphate aldolase (fba1) | U.S. Pat. No. 7,202,356 |
| FBA, FBAIN, FBAINm | fructose-bisphosphate aldolase (fba1) | U.S. Pat. No. 7,202,356 |
| GPAT | glycerol-3-phosphate O-acyltransferase (gpat) | U.S. Pat. No. 7,264,949 |
| YAT1 | ammonium transporter enzyme (yat1) | U.S. patent application Pub. Nos. 2006-0094102-A1 and 2010-0068789-A1 |
| EXP1 | export protein | U.S. Pat. No. 7,932,077 |

Additionally, Juretzek et al. (*Biotech. Bioprocess Eng.*, 5:320-326 (2000)) compares the glycerol-3-phosphate dehydrogenase ["G3P"], isocitrate lyase ["ICL1"], 3-oxo-acyl-CoA thiolase ["POT1"] and acyl-CoA oxidase ["POX1", "POX2" and "POX5"] promoters with respect to their regulation and activities during growth on different carbon sources.

Despite the utility of these known promoters, however, there is a need for new improved yeast promoters for metabolic engineering of yeast (i.e., oleaginous and non-oleaginous) and for controlling the expression of heterologous genes in yeast. Furthermore, possession of a suite of promoters that can be regulated under a variety of natural growth and induction conditions in yeast will play an important role in industrial settings, wherein economical production of heterologous and/or homologous polypeptides in commercial quantities is desirable.

It is believed that promoter regions derived from the *Yarrowia lipolytica* gene encoding diacylglycerol acyltransferase 2 ["DGAT2"] will be useful in expressing heterologous and/or homologous genes in transformed yeast, including *Yarrowia*.

SUMMARY OF THE INVENTION

In a first embodiment, the invention concerns a method for expressing a coding region of interest in a transformed yeast cell comprising:

a) providing a transformed yeast cell having a recombinant construct, wherein the recombinant construct comprises:

(1) a promoter region of a dgat2 *Yarrowia* gene; and (2) a coding region of interest which is expressible in the yeast cell;

wherein the promoter region is operably linked to the coding region of interest; and b) growing the transformed yeast cell of step (a) under conditions whereby the recombinant construct of step (a) is expressed.

In a second embodiment, the invention concerns a method for the production of an omega-3 fatty acid or omega-6 fatty acid comprising:
  a) providing a transformed oleaginous yeast cell comprising a recombinant construct, wherein the recombinant construct comprises:
    i) a promoter region of a dgat2 *Yarrowia* gene; and
    ii) a coding region encoding at least one omega-3 fatty acid or omega-6 fatty acid biosynthetic pathway enzyme;
  wherein the promoter region and the coding region are operably linked;
  b) growing the transformed oleaginous yeast of step (a) under conditions whereby the at least one omega-3 fatty acid or omega-6 fatty acid biosynthetic pathway enzyme is expressed and the omega-3 fatty acid or the omega-6 fatty acid is produced; and
  c) optionally recovering the omega-3 fatty acid or the omega-6 fatty acid.

In another aspect, the promoter region of a dgat2 *Yarrowia* gene may be selected from the group consisting of SEQ ID NO:33 and SEQ ID NO:34.

In some embodiments, the promoter region of a dgat2 *Yarrowia* gene may be as set forth in SEQ ID NO:19, wherein said promoter optionally comprises at least one modification selected from the group consisting of:
  (a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709 or 710 consecutive nucleotides, wherein the first nucleotide deleted is the cytosine nucleotide ['C'] at position 1 of SEQ ID NO:19;
  (b) substitution of a cytosine ['C'] nucleotide for the thymine ['T'] nucleotide at position 201 of SEQ ID NO:19;
  (c) substitution of an adenine ['A'] nucleotide or a guanine ['G'] nucleotide for the thymine ['T'] nucleotide at position +201 of SEQ ID NO:19;
  (d) substitution of a thymine ['T'] nucleotide for the cytosine ['C'] nucleotide at position +966 of SEQ ID NO:19;
  (e) substitution of an adenine ['A'] nucleotide or a guanine ['G'] nucleotide for the cytosine ['C'] nucleotide at position +966 of SEQ ID NO:19; and
  (f) any combination of part (a), part (b), part (c), part (d), and part (e) above.

More preferably, the promoter region of a dgat2 *Yarrowia* gene may be as set forth in SEQ ID NO:12, wherein said promoter comprises at least one modification selected from the group consisting of:
  a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 101, 102, 103, 104, 105, 106, 107, or 108, 109, 110, 111, 112, 113, 114, 115, 116, 117, or 118 consecutive nucleotides, wherein the first nucleotide deleted is the adenine nucleotide ['A'] at position 1 of SEQ ID NO:12;
  b) a deletion at the 3'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, or 87 consecutive nucleotides, wherein the first nucleotide deleted is the cytosine ['C'] at position 256 of SEQ ID NO:12; and
  c) a deletion of part (a) in combination with a substitution of a thymine ['T'] nucleotide, adenine ['A'] nucleotide or a guanine ['G'] nucleotide for the cytosine ['C'] nucleotide at position +256 of SEQ ID NO:12.

The promoter region of a dgat2 *Yarrowia* gene may be selected from the group consisting of SEQ ID NO:4, SEQ ID NO:6, SEQ ID NO:8, SEQ ID NO:10, and SEQ ID NO:12.

In various embodiments of the methods of the invention, the transformed yeast cell is an oleaginous yeast. This oleaginous yeast may be a member of a genus selected from the group consisting of *Yarrowia, Candida, Rhodotorula, Rhodosporidium, Cryptococcus, Trichosporon* and *Lipomyces*.

Additionally, provided herein is an isolated nucleic acid molecule comprising a promoter region of a dgat2 *Yarrowia* selected from the group consisting of:
(a) SEQ ID NO:4;
(b) SEQ ID NO:6;
(c) SEQ ID NO:8;
(d) SEQ ID NO:10;
(e) SEQ ID NO:12;
(f) SEQ ID NO:19, wherein said promoter optionally comprises at least one modification selected from the group consisting of:
(i) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709 or 710 consecutive nucleotides, wherein the first nucleotide deleted is the cytosine nucleotide ['C'] at position 1 of SEQ ID NO:19;
(ii) substitution of a cytosine ['C'] nucleotide for the thymine ['T'] nucleotide at position 201 of SEQ ID NO:19;
(iii) substitution of an adenine ['A'] nucleotide or a guanine ['G'] nucleotide for the thymine ['T'] nucleotide at position 201 of SEQ ID NO:19;
(iv) substitution of a thymine ['T'] nucleotide for the cytosine ['C'] nucleotide at position 966 of SEQ ID NO:19;
(v) substitution of an adenine ['A'] nucleotide or a guanine ['G'] nucleotide for the cytosine ['C'] nucleotide at position 966 of SEQ ID NO:19; and
(vi) any combination of part (i), part (ii), part (iii), part (iv), and part (v) above; and
(g) a promoter region comprising SEQ ID NO:34.

BRIEF DESCRIPTION OF THE DRAWINGS AND SEQUENCE DESCRIPTIONS

FIG. 1 graphically represents the relationship between SEQ ID NOs:13, 19, 4, 6, 8, 10, 12, and 33, each of which relates to promoter regions derived from the 5' upstream region of the diacylglycerol acyltransferase 2 ["DGAT2"] gene in *Yarrowia lipolytica*.

Figure 2A:
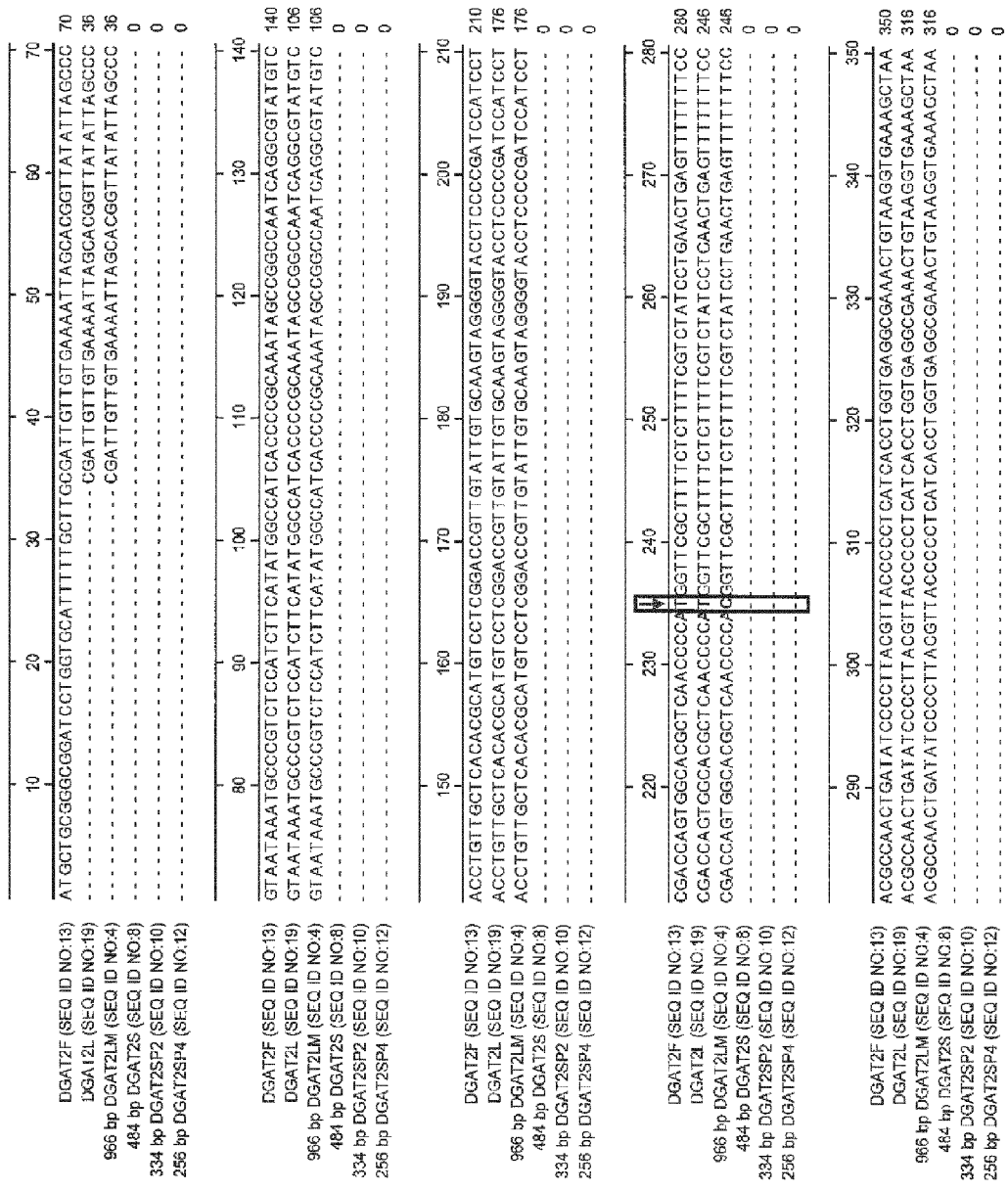
Figure 2B:
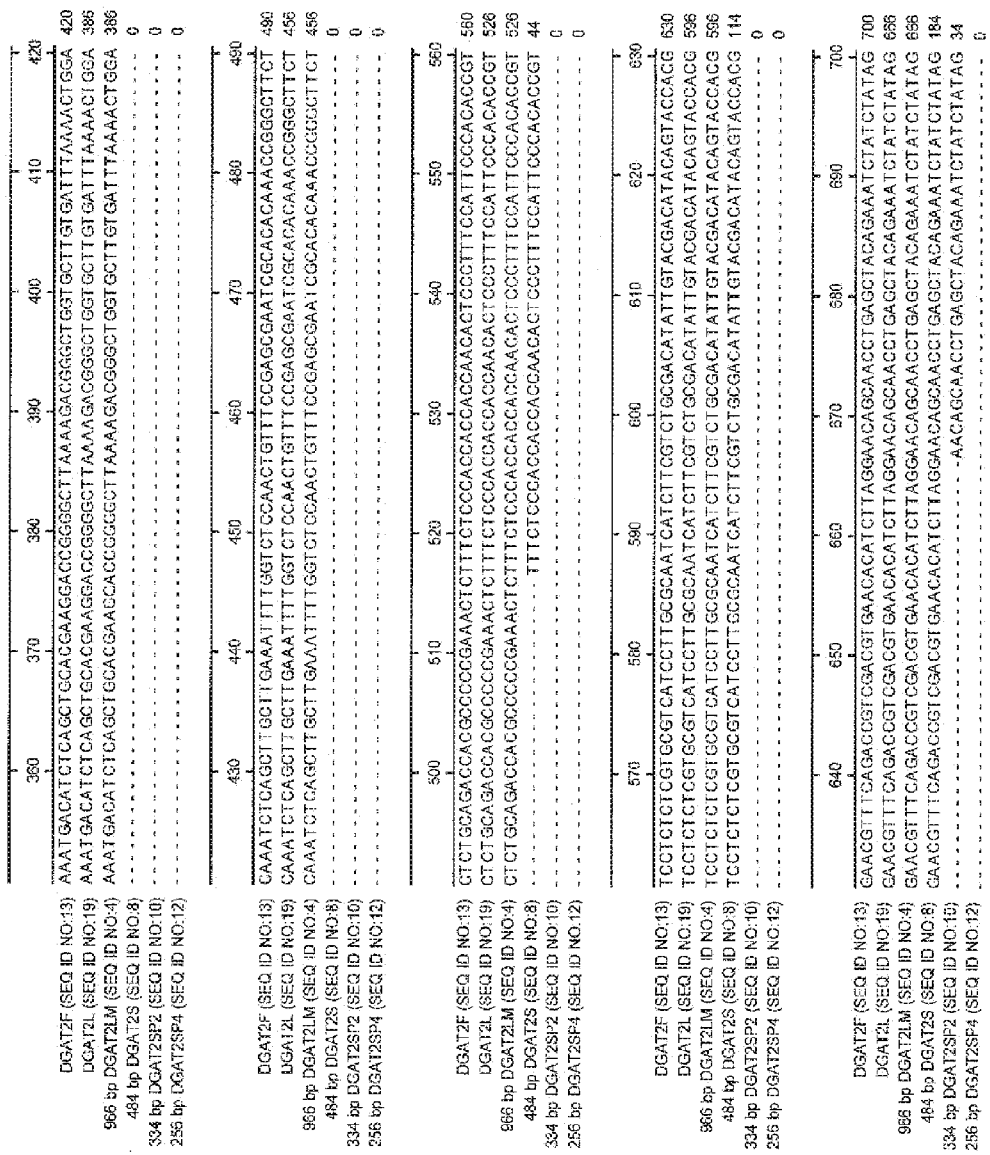
Figure 2C:
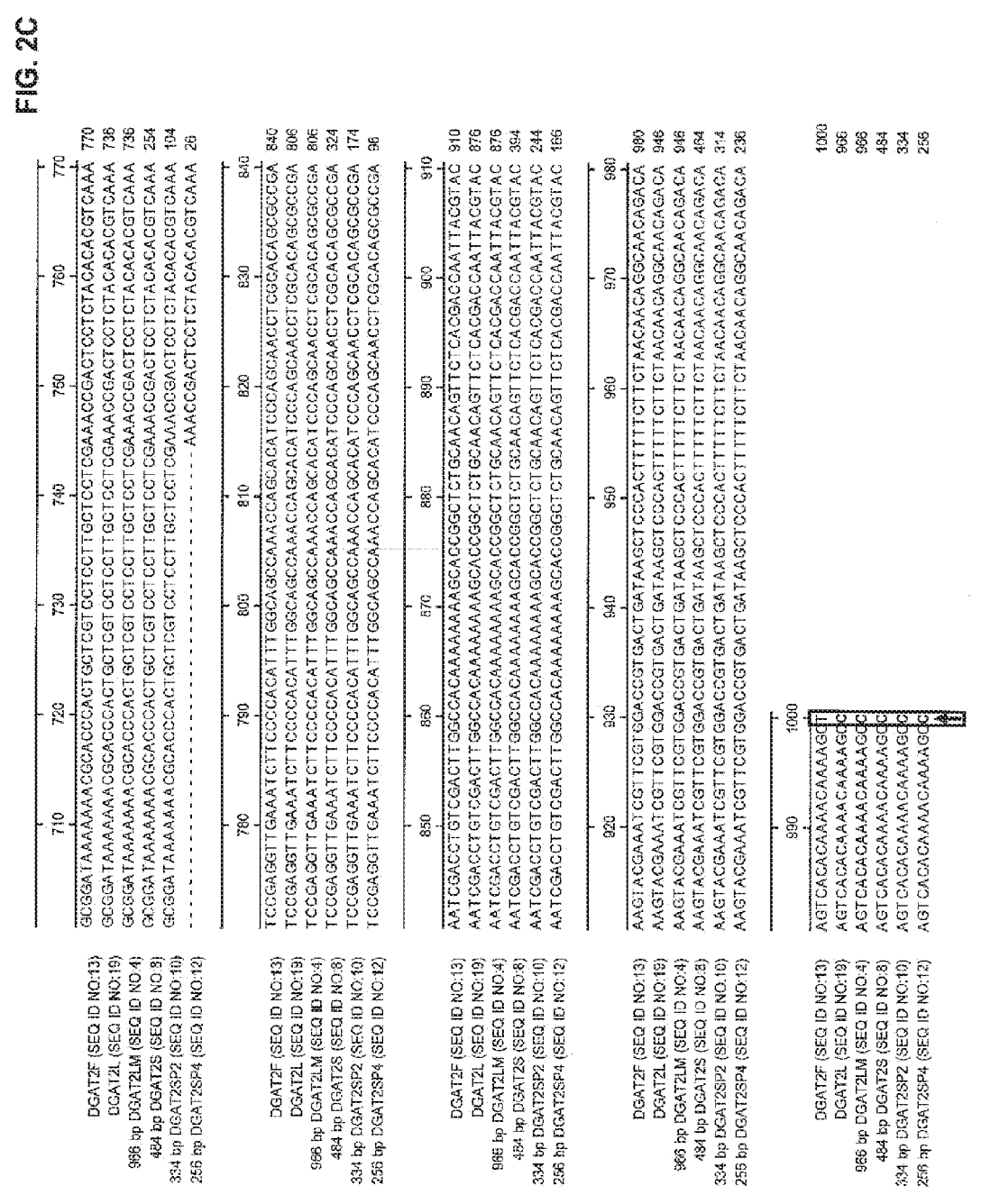

FIGS. 2A, 2B and 2C (which should be viewed together as FIG. 2) provide an alignment of the following *Y. lipolytica* promoter regions:
(a) the *Y. lipolytica* DGAT2F (SEQ ID NO:13) promoter region, which is the 1000 bp 5' upstream sequence (i.e., the −1000 to −1 region) of the diacylglycerol acyltransferase 2 ["DGAT2"] gene in *Y. lipolytica*, wherein the nucleotide 'A' of the DGAT2 translation initiation codon 'ATG' was designated as +1 (note that the ATG codon is not shown in the figure);
(b) the 966 bp DGAT2L (SEQ ID NO:19) promoter region;
(c) the 966 bp DGAT2LM (SEQ ID NO:4) promoter region;
(d) the 484 bp DGAT2S (SEQ ID NO:8) promoter region;
(e) the 334 bp DGAT2SP2 (SEQ ID NO:10) promoter region; and
(f) the 256 bp DGAT2SP4 (SEQ ID NO:12) promoter region.

Base pair differences are highlighted with an arrow and box.

Figure 3:
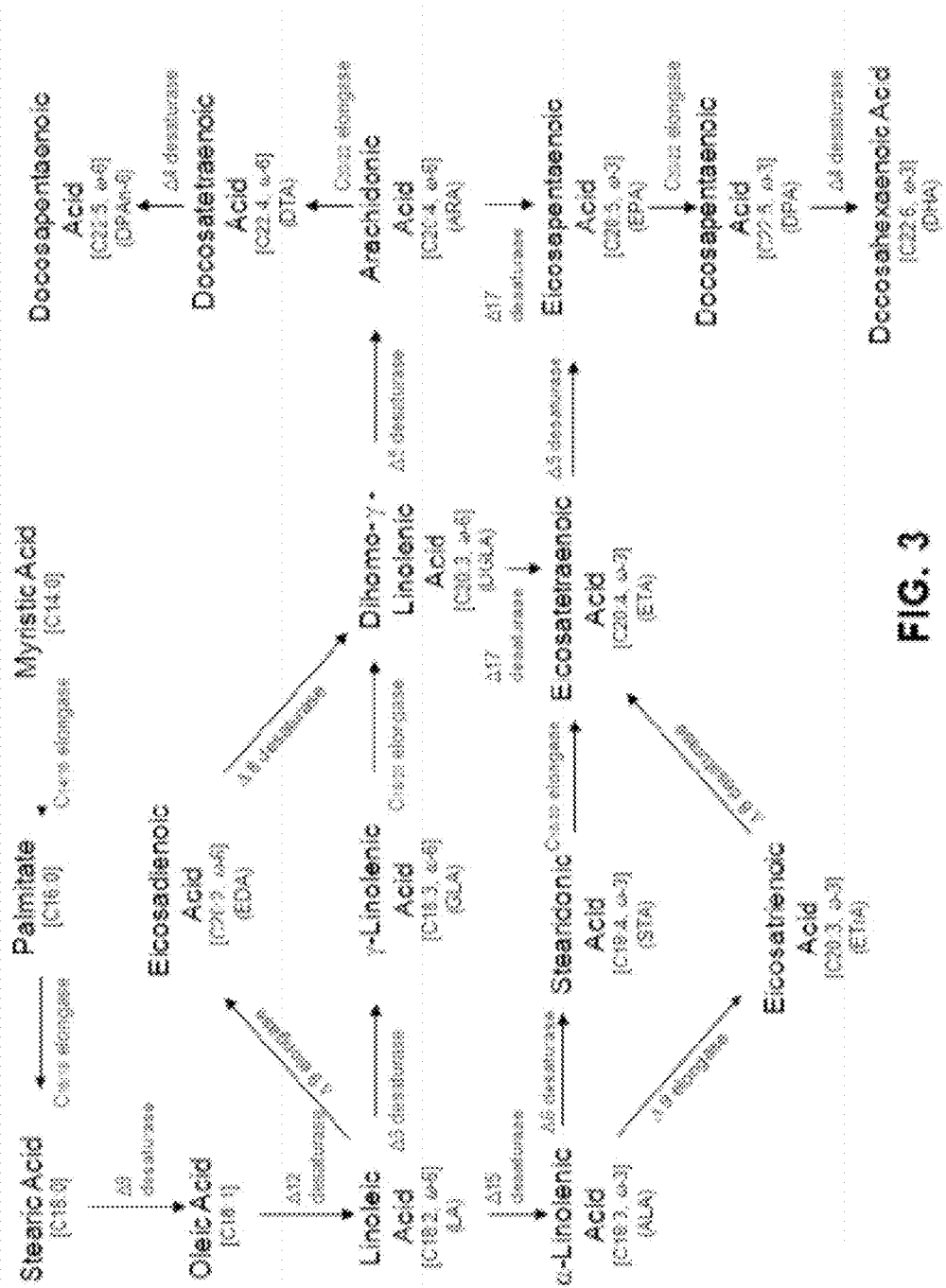

FIG. 3 illustrates the omega-3/omega-6 fatty acid biosynthetic pathway.

Figure 4B:
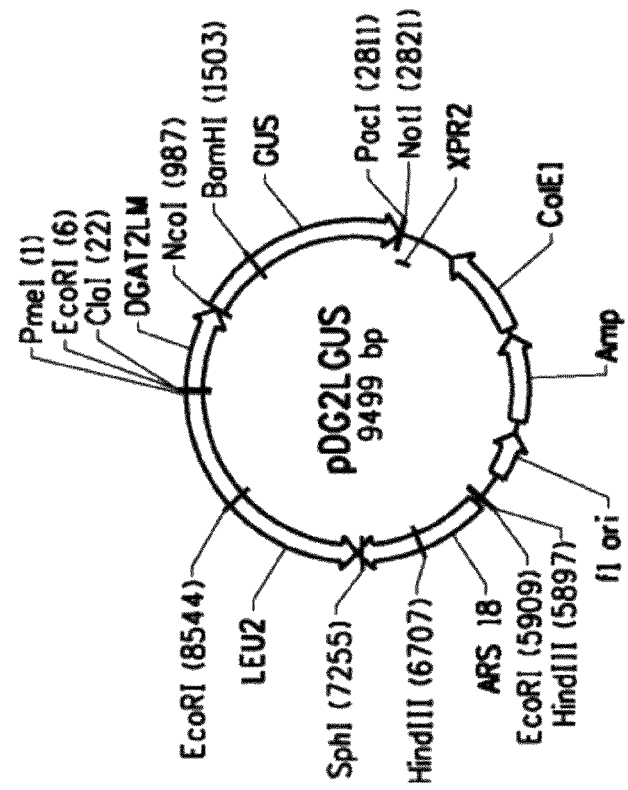
Figure 4A:
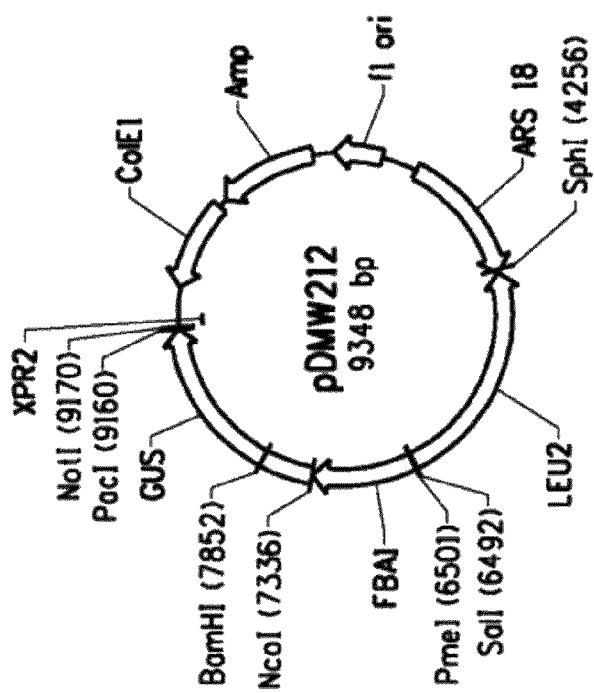

FIG. 4 provides plasmid maps for the following: (A) pDMW212 and (B) pDG2LGUS.

Figure 5:
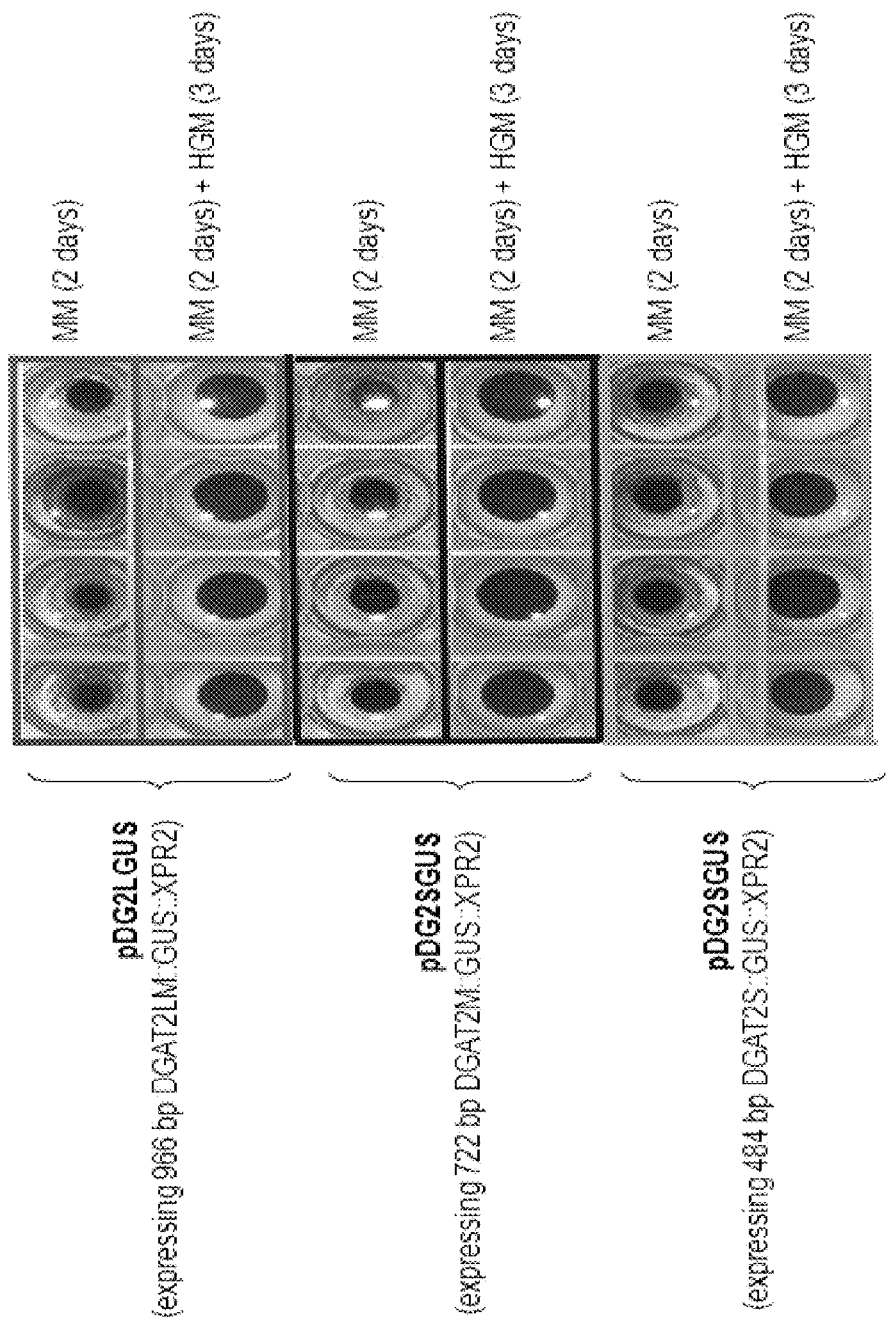

FIG. 5 is an image of cell cultures comparing the promoter activity of 966 bp DGAT2LM (SEQ ID NO:4), 722 bp DGAT2M (SEQ ID NO:6) and 484 bp DGAT2S (SEQ ID NO:8) in *Yarrowia lipolytica* as determined by histochemical staining.

The invention can be more fully understood from the following detailed description and the accompanying sequence descriptions, which form part of this application.

SEQ ID NOs:1-36 are promoters, ORFs encoding genes (or portions thereof), primers, or plasmids, as identified in Table 2.

TABLE 2

Summary of Nucleic Acid SEQ ID Numbers

| Description | Nucleic acid SEQ ID NO. |
|---|---|
| *Yarrowia lipolytica* DGAT2 (U.S. Pat. No. 7,267,976; U.S. Pat. No. 7,521,223) | 1 (2119 bp) |
| *Yarrowia lipolytica* DGAT1 (U.S. Pat. No. 7,273,746) | 2 (1578 bp) |
| Plasmid pDG2LGUS | 3 (9499 bp) |
| 966 bp DGAT2LM *Yarrowia* promoter region | 4 (966 bp) |
| Plasmid pDG2MGUS | 5 (9237 bp) |
| 722 bp DGAT2M *Yarrowia* promoter region | 6 (722 bp) |
| Plasmid pDG2SGUS | 7 (9016 bp) |
| 484 bp DGAT2S *Yarrowia* promoter region | 8 (484 bp) |
| Plasmid pDG2SP2GUS | 9 (8847 bp) |
| 334 bp DGAT2SP2 *Yarrowia* promoter region | 10 (334 bp) |
| Plasmid pDG2SP4GUS | 11 (8768 bp) |
| 256 bp DGAT2SP4 *Yarrowia* promoter region | 12 (256 bp) |
| 1000 bp DGAT2F *Yarrowia* promoter region | 13 (1000 bp) |
| Primer Y1189 | 14 (31 bp) |
| Primer Y1191 | 15 (37 bp) |
| Primer Y1190 | 16 (37 bp) |
| Plasmid pT-DG2LPro | 17 (4936 bp) |
| Plasmid pT-DG2SPro | 18 (4449 bp) |
| 966 bp DGAT2L *Yarrowia* promoter region | 19 (966 bp) |
| Plasmid pT-DGAT2LPro-(-N) | 20 (4936 bp) |
| Primer Y1192 | 21 (35 bp) |
| Primer Y1193 | 22 (35 bp) |
| Plasmid pT-DGAT2LPro-P | 23 (4935 bp) |
| Primer Y1220 | 24 (39 bp) |
| Primer Y1221 | 25 (39 bp) |
| 965 bp DGAT2L-Pme *Yarrowia* promoter region | 26 (965 bp) |
| Primer Y2160 | 27 (38 bp) |
| Primer Y2161 | 28 (38 bp) |
| Plasmid pDG2SGUS-P | 29 (9020 bp) |
| Plasmid pDG2SGUS-P3 | 30 (9019 bp) |
| Primer Y2164 | 31 (38 bp) |
| Primer Y2165 | 32 (38 bp) |
| 51 bp DGAT2 minimal *Yarrowia* promoter region | 33 (51 bp) |
| 138 bp DGAT2 *Yarrowia* promoter region | 34 (138 bp) |
| Plasmid pDMW212 | 35 (9348 bp) |
| YALI0E32769g locus (DGAT2 gene) | 36 (2845 bp) |

DETAILED DESCRIPTION OF THE INVENTION

All patents, patent applications, and publications cited herein are hereby incorporated by reference in their entirety.

In this disclosure, a number of terms and abbreviations are used. The following definitions are provided.

"Open reading frame" is abbreviated "ORF".

"Polymerase chain reaction" is abbreviated "PCR".

"American Type Culture Collection" is abbreviated "ATCC".

"Polyunsaturated fatty acid(s)" is abbreviated "PUFA(s)".

"Triacylglycerols" are abbreviated "TAGs".

The term "yeast" refers to a phylogenetically diverse grouping of single-celled fungi. Yeast do not form a specific taxonomic or phylogenetic grouping, but instead comprise a diverse assemblage of unicellular organisms that occur in the Ascomycotina and Basidiomycotina. Collectively, about 100 genera of yeast have been identified, comprising approximately 1,500 species (Kurtzman and Fell, *Yeast Systematics And Phylogeny: Implications Of Molecular Identification Methods For Studies In Ecology.* In C. A. Rosa and G. Peter, eds., *The Yeast Handbook.* Germany: Springer-Verlag Berlin Herdelberg, 2006). Yeast reproduce principally by budding (or fission) and derive energy from fermentation, via conversion of carbohydrates to ethanol and carbon dioxide. Examples of some yeast genera include, but are not limited to: *Agaricostilbum, Ambrosiozyma, Arthroascus, Arxula, Ashbya, Babjevia, Bensingtonia, Botryozyma, Brettanomyces, Bullera, Candida, Clavispora, Cryptococcus, Cystofilobasidium, Debaryomyces, Dekkera, Dipodascus, Endomyces, Endomycopsella, Erythrobasidium, Fellomyces, Filobasidium, Galactomyces, Geotrichum, Guilliermondella, Hansenula, Hanseniaspora, Kazachstania, Kloeckera, Kluyveromyces, Kockovaella, Kodamaea, Komagataella, Kondoa, Lachancea, Leucosporidium, Leucosporidiella, Lipomyces, Lodderomyces, Issatchenkia, Magnusiomyces, Mastigobasidium, Metschnikowia, Monosporella, Myxozyma, Nadsonia, Nematospora, Oosporidium, Pachysolen, Pichia, Phaffia, Pseudozyma, Reniforma, Rhodosporidium, Rhodotorula, Saccharomyces, Saccharomycodes, Saccharomycopsis, Saturnispora, Schizoblastosporion, Schizosaccharomyces, Sirobasidium, Smithiozyma, Sporobolomyces, Sporopachydermia, Starmerella, Sympodiomycopsis, Sympodiomyces, Torulaspora, Tremella, Trichosporon, Trichosporiella, Trigonopsis, Udeniomyces, Wickerhamomyces, Williopsis, Xanthophyllomyces, Yarrowia, Zygosaccharomyces, Zygotorulaspora, Zymoxenogloea* and *Zygozyma.*

The term "oleaginous" refers to those organisms that tend to store their energy source in the form of oil (Weete, In: Fungal Lipid Biochemistry, 2$^{nd}$ Ed., Plenum, 1980). Generally, the cellular oil content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.,* 57:419-25 (1991)). It is common for oleaginous microorganisms to accumulate in excess of about 25% of their dry cell weight as oil.

The term "oleaginous yeast" refers to those microorganisms classified as yeasts that can make oil. Examples of oleaginous yeast include, but are not limited to, the following genera: *Yarrowia, Candida, Rhodotorula, Rhodosporidium, Cryptococcus, Trichosporon* and *Lipomyces.* Alternatively, organisms classified as yeasts that are genetically modified to become oleaginous such that they can produce more than 25% of their dry cell weight as oil are also "oleaginous", e.g., yeast such as *Saccharomyces cerevisiae* (Intl Appl. Publ. No. WO 2006/102342).

The term "fermentable carbon source" will refer to a carbon source that a microorganism will metabolize to derive energy. Typical carbon sources for use in the methods herein include, but are not limited to: monosaccharides, disaccharides, oligosaccharides, polysaccharides, alkanes, fatty acids, esters of fatty acids, glycerol, monoglycerides, diglycerides, triglycerides, carbon dioxide, methanol, formaldehyde, formate and carbon-containing amines. Most preferred is glucose, sucrose, invert sucrose, fructose, glycerol and/or fatty acids containing between 10-22 carbons. The term "invert sucrose" (or "invert sugar") refers to a mixture comprising equal parts of fructose and glucose resulting from the hydrolysis of sucrose. Invert sucrose may be a mixture comprising 25 to 50% glucose and 25 to 50% fructose. Invert sucrose may also comprise sucrose, the amount of which depends on the degree of hydrolysis.

The term "DGAT" refers to a diacylglycerol acyltransferase enzyme (also known as an acyl-CoA-diacylglycerol acyltransferase or a diacylglycerol O-acyltransferase) (EC 2.3.1.20). This enzyme is responsible for the conversion of acyl-CoA and 1,2-diacylglycerol to TAG and CoA (thereby involved in the terminal step of TAG biosynthesis). Two families of DGAT enzymes exist: DGAT1 and DGAT2. The former family shares homology with the acyl-CoA:cholesterol acyltransferase gene family, while the latter family is unrelated (Lardizabal et al., *J. Biol. Chem.* 276(42):38862-28869 (2001)).

The term "DGAT2" refers to a diacylglycerol acyltransferase 2 enzyme encoded by the dgat2 gene.

A "dgat2 *Yarrowia* gene" refers to a gene encoding DGAT2 from a yeast of the genus *Yarrowia*. For example, a 2119 bp DNA sequence that encodes the *Yarrowia lipolytica* DGAT2 enzyme is provided as SEQ ID NO:1 (U.S. Pat. No. 7,521, 223). Specifically, the sequence comprises a 1545 bp coding region (nucleotides 291 to 1835) with a deduced amino acid sequence 514 residues in length.

The term "promoter region of a dgat2 *Yarrowia* gene" or "*Yarrowia* DGAT2 promoter region" refers to the 5' upstream untranslated region in front of the 'ATG' translation initiation codon of a *Yarrowia* DGAT2 gene, or sequences derived therefrom, and that is necessary for expression. Thus, it is believed that promoter regions of a dgat2 *Yarrowia* gene will comprise a portion of the ~1000 bp 5' upstream of a dgat2 *Yarrowia* gene. The sequence of the *Yarrowia* DGAT2 promoter region may correspond exactly to native sequence upstream of the dgat2 *Yarrowia* gene (i.e., a "wildtype" or "native" *Yarrowia* DGAT2 promoter); alternately, the sequence of the *Yarrowia* DGAT2 promoter region may be "modified" or "mutated", thereby comprising various substitutions, deletions, and/or insertions of one or more nucleotides relative to a wildtype or native *Yarrowia* DGAT2 promoter. These modifications can result in a modified *Yarrowia* DGAT2 promoter having increased, decreased or equivalent promoter activity, when compared to the promoter activity of the corresponding wildtype or native *Yarrowia* DGAT2 promoter. The term "mutant promoter" or "modified promoter" will encompass natural variants and in vitro generated variants obtained using methods well known in the art (e.g., classical mutagenesis, site-directed mutagenesis and "DNA shuffling").

Described herein is a wildtype *Yarrowia* DGAT2 promoter region (SEQ ID NO:13) comprising the −1000 to −1 upstream region of the DGAT2 gene (SEQ ID NO:36) based on nucleotide numbering such that the 'A' position of the 'ATG' translation initiation codon is designated as +1. The ATG translation initiation codon is located at nucleotide positions 1001-1003 in SEQ ID NO:36. Alternately, and yet by no means limiting in nature, a wildtype *Yarrowia* DGAT2 promoter region may comprise the −966 to −1 region of SEQ ID NO:36, the −722 to −1 region of SEQ ID NO:36, the −484 to −1 region of SEQ ID NO:36, the −334 to −1 region of SEQ ID NO:36, the −256 to −1 region of SEQ ID NO:36, the −138 to −1 region of SEQ ID NO:36, or the −138 to −87 region of SEQ ID NO:36 (where the "−1" position in SEQ ID NO:36 is the nucleotide that is 5'-adjacent to the ATG translation initiation codon). Similarly, a modified *Yarrowia* DGAT2 promoter region may comprise the promoter region of a dgat2 *Yarrowia* gene as set forth in SEQ ID NO:19, wherein said promoter optionally comprises at least one modification selected from the group consisting of:

(a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709 or 710 consecutive nucleotides, wherein the first nucleotide deleted is the cytosine nucleotide ['C'] at position 1 of SEQ ID NO:19;

(b) substitution of a cytosine ['C'] nucleotide for the thymine ['T'] nucleotide at position 201 of SEQ ID NO:19;

(c) substitution of an adenine ['A'] nucleotide or a guanine ['G'] nucleotide for the thymine ['T'] nucleotide at position 201 of SEQ ID NO:19;

(d) substitution of a thymine ['T'] nucleotide for the cytosine ['C'] nucleotide at position 966 of SEQ ID NO:19;

(e) substitution of an adenine ['A'] nucleotide or a guanine ['G'] nucleotide for the cytosine ['C'] nucleotide at position +966 of SEQ ID NO:19; and (f) any combination of part (a), part (b), part (c), part (d), and part (e) above.

These examples are not intended to be limiting in nature and will be elaborated below. FIG. 1 graphically illustrates various Yarrowia DGAT2 promoter regions (i.e., SEQ ID NO:19 [966 bp DGAT2L], SEQ ID NO:4 [966 bp DGAT2LM], SEQ ID NO:6 [722 bp DGAT2M], SEQ ID NO:8 [484 bp DGAT2S], SEQ ID NO:10 [334 bp DGAT2SP2], SEQ ID NO:12 [256 bp DGAT2SP4], and SEQ ID NO:33 [51 bp Minimal DGAT2 promoter]), with the 1000 bp 5' upstream region (SEQ ID NO:13) of the DGAT2 initiation codon of the Yarrowia dgat2 gene as a reference.

The term "promoter activity" will refer to an assessment of the transcriptional efficiency of a promoter. This may, for instance, be determined directly by measurement of the amount of mRNA transcription from the promoter (e.g., by quantitative PCR or Northern blotting or primer extension methods) or indirectly by measuring the amount of gene product expressed from the promoter.

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "substantial portion" of an amino acid sequence or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid molecule comprising the primers. Accordingly, a "substantial portion" of a nucleotide sequence comprises enough of the sequence to specifically identify and/or isolate a nucleic acid molecule comprising the sequence.

The disclosure herein teaches partial or complete nucleotide sequences containing one or more particular yeast promoters. The skilled artisan, having the benefit of the sequences as reported herein, may now use all or a substantial portion of the disclosed sequences for purposes known to those skilled in this art. Accordingly, the complete sequences as reported in the accompanying Sequence Listing, as well as substantial portions of those sequences as defined above, are encompassed in the present disclosure.

The term "complementary" is used to describe the relationship between nucleotide bases that are capable of hybridizing to one another. For example, with respect to DNA, adenosine is complementary to thymine and cytosine is complementary to guanine. Accordingly, isolated nucleic acid fragments that are complementary to the complete sequences as reported in the accompanying Sequence Listing, as well as those substantially similar nucleic acid sequences, are encompassed in the present disclosure.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the disclosure herein encompasses more than the specific exemplary sequences.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

Methods to determine "percent identity" and "percent similarity" are codified in publicly available computer programs. Percent identity and percent similarity can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humania: NJ (1994); 4) *Sequence Analysis in Molecular Biology* (von Heinje, G., Ed.) Academic (1987); and, 5) *Sequence Analysis Primer* (Gribskov, M. and Devereux, J., Eds.) Stockton: NY (1991).

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" and the "Clustal W method of alignment" (described by Higgins and Sharp, *CABIOS*, 5:151-153 (1989); Higgins, D. G. et al., *Comput. Appl. Biosci.*, 8:189-191 (1992)) and found in the MegAlign™ (version 8.0.2) program of the LASERGENE bioinformatics computing suite (DNASTAR Inc.). After alignment of the sequences using either Clustal program, it is possible to obtain a "percent identity" by viewing the "sequence distances" table in the program.

For multiple alignments using the Clustal V method of alignment, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

Default parameters for multiple alignment using the Clustal W method of alignment correspond to GAP PENALTY=10, GAP LENGTH PENALTY=0.2, Delay Divergent Seqs(%)=30, DNA Transition Weight=0.5, Protein Weight Matrix=Gonnet Series, DNA Weight Matrix=IUB.

The "BLASTN method of alignment" is an algorithm provided by the National Center for Biotechnology Information ["NCBI"] to compare nucleotide sequences using default parameters, while the "BLASTP method of alignment" is an algorithm provided by the NCBI to compare protein sequences using default parameters.

It is well understood by one skilled in the art that many levels of sequence identity are useful in identifying polypeptides from other species, wherein such polypeptides have the same or similar function or activity. Likewise, suitable promoter regions (isolated polynucleotides of the present invention) are at least about 70-85% identical, and more preferably at least about 85-95% identical to the nucleotide sequences reported herein. Although preferred ranges are described above, useful examples of percent identities include any integer percentage from 70% to 100%, such as 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable *Yarrowia* DGAT2 promoter regions not only have the above homologies but typically are at least 50 nucleotides in length, more preferably at least 100 nucleotides in length, more preferably at least 250 nucleotides in length, and more preferably at least 500 nucleotides in length.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These oligonucleotide building blocks are annealed and then ligated to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. Chimeric genes herein will typically comprise a promoter region of a dgat2 *Yarrowia* gene operably linked to a coding region of interest. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence which codes for a specific amino acid sequence. The terms "coding sequence" and "coding region" are used interchangeably herein. A "coding region of interest" is a coding region which is desired to be expressed. Such coding regions are discussed more fully hereinbelow. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, enhancers, silencers, 5' untranslated leader sequence (e.g., between the transcription start site and translation initiation codon), introns, polyadenylation recognition sequences, RNA processing sites, effector binding sites and stem-loop structures.

"Promoter" refers to a DNA sequence that facilitates transcription of a coding sequence, thereby enabling gene expression. In general, a promoter is typically located on the same strand and upstream of the coding sequence (i.e., 5' of the coding sequence). Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed at almost all stages of development are commonly referred to as "constitutive promoters". It is further recognized that since in most cases the exact boundaries of regulatory sequences (especially at their 5' end) have not been completely defined, DNA fragments of some variation may have identical promoter activity.

"Minimal promoter" refers to the minimal length of DNA sequence that is necessary to initiate basal level transcription of an operably linked coding sequence. The "minimal promoter" usually does not include the untranslated region located between transcription start site and translation start site. Although promoters often interact with the TATA binding protein ["TBP"] to create a transcription initiation complex from which RNA polymerase II transcribes the DNA coding sequence, only some promoters contain a TATA box to which TBP binds directly. In yeast, the TATA-box is usually located about 20 to 130 bp upstream of the transcription start site. For those TATA-less promoters, it is thought that transcription factor TFIID coordinates delivery of TBP and functions largely to stabilize TBP binding in lieu of a TATA box (Basehoar et al., *Cell*, 116:699-709 (2004)). Some TATA-less promoters contain an "initiator" element [Zhang, Z., and Dietrich, F. S., *Nucleic Acids Res.* 33:2838-2851 (2005), incorporated herein by reference] located around the transcription start site, which can direct basal level transcription.

Thus, the minimal promoter region for the dgat2 TATA-less promoters is herein defined as the −138 to −87 region upstream of the dgat2 gene (i.e., as set forth in SEQ ID NO:33), which contains initiator elements sufficient to initiate basal level transcription of an operably linked coding sequence. Alternately, the −138 to −1 region will also be a useful minimal promoter region (SEQ ID NO:34).

The terms "3' non-coding sequences", "transcription terminator" and "termination sequences" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

The term "enhancer" refers to a cis-regulatory sequence that can elevate levels of transcription from an adjacent eukaryotic promoter, thereby increasing transcription of the gene. Enhancers can act on promoters over many kilobases of DNA and can be 5' or 3' to the promoter they regulate. Enhancers can also be located within introns (Giacopelli F. et al., *Gene Expr.*, 11:95-104 (2003)).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to an RNA transcript that is complementary to all or part of a target primary transcript or mRNA, and that blocks the expression of a target gene (U.S. Pat. No. 5,107,065).

The term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

The term "recombinant" refers to an artificial combination of two otherwise separated segments of sequence, e.g., by chemical synthesis or by the manipulation of isolated segments of nucleic acids by genetic engineering techniques.

The term "expression", as used herein, refers to the transcription and stable accumulation of sense (mRNA) or antisense RNA. Expression may also refer to translation of mRNA into a protein (either precursor or mature).

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" or "transformant" organisms.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "expression cassette" refers to a fragment of DNA containing a foreign gene and having elements in addition to the foreign gene that allow for expression of that gene in a foreign host. Generally, an expression cassette will comprise the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence ["ORF"]; and, 3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a recombinant construct may comprise one or more expression cassettes. In another example, a recombinant DNA construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments described herein. The skilled artisan will also recognize that different independent transformation events will result in different levels and patterns of expression (Jones et al., *EMBO J.*, 4:2411-2418 (1985); De Almeida et al., *Mol. Gen. Genetics*, 218:78-86 (1989)), and thus that multiple events must be screened in order to obtain strains displaying the desired expression level and pattern. Such screening may be accomplished by Southern analysis of DNA, Northern analysis of mRNA expression, Western and/or Elisa analyses of protein expression, formation of a specific product, phenotypic analysis or GC analysis of the PUFA products, among others.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.*, 215:403-410 (1990)); 3) DNASTAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within this description, whenever sequence analysis software is used for analysis, the analytical results are based on the "default values" of the program referenced, unless otherwise specified. As used herein "default values" will mean any set of values or parameters that originally load with the software when first initialized.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Cold Spring Harbor, N.Y. (1989); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

The DGAT1 family of enzymes includes those enzymes that are related to the acyl-CoA:cholesterol acyltransferase (ACAT) gene family, while the DGAT2 family of enzymes includes those enzymes that are unrelated to the ACAT family (Lardizabal et al., *J. Biol. Chem.* 276(42):38862-38869 (2001)). Within *Yarrowia lipolytica*, both a DGAT1 (U.S. Pat. No. 7,273,746; SEQ ID NO:2 herein) and a DGAT2 (U.S. Pat. Nos. 7,267,976 and 7,521,223; SEQ ID NO:1 herein) have been identified. DGAT2 has been identified as a key enzyme controlling TAG biosynthesis. Specifically, *Yarrowia* mutants having their native DGAT2 knocked-out can only accumulate about 20% TAG when compared to the wildtype strains (U.S. Pat. No. 7,267,976).

Based on the above, the dgat2 gene was identified as a potential source of new and improved yeast promoters for metabolic engineering of yeast and for controlling heterologous genes in yeast. In order to understand the means by which DGAT2 expression is regulated in *Yarrowia*, the DGAT2 promoter was isolated and its functional structure was mechanistically analyzed.

In general, a promoter useful for controlling the expression of heterologous genes in yeast should preferably meet criteria with respect to strength, activities, pH tolerance and inducibility, as described in U.S. Pat. No. 7,259,255. Additionally, today's complex metabolic engineering utilized for construction of yeast having the capability to produce a variety of heterologous polypeptides in commercial quantities requires a suite of promoters that are regulatable under a variety of natural growth and induction conditions.

Thus, described herein are a suite of promoter regions of a dgat2 *Yarrowia* gene, useful for driving expression of any suitable coding region of interest in a transformed yeast cell. More specifically, described herein is an isolated nucleic acid molecule comprising a promoter region of a dgat2 *Yarrowia* gene, wherein said promoter region of a dgat2 *Yarrowia* gene is set forth in SEQ ID NO:19 (corresponding to the 5' upstream −966 to −1 region of the *Yarrowia* dgat2 gene, SEQ ID NO:36), and wherein said promoter optionally comprises at least one modification selected from the group consisting of:

(a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709 or 710 consecutive nucleotides, wherein the first nucleotide deleted is the cytosine nucleotide ['C'] at position 1 of SEQ ID NO:19;
(b) substitution of a cytosine ['C'] nucleotide for the thymine ['T'] nucleotide at position 201 of SEQ ID NO:19;
(c) substitution of an adenine ['A'] nucleotide or a guanine ['G'] nucleotide for the thymine ['T'] nucleotide at position 201 of SEQ ID NO:19;
(d) substitution of a thymine ['T'] nucleotide for the cytosine ['C'] nucleotide at position 966 of SEQ ID NO:19; and,
(e) substitution of an adenine ['A'] nucleotide or a guanine ['G'] nucleotide for the cytosine ['C'] nucleotide at position 966 of SEQ ID NO:19; and
(f) any combination of part (a), part (b), part (c), part (d), and part (e) above.

In some embodiments, the promoter region of a dgat2 Yarrowia gene is selected from the group consisting of SEQ ID NOs:13, 19, 4, 6, 8, 10, and 12. These promoter regions are preferred to provide relatively high levels of constitutive promoter activity when operably linked to a coding region of interest.

The relationship between the promoter regions of a Yarrowia dgat2 gene selected from the group consisting of SEQ ID NOs:13, 19, 4, 8, 10, and 12 is readily observed upon alignment of the individual promoter sequences. Specifically, FIG. 2 (comprising FIGS. 2A, 2B and 2C) provides an alignment of:
(a) the 1000 bp promoter region DGAT2F (SEQ ID NO:13);
(b) the 966 bp promoter region DGAT2L (SEQ ID NO:19);
(c) the 966 bp promoter region DGAT2LM (SEQ ID NO:4);
(d) the 484 bp promoter region DGAT2S (SEQ ID NO:8);
(e) the 334 bp promoter region DGAT2SP2 (SEQ ID NO:10); and,
(f) the 256 bp promoter region DGAT2SP4 (SEQ ID NO:12).
Nucleotide differences are highlighted with a box and an arrow.

As will be obvious to one of skill in the art, the above discussion is by no means limiting to the description of suitable promoter regions of a dgat2 Yarrowia gene. For example, alternate Yarrowia DGAT2 promoter regions may be longer than the 1000 bp sequence 5' upstream of the nucleotide 'A' (designated as +1) of the translation initiation codon 'ATG' of SEQ ID NO:36, thereby encompassing additional nucleotides.

Similarly, it should be recognized that promoter fragments of various diminishing lengths may have identical promoter activity, since the exact boundaries of the regulatory sequences have not been completely defined. Thus, for example, it is also contemplated that a suitable promoter region of a dgat2 Yarrowia gene could also include a promoter region of SEQ ID NO:19, wherein the 5'-terminus deletion was greater than 710 consecutive nucleotides.

More specifically, based on sequence analysis of the promoter region set forth in SEQ ID NO:12, and identification of two possible transcription initiator elements upstream of the ATG translation initiation codon, it is hypothesized herein that the minimal promoter region that could function for basal level transcription initiation of an operably linked coding region of interest encompasses (at least) the 51 bp 5' upstream untranslated region from the 'ATG' translation initiation codon of a dgat2 Yarrowia gene comprising the −138 to −87 region of SEQ ID NO:36; this 51 bp region is set forth independently as SEQ ID NO:33.

In alternate embodiments, SEQ ID NO:33 could be utilized as an enhancer to elevate levels of transcription from an adjacent eukaryotic promoter, thereby increasing transcription of a coding region of interest. One of skill in the art would readily be able to conduct appropriate deletion studies to determine the appropriate length of a promoter region of a dgat2 Yarrowia gene required to enable the desired level of promoter activity.

Thus, in alternate embodiments, described herein is an isolated nucleic acid molecule comprising a promoter region of a dgat2 Yarrowia gene, wherein said isolated nucleic acid molecule is selected from the group consisting of SEQ ID NO:4, SEQ ID NO: 6, SEQ ID NO:8, SEQ ID NO:10, SEQ ID NO:12, and SEQ ID NO:34.

More specifically, additional variant Yarrowia DGAT2 promoter regions may be constructed, wherein the DNA sequence of the promoter has one or more nucleotide substitutions (i.e., deletions, insertions, substitutions, or addition of one or more nucleotides in the sequence) which do not affect (in particular, impair) the yeast promoter activity. Regions that can be modified without significantly affecting the yeast promoter activity can be identified by deletion studies. A variant promoter of the present invention has at least about 10%, more preferably at least about 20%, more preferably at least about 40%, more preferably at least about 60%, more preferably at least about 80%, more preferably at least about 90%, more preferably at least about 100%, more preferably at least about 200%, more preferably at least about 300% and most preferably at least about 500% of the promoter activity of any of the Yarrowia DGAT2 promoter regions described herein as SEQ ID NO:4, SEQ ID NO:6, SEQ ID NO:8, SEQ ID NO:10 or SEQ ID NO:12.

U.S. Pat. No. 7,259,255 describes a variety of methods for mutagenesis suitable for the generation of mutant promoters. This would permit production of a putative promoter having, for example, a more desirable level of promoter activity in the host cell or a more desirable sequence for purposes of cloning (e.g., removal of a restriction enzyme site within the native promoter region). Similarly, the cited reference also discusses means to examine regions of a nucleotide of interest important for promoter activity (i.e., functional analysis via deletion mutagenesis to determine the minimum portion of the putative promoter necessary for activity).

All variant promoter regions of a dgat2 Yarrowia gene, derived from the promoter regions described herein, are within the scope of the present disclosure.

Similarly, it should be noted that one could isolate regions upstream of the DGAT2 initiation codon in various Yarrowia species and strains, other than the region isolated herein from Yarrowia lipolytica ATCC #20362, and thereby identify alternate promoter regions of a dgat2 Yarrowia gene. As is well known in the art, isolation of homologous promoter regions or genes using sequence-dependent protocols is readily possible using various techniques (see, U.S. Pat. No. 7,259,255). Examples of sequence-dependent protocols useful to isolate homologous promoter regions include, but are not limited to: 1) methods of nucleic acid hybridization; 2) methods of DNA and RNA amplification, as exemplified by various uses of nucleic acid amplification technologies [e.g., polymerase chain reaction ["PCR"], Mullis et al., U.S. Pat. No. 4,683, 202; ligase chain reaction ["LCR"], Tabor, S. et al., *Proc. Acad. Sci. U.S.A.*, 82:1074 (1985); or strand displacement amplification (SDA), Walker, et al., *Proc. Natl. Acad. Sci. U.S.A.*, 89:392 (1992)]; 3) methods of library construction and screening by complementation; and, 4) methods of genome sequencing. Based on sequence conservation between related organisms, one would expect that the promoter regions would likely share significant homology (i.e., at least about 70-85% identity, more preferably at least about 85-90% identity and more preferably at least about 90-95% identity); however, one or more differences in nucleotide sequence could be observed when aligned with promoter regions of comparable length derived from the upstream region of SEQ ID NO:13. For example, one of skill in the art could readily isolate the *Yarrowia* DGAT2 promoter region from any of the various *Y. lipolytica* strains available through the American Type Culture Collection ["ATCC"], including, for example #8661, #8662, #9773, #15586, #16617, #16618, #18942, #18943, #18944, #18945, #20114, #20177, #20182, #20225, #20226, #20228, #20327, #20255, #20287, #20297, #20315, #20320, #20324, #20336, #20341, #20346, #20348, #20363, #20364, #20372, #20373, #20383, #20390, #20400, #20460, #20461, #20462, #20496, #20510, #20628, #20688, #20774, #20775, #20776, #20777, #20778, #20779, #20780, #20781, #20794, #20795, #20875, #20241, #20422, #20423, #32338, #32339, #32340, #32341, #34342, #32343, #32935, #34017, #34018, #34088, #34922, #34922, #38295, #42281, #44601, #46025, #46026, #46027, #46028, #46067, #46068, #46069, #46070, #46330, #46482, #46483, #46484, #46436, #60594, #62385, #64042, #74234, #76598, #76861, #76862, #76982, #90716, #90811, #90812, #90813, #90814, #90903, #90904, #90905, #96028, #201241, #201242, #201243, #201244, #201245, #201246, #201247, #201249, or #201847. Similarly, the following strains of *Yarrowia lipolytica* could be obtained from the Herman J. Phaff Yeast Culture Collection, University of California Davis (Davis, Calif.): *Y. lipolytica* 49-14, *Y. lipolytica* 49-49, *Y. lipolytica* 50-140, *Y. lipolytica* 50-46, *Y. lipolytica* 50-47, *Y. lipolytica* 51-30, *Y. lipolytica* 60-26, *Y. lipolytica* 70-17, *Y. lipolytica* 70-18, *Y. lipolytica* 70-19, *Y. lipolytica* 70-20, *Y. lipolytica* 74-78, *Y. lipolytica* 74-87, *Y. lipolytica* 74-88, *Y. lipolytica* 74-89, *Y. lipolytica* 76-72, *Y. lipolytica* 76-93, *Y. lipolytica* 77-12T and *Y. lipolytica* 77-17. Or, strains could be obtained from the Laboratoire de Microbiologie et Génétique Moléculaire of Dr. Jean-Marc Nicaud, INRA Centre de Grignon, France, including for example, *Yarrowia lipolytica* JMY798 (Mičková, K. et al., *Appl. Environ. Microbiol.* 70(7):3918-24 (2004)), *Y. lipolytica* JMY399 (Barth, G., and C. Gaillardin. In, *Nonconventional Yeasts In Biotechnology*; Wolf, W. K., Ed.; Springer-Verlag: Berlin, Germany, 1996; pp 313-388) and *Y. lipolytica* JMY154 (Wang, H. J., et al., *J. Bacteriol.* 181(17):5140-8 (1999)).

In general, microbial expression systems and expression vectors containing regulatory sequences that direct high level expression of foreign proteins are well known to those skilled in the art. Any of these could be used to construct chimeric genes, which could then be introduced into appropriate microorganisms via transformation to provide high-level expression of the encoded enzymes.

Vectors (e.g., constructs, plasmids) and DNA expression cassettes useful for the transformation of suitable microbial host cells are well known in the art. The specific choice of sequences present in the construct is dependent upon the desired expression products, the nature of the host cell and the proposed means of separating transformed cells versus non-transformed cells. Typically, however, the vector contains at least one expression cassette, a selectable marker and sequences allowing autonomous replication or chromosomal integration. Suitable expression cassettes comprise a region 5' of the gene that controls transcription (e.g., a promoter), the gene coding sequence, and a region 3' of the DNA fragment that controls transcriptional termination, i.e., a terminator. It is most preferred when both control regions are derived from genes from the transformed yeast cell, although they need not be derived from genes native to the host.

Herein, transcriptional control regions (also initiation control regions or promoters) that are useful to drive expression of a coding gene of interest in the desired yeast cell are those promoter regions of a dgat2 *Yarrowia* gene as described supra. Once the promoter regions are identified and isolated, they may be operably linked to a coding region of interest to create a chimeric gene. The chimeric gene may then be expressed in a suitable expression vector in transformed yeast cells, particularly in the cells of oleaginous yeast (e.g., *Yarrowia lipolytica*).

Coding regions of interest to be expressed in transformed yeast cells may be either endogenous to the host or heterologous. Genes encoding proteins of commercial value are particularly suitable for expression. For example, suitable coding regions of interest may include (but are not limited to) those encoding viral, bacterial, fungal, plant, insect, or vertebrate coding regions of interest, including mammalian polypeptides. Further, these coding regions of interest may be, for example, structural proteins, signal transduction proteins, transcription factors, enzymes (e.g., oxidoreductases, transferases, hydrolyases, lyases, isomerases, ligases), or peptides. A non-limiting list includes genes encoding enzymes such as acyltransferases, aminopeptidases, amylases, carbohydrases, carboxypeptidases, catalases, cellulases, chitinases, cutinases, cyclodextrin glycosyltransferases, deoxyribonucleases, esterases, alpha-galactosidases, beta-glucanases, beta-galactosidases, glucoamylases, alpha-glucosidases, beta-glucosidases, invertases, laccases, lipases, mannosidases, mutanases, oxidases, pectinolytic enzymes, peroxidases, phospholipases, phosphatases, phytases, polyphenoloxidases, proteolytic enzymes, ribonucleases, transglutaminases or xylanases.

Thus, one aspect of the present disclosure provides a recombinant construct comprising a *Yarrowia* dgat2 promoter region, as well as recombinant expression vectors comprising the recombinant construct. The dgat2 promoter may also be comprised within a chimeric gene.

Also provided herein is a method for the expression of a coding region of interest in a transformed yeast cell comprising:
  a) providing a transformed yeast cell having a recombinant construct, wherein the recombinant construct comprises:
    (1) a promoter region of a dgat2 *Yarrowia* gene; and
    (2) a coding region of interest which is expressible in the yeast cell;
    wherein the promoter region is operably linked to the coding region of interest; and
  b) growing the transformed yeast cell of step (a) under conditions whereby the recombinant construct is expressed.

The polypeptide so produced by expression of the recombinant construct may optionally be recovered from the culture.

In some embodiments herein, preferred coding regions of interest are those encoding enzymes involved in the production of microbial oils, including omega-6 and omega-3 fatty acids (i.e., omega-6 and omega-3 fatty acid biosynthetic pathway enzymes). Thus, preferred coding regions include those encoding desaturases (e.g., delta-8 desaturases, delta-5 desaturases, delta-17 desaturases, delta-12 desaturases, delta-4 desaturases, delta-6 desaturases, delta-15 desaturases and delta-9 desaturases) and elongases (e.g., $C_{14/16}$ elongases, $C_{16/18}$ elongases, $C_{18/20}$ elongases, $C_{20/22}$ elongases, delta-6 elongases and delta-9 elongases).

More specifically, the omega-3/omega-6 fatty acid biosynthetic pathway is illustrated in FIG. 3. All pathways require the initial conversion of oleic acid [18:1] to linoleic acid ["LA"; 18:2], the first of the omega-6 fatty acids, by a delta-12 desaturase. Then, using the "delta-9 elongase/delta-8 desaturase pathway" and LA as substrate, long-chain omega-6 fatty acids are formed as follows: 1) LA is converted to eicosadienoic acid ["EDA"; 20:2] bp a delta-9 elongase; 2) EDA is converted to dihomo-gamma-linolenic acid ["DGLA"; 20:3] bp a delta-8 desaturase; 3) DGLA is converted to arachidonic acid ["ARA"; 20:4] bp a delta-5 desaturase; 4) ARA is converted to docosatetraenoic acid ["DTA"; 22:4] bp a $C_{20/22}$ elongase; and, 5) DTA is converted to docosapentaenoic acid ["DPAn-6"; 22:5] bp a delta-4 desaturase. To clarify, "omega-6 fatty acids" are polyunsaturated fatty acids having the first unsaturated double bond six carbon atoms from the omega (methyl) end of the molecule and additionally having a total of two or more double bonds, with each subsequent unsaturation occurring 3 additional carbon atoms toward the carboxyl end of the molecule.

The "delta-9 elongase/delta-8 desaturase pathway" can also use alpha-linolenic acid ["ALA"; 18:3] as substrate to produce long-chain omega-3 fatty acids as follows: 1) LA is converted to ALA, the first of the omega-3 fatty acids, by a delta-15 desaturase; 2) ALA is converted to eicosatrienoic acid ["ETrA"; 20:3] by a delta-9 elongase; 3) ETrA is converted to eicosatetraenoic acid ["ETA"; 20:4] by a delta-8 desaturase; 4) ETA is converted to eicosapentaenoic acid ["EPA"; 20:5] by a delta-5 desaturase; 5) EPA is converted to docosapentaenoic acid ["DPA"; 22:5] bp a $C_{20/22}$ elongase; and, 6) DPA is converted to docosahexaenoic acid ["DHA"; 22:6] bp a delta-4 desaturase. Optionally, omega-6 fatty acids may be converted to omega-3 fatty acids. For example, ETA and EPA are produced from DGLA and ARA, respectively, by delta-17 desaturase activity. To clarify, "omega-3 fatty acids" are polyunsaturated fatty acids having the first unsaturated double bond three carbon atoms away from the omega end of the molecule and additionally having a total of three or more double bonds, with each subsequent unsaturation occurring 3 additional carbon atoms toward the carboxyl end of the molecule.

Alternate pathways for the biosynthesis of omega-3/omega-6 fatty acids utilize a delta-6 desaturase and $C_{18/20}$ elongase, that is, the "delta-6 desaturase/delta-6 elongase pathway". More specifically, LA and ALA may be converted to GLA and stearidonic acid ["STA"; 18:4], respectively, by a delta-6 desaturase; then, a $C_{18/20}$ elongase converts GLA to DGLA and/or STA to ETA. Downstream PUFAs are subsequently formed as described above.

One of skill in the art will appreciate that the disclosure herein also provides a method for the production of an omega-3 fatty acid or omega-6 fatty acid comprising:
a) providing a transformed oleaginous yeast comprising a recombinant construct, wherein the recombinant construct comprises:
i) a promoter region of a dgat2 *Yarrowia* gene; and
ii) a coding region encoding at least one omega-3 fatty acid or omega-6 fatty acid biosynthetic pathway enzyme;
wherein the promoter region and the coding region are operably linked; and
b) growing the transformed oleaginous yeast of step (a) under conditions whereby the at least one omega-3 fatty acid or omega-6 fatty acid biosynthetic pathway enzyme is expressed and the omega-3 fatty acid or the omega-6 fatty acid is produced; and
c) optionally recovering the omega-3 fatty acid or the omega-6 fatty acid.

The omega-3 fatty acid or the omega-6 fatty acid may be selected from the group consisting of: LA, GLA, EDA, DGLA, ARA, DTA, DPAn-6, ALA, STA, ETrA, ETA, EPA, DPAn-3 and DHA.

Once a DNA cassette (e.g., comprising a chimeric gene comprising a promoter region of a dgat2 *Yarrowia* gene, ORF and terminator) suitable for expression in a yeast cell has been obtained, it is placed in a plasmid vector capable of autonomous replication in the yeast cell, or it is directly integrated into the genome of the yeast cell. Integration of expression cassettes can occur randomly within the yeast genome or can be targeted through the use of constructs containing regions of homology with the yeast genome sufficient to target recombination to a specific locus. All or some of the transcriptional and translational regulatory regions can be provided by the endogenous locus where constructs are targeted to an endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced chimeric genes are expressed at the necessary levels to provide for synthesis of the desired products.

U.S. Pat. No. 7,259,255 describes means to increase expression of a particular coding region of interest.

Constructs comprising the chimeric gene(s) of interest may be introduced into a yeast cell by any standard technique. These techniques include transformation (e.g., lithium acetate transformation [*Methods in Enzymology*, 194:186-187 (1991)]), protoplast transformation, bolistic impact, electroporation, microinjection, or any other method that introduces the chimeric gene(s) of interest into the yeast cell.

For convenience, a yeast cell that has been manipulated by any method to take up a DNA sequence, for example, in an expression cassette, is referred to herein as "transformed", "transformant" or "recombinant" (as these terms will be used interchangeably herein). The transformed yeast will have at least one copy of the expression construct and may have two or more, depending upon whether the expression cassette is integrated into the genome or is present on an extrachromosomal element having multiple copy numbers.

The transformed yeast cell can be identified by various selection techniques, as described in U.S. Pat. No. 7,238,482, U.S. Pat. No. 7,259,255 and U.S. Pat. No. 7,932,077.

Following transformation, substrates upon which the translated products of the chimeric genes act may be produced by the yeast either naturally or transgenically, or they may be provided exogenously.

Yeast cells for expression of the instant chimeric genes comprising a promoter region of a dgat2 *Yarrowia* gene may include yeast that grow on a variety of feedstocks, including simple or complex carbohydrates, fatty acids, organic acids, oils, glycerol and alcohols, and/or hydrocarbons over a wide range of temperature and pH values. It is contemplated that because transcription, translation and the protein biosynthetic apparatus are highly conserved, any yeast will be a suitable host for expression of the present recombinant constructs.

As previously noted, yeast do not form a specific taxonomic or phylogenetic grouping, but instead comprise a diverse assemblage of unicellular organisms that occur in the Ascomycotina and Basidiomycotina, most of which reproduce by budding (or fission) and derive energy via fermentation processes. Examples of some yeast genera include, but are not limited to: *Agaricostilbum, Ambrosiozyma, Arthroascus, Arxula, Ashbya, Babjevia, Bensingtonia, Botryozyma, Brettanomyces, Bullera, Candida, Clavispora, Cryptococcus, Cystofilobasidium, Debaryomyces, Dekkera, Dipodascus, Endomyces, Endomycopsella, Erythrobasidium, Fellomyces, Filobasidium, Galactomyces, Geotrichum, Guilliermondella, Hansenula, Hanseniaspora, Kazachstania, Kloeckera, Kluyveromyces, Kockovaella, Kodamaea, Komagataella, Kondoa, Lachancea, Leucosporidium, Leucosporidiella, Lipomyces, Lodderomyces, Issatchenkia, Magnusiomyces, Mastigobasidium, Metschnikowia, Monosporella, Myxozyma, Nadsonia, Nematospora, Oosporidium, Pachysolen, Pichia, Phaffia, Pseudozyma, Reniforma, Rhodosporidium, Rhodotorula, Saccharomyces, Saccharomycodes, Saccharomycopsis, Saturnispora, Schizoblastosporion, Schizosaccharomyces, Sirobasidium, Smithiozyma, Sporobolomyces, Sporopachydermia, Starmerella, Sympodiomycopsis, Sympodiomyces, Torulaspora, Tremella, Trichosporon, Trichosporiella, Trigonopsis, Udeniomyces, Wickerhamomyces, Williopsis, Xanthophyllomyces, Yarrowia, Zygosaccharomyces, Zygotorulaspora, Zymoxenogloea* and *Zygozyma*.

In preferred embodiments, the transformed yeast is an oleaginous yeast. These organisms are naturally capable of oil synthesis and accumulation, wherein the oil can comprise greater than about 25% of the dry cell weight, more preferably greater than about 30% of the dry cell weight, more preferably greater than about 40% of the dry cell weight, more preferably greater than about 50% of the dry cell weight, and most preferably greater than about 60% of the dry cell weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*). Alternately, oil biosynthesis may be genetically engineered such that the transformed yeast can produce more than 25% oil of the dry cell weight, and thereby be considered oleaginous.

Most preferred is the oleaginous yeast *Yarrowia lipolytica*. In a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.*, 82(1):43-9 (2002)). The *Y. lipolytica* strain designated as ATCC #20362 was the particular strain from which the dgat2 *Yarrowia* gene and promoter regions encompassed within SEQ ID NO:13 were isolated.

Specific teachings applicable for transformation of oleaginous yeasts (i.e., *Yarrowia lipolytica*) via integration techniques based on linearized fragments of DNA include U.S. Pat. No. 4,880,741 and U.S. Pat. No. 5,071,764 and Chen, D. C. et al. (*Appl. Microbiol. Biotechnol.*, 48(2):232-235 (1997)). Specific teachings applicable for expression of omega-3 fatty acid or omega-6 fatty acid biosynthetic pathway enzymes in the oleaginous yeast *Y. lipolytica* are described in U.S. Pat. No. 7,238,482, U.S. Pat. No. 7,550,286, U.S. Pat. No. 7,588,931, U.S. Pat. No. 7,932,077, U.S. Pat. Appl. Publ. No. 2009-0093543-A1, and U.S. Pat. Appl. Publ. No. 2010-0317072-A1, each incorporated herein by reference in their entirety.

The transformed yeast cell is grown under conditions that optimize expression of the chimeric gene(s). In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Microorganisms of interest, such as oleaginous yeast (e.g., *Yarrowia lipolytica*) are generally grown in a complex medium such as yeast extract-peptone-dextrose broth ["YPD"] or a defined minimal media that lacks a component necessary for growth and thereby forces selection of the desired expression cassettes (e.g., Yeast Nitrogen Base (DIFCO Laboratories, Detroit, Mich.)).

Fermentation media suitable for the transformed yeast described herein should contain a suitable carbon source. Suitable carbon sources may include, but are not limited to: monosaccharides, disaccharides, oligosaccharides, polysaccharides, sugar alcohols, mixtures from renewable feedstocks, alkanes, fatty acids, esters of fatty acids, glycerol, monoglycerides, diglycerides, triglycerides, phospholipids, various commercial sources of fatty acids, and one-carbon sources, such as are described in U.S. Pat. No. 7,259,255. Hence it is contemplated that the source of carbon utilized may encompass a wide variety of carbon-containing sources and will only be limited by the choice of the yeast species. Although all of the above mentioned carbon sources and mixtures thereof are expected to be suitable herein, preferred carbon sources are sugars (e.g., glucose, invert sucrose, sucrose, fructose and combinations thereof), glycerols, and/or fatty acids (see U.S. Pat. Appl. Publ. No. 2011-0059204 A1).

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the transformed yeast (and optionally, promotion of the enzymatic pathways necessary for omega-3/omega-6 fatty acid production). Particular attention is given to several metal ions, such as $Fe^{+2}$, $Cu^{+2}$, $Mn^{+2}$, $Co^{+2}$, $Zn^{+2}$ and $Mg^{+2}$, that promote synthesis of lipids and PUFAs (Nakahara, T. et al., *Ind. Appl. Single Cell Oils*, D. J. Kyle and R. Colin, eds. pp 61-97 (1992)).

Preferred growth media for the methods and transformed yeast cells described herein are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of omega-3/omega-6 fatty acids in oleaginous yeast cells requires a two-stage process, since the metabolic state must be "balanced"

between growth and synthesis/storage of fats. Thus, most preferably, a two-stage fermentation process is necessary for the production of omega-3/omega-6 fatty acids in oleaginous yeast (e.g., *Yarrowia lipolytica*). This approach is described in U.S. Pat. No. 7,238,482.

Host cells comprising a suitable coding region of interest operably linked to promoter regions of a dgat2 *Yarrowia* gene may be cultured using methods known in the art. For example, the cell may be cultivated by shake flask cultivation or small-/large-scale fermentation in laboratory or industrial fermentors performed in a suitable medium and under conditions allowing expression of the coding region of interest. Similarly, where commercial production of a product that relies on the instant genetic chimera is desired, a variety of culture methodologies may be applied. For example, large-scale production of a specific gene product over-expressed from a recombinant host may be produced by a batch, fed-batch or continuous fermentation process (see U.S. Pat. No. 7,259,255).

EXAMPLES

The present invention is further described in the following Examples, which illustrate reductions to practice of the invention but do not completely define all of its possible variations.

General Methods

Standard recombinant DNA and molecular cloning techniques used in the Examples are well known in the art and are described by: 1) Sambrook, J., Fritsch, E. F. and Maniatis, T., *Molecular Cloning: A Laboratory Manual*; Cold Spring Harbor Laboratory: Cold Spring Harbor, N.Y. (1989) (Maniatis); 2) T. J. Silhavy, M. L. Bennan, and L. W. Enquist, Experiments with Gene Fusions; Cold Spring Harbor Laboratory: Cold Spring Harbor, N.Y. (1984); and 3) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, 2$^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), New England Biolabs (Ipswich, Mass.), or Sigma Chemical Company (St. Louis, Mo.), unless otherwise specified. *E. coli* strains were typically grown at 37° C. on Luria Bertani ["LB"] plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "pmole" mean micromole(s), "g" means gram(s), "µg" means microgram(s), "ng" means nanogram(s), "U" means unit(s), "bp" means base pair(s) and "kB" means kilobase(s).

Nomenclature for Expression Cassettes:

The structure of an expression cassette will be represented by a simple notation system of "X::Y::Z", wherein X describes the promoter fragment, Y describes the gene fragment, and Z describes the terminator fragment, which are all operably linked to one another.

Transformation and Cultivation of *Yarrowia lipolytica*:

*Y. lipolytica* strains with ATCC Accession Nos. #20362, #76982 and #90812 were purchased from the American Type Culture Collection (Rockville, Md.). *Y. lipolytica* strains were typically grown at 28-30° C. Agar plates were prepared as required by addition of 20 g/L agar to the liquid media, according to standard methodology.

Example 1

Isolation of the 5' Upstream Regions of the DGAT2 Gene from *Yarrowia lipolytica*

According to the DNA sequence of the *Yarrowia lipolytica* DGAT2 gene (YALI0E32769g locus, *Yarrowia* chromosome E sequence from 3886857 to 3888401, Dujon, B. et al., *Nature*, 430(6995):35-44 (2004), SEQ ID NO:36), the 1 kB length sequence 5' upstream of the nucleotide 'A' (designated as +1) of the translation initiation codon 'ATG' was assumed to encode the promoter region (designated herein as DGAT2F; SEQ ID NO:13).

To study the promoter region upstream of the DGAT2 gene, oligonucleotides Y1189 (SEQ ID NO:14) and Y1191 (SEQ ID NO:15) were designed as primers to amplify a 966 bp 5' upstream fragment from the nucleotide 'A' of the translation initiation codon 'ATG' of the DGAT2 gene. A ClaI site was included at the 5' portion of oligonucleotide Y1189 (SEQ ID NO:14). In order to incorporate a *Yarrowia* translation initiation site consensus sequence (i.e., ACC<u>ATG</u>G, U.S. Pat. No. 7,125,672) around the start codon 'ATG', the thymine nucleotide ['T'] at position −1 of the DGAT2 gene was mutated to a cytosine ['C'] in oligonucleotide Y1191 (SEQ ID NO:15).

Similarly, oligonucleotide Y1190 (SEQ ID NO:16) and Y1191 (SEQ ID NO:15) were designed as primers to amplify a 484 bp 5' upstream fragment from the nucleotide 'A' of the translation initiation codon 'ATG' of the DGAT2 gene. A ClaI site was also incorporated into the 5' portion of oligonucleotide Y1190 (SEQ ID NO:16).

The 966 bp and 484 bp 5' upstream fragments of the DGAT2 gene were individually amplified using *Yarrowia lipolytica* strain ATCC #20362 genomic DNA as template and either primer pair YL1189 and YL1191 or primer pair YL1190 and YL1191, respectively. The PCR amplification was carried out in a 50 µl total volume comprising: PCR buffer (containing 10 mM KCl, 10 mM (NH$_4$)$_2$SO$_4$, 20 mM Tris-HCl (pH 8.75), 2 mM MgSO$_4$, 0.1% Triton X-100), 100 µg/mL BSA (final concentration), 200 µM each deoxyribonucleotide triphosphate, 10 pmole of each primer and 1 µl of Pfu DNA polymerase (Stratagene, San Diego, Calif.). The thermocycler conditions were set for 35 cycles at 95° C. for 1 min, 56° C. for 30 sec, and 72° C. for 1 min, followed by a final extension at 72° C. for 10 min.

The PCR products comprising the 966 bp and 484 bp 5' upstream fragments of the DGAT2 gene were purified using a Qiagen PCR purification kit, followed by gel electrophoresis in 1% (weight/volume) agarose. Products were then cloned into the pCR4TOPO vector (Invitrogen, San Diego, Calif.). The ligated DNA samples were used to transform *E. coli* DH5a cells individually, and transformants were selected on LB agar containing ampicillin (100 μg/mL).

Analyses of the plasmid DNA from two different transformants confirmed the presence of 966 bp or 484 bp fragments, respectively. The plasmid containing the 966 bp DNA fragment was designated as pT-DG2LPro (SEQ ID NO:17), while the plasmid containing the 484 bp DNA fragment was designated as pT-DG2SPro (SEQ ID NO:18). Sequence analyses showed that pT-DG2LPro and pT-DG2SPro contained fragments of 966 bp (designated as DGAT2L, wherein the "L" is for "long"; SEQ ID NO:19) and of 484 bp (designated as 484 bp DGAT2S, wherein the "S" is for "short"; SEQ ID NO:8) 5' upstream sequence of the DGAT2 gene, respectively. The fragments were flanked by PmeI (from the vector) and NcoI restriction enzyme sites.

Example 2

Modifications to DGAT2L: Creation of Promoters 966 bp DGAT2LM and 965 bp DGAT2L+Pme The present Example describes the synthesis of pT-DGAT2LPro-(-N) and pT-DGAT2LPro-P plasmids, each comprising a modified DGAT2L promoter based on removal or insertion of a specific restriction enzyme site, respectively.

Specifically, plasmid pT-DGAT2LPro-(-N) (SEQ ID NO:20) was generated by site-directed mutagenesis using plasmid pT-DGAT2LPro (Example 1) as template, and oligonucleotides Y1192 (SEQ ID NO:21) and Y1193 (SEQ ID NO:22) as primers. The internal NcoI site (i.e., CCATGG at nucleotides 198-203 of SEQ ID NO:19) of the DGAT2L promoter was mutated into CCAcGG in plasmid pT-DGAT2LPro-(-N) (SEQ ID NO:20). The modified DGAT2L promoter lacking the internal NcoI site within plasmid pT-DGAT2LPro-(-N) was designated as 966 bp DGAT2LM (wherein the "LM" is for "long, modified"; SEQ ID NO:4).

Plasmid pT-DGAT2LPro-P (SEQ ID NO:23) was generated by site-directed mutagenesis using plasmid pT-DGAT2LPro (Example 1) as template, and oligonucleotides Y1220 (SEQ ID NO:24) and Y1221 (SEQ ID NO:25) as primers. Nucleotides 237-245 (i.e., GTTTTTTTC) of the DGAT2L promoter were mutated into GTTTaaaC in pT-DGAT2LPro-P (SEQ ID NO:23), thereby introducing an internal PmeI site within the DGAT2L promoter. The modified DGAT2L promoter comprising the new PmeI site within plasmid pT-DGAT2LPro-P was designated as 965 bp DGAT2L+Pme (SEQ ID NO:26).

Example 3

Synthesis and Transformation of Expression Plasmids Comprising 966 bp DGAT2LM, 722 bp DGAT2M and 484 bp DGAT2S Promoters To perform comparative studies investigating the promoter activity of DGAT2 promoters having lengths of 966 bp, 722 bp or 484 bp, a series of expression plasmids were created such that each DGAT2 promoter was operably linked to a reporter gene (i.e., the *E. coli* gene encoding β-glucuronidase ("GUS"; Jefferson, R. A., *Nature*, 342(6251):837-838 (1989)).

U.S. Pat. No. 7,202,356 describes the synthesis of pDMW212 (FIG. 4A and SEQ ID NO:35 herein), comprising a chimeric FBA::GUS::XPR2 gene. More specifically, this expression cassette comprises an FBA promoter fragment (i.e., 5' upstream untranslated region in front of the 'ATG' translation initiation codon of a fructose-bisphosphate aldolase enzyme [E.G. 4.1.2.13] encoded by the fba1 gene and that is necessary for expression), a GUS reporter gene fragment and an XPR2 terminator fragment (comprising ~100 bp of the 3' region of the *Yarrowia* Xpr gene (Gen Bank Accession No. M17741)), which are all operably linked to one another.

The PmeI/NcoI fragment of pDMW212 (comprising the FBA promoter within the chimeric FBA::GUS::XPR2 gene) was replaced individually with promoters derived from DGAT2 of variant lengths. Specifically, the PmeI/NcoI fragment of pT-DGAT2LPro-(-N) (Example 2), comprising the 966 bp DGAT2LM promoter, was ligated with the PmeI/NcoI linearized pDMW212 fragment, thereby creating plasmid pDG2LGUS (FIG. 4B; SEQ ID NO:3) comprising a chimeric DGAT2LM::GUS::XPR2 gene. Thus, pDG2LGUS contains the following components:

TABLE 3

Description of Plasmid pDG2LGUS

| RE Sites and Nucleotide position in SEQ ID NO: 3 | Description of Fragment and Chimeric Gene Components |
|---|---|
| ClaI/SacI (22-3009) | 966 bp DGAT2LM::GUS::XPR, comprising: 966 bp DGAT2LM promoter: 966 bp *Y. lipolytica* DGAT2LM promoter (SEQ ID NO: 4); GUS: *E. coli* beta-D-glucuronidase (GenBank Accession No. AAA68923); XPR2: ~100 bp of the 3' region of Xpr gene of *Y. lipolytica* (GenBank Accession No. M17741) |
| 4149-3296 | ColE1 plasmid origin of replication |
| 5079-4219 | Ampicillin-resistance gene (Amp$^R$) for selection in *E. coli* |
| EcoRI/SphI (5909-7255) | ARS18: *Y lipolytica* centromere and autonomously replication sequence 18 (GenBank Accession No. M91600) |
| PmeI/SphI (7255-9499) | Leu2: beta-isopropylmalate dehydrogenase gene of *Y. lipolytica* (GenBank Accession No. M37309) |

In a similar manner, the 722 bp PmeI/NcoI fragment of pT-DGAT2LPro-P (Example 2), comprising nucleotides 244-965 of the 965 bp DGAT2L+Pme promoter, was ligated with the PmeI/NcoI linearized pDMW212 fragment, thereby creating plasmid pDG2MGUS (SEQ ID NO:5) comprising a chimeric 722 bp DGAT2M::GUS::XPR2 gene (wherein the "M" in DGAT2M promoter is for "medium"; SEQ ID NO:6).

Lastly, the PmeI/NcoI fragment of pT-DG2SPro (Example 1), comprising the 484 bp DGAT2S promoter, was ligated with the PmeI/NcoI linearized pDMW212 fragment, thereby creating plasmid pDG2SGUS (SEQ ID NO:7) comprising a chimeric 484 bp DGAT2S::GUS::XPR2 gene.

Thus, pDG2LGUS (SEQ ID NO:3), pDG2MGUS (SEQ ID NO:5) and pDG2SGUS (SEQ ID NO:7) are identical expression constructs, with the exception that either a 966 bp DGAT2LM (SEQ ID NO:4), 722 bp DGAT2M (SEQ ID NO:6) or 484 bp DGAT2S (SEQ ID NO:8) promoter derived from the 5' upstream region of the *Yarrowia lipolytica* DGAT2 gene was operably linked to the GUS reporter gene.

*Y. lipolytica* strain Y4001 has been described in U.S. Pat. No. 7,709,239 (Example 3 therein). Strain Y4001, derived from *Y. lipolytica* ATCC #20362, was capable of producing about 17% eicosadienoic acid ["EDA"; 20:2 omega-6] relative to the total lipids. The final genotype of strain Y4001 with respect to wild type *Y. lipolytica* ATCC #20362 was: Leu-, GPD::FmD12::Pex20, EXP1::EgD9e::Lip1, FBAINm:: EgD9eS::Lip2 and YAT1::ME3S::Pex16. Abbreviations are as follows: FmD12 is a *Fusarium moniliforme* delta-12 desaturase gene [U.S. Pat. No. 7,504,259]; ME3S is a codon-optimized C$_{16/18}$ elongase gene, derived from *Mortierella alpina* [U.S. Pat. No. 7,470,532]; EgD9e is a *Euglena gracilis* delta-9 elongase gene [U.S. Pat. No. 7,645,604]; and, EgD9eS is a codon-optimized delta-9 elongase gene, derived from *E. gracilis* [U.S. Pat. No. 7,645,604].

Plasmids pDG2LGUS, pDG2MGUS and pDG2SGUS were transformed separately into *Y. lipolytica* strain Y4001 according to the method of Chen, D.C. et al. (*Appl. Microbiol. Biotechnol.*, 48(2):232-235 (1997)) and as described in U.S. Pat. No. 7,709,239.

Transformed cells were plated onto Minimal Media ["MM"] plates lacking leucine and maintained at 30° C. for 2 to 3 days (Minimal Media comprises per liter: 20 g glucose, 1.7 g yeast nitrogen base without amino acids, 1.0 g proline, and pH 6.1 (do not need to adjust)). Thus, transformants were obtained comprising pDG2LGUS, pDG2MGUS and pDG2SGUS plasmids, respectively.

Example 4

Comparative Analyses of 966 bp DGAT2LM, 722 bp DGAT2M and 484 bp DGAT2S Promoter Activities in *Yarrowia lipolytica* Strain Y4001

The promoter activities of the 966 bp DGAT2LM (SEQ ID NO:4), 722 bp DGAT2M (SEQ ID NO:6) and 484 bp DGAT2S (SEQ ID NO:8) promoters were determined in *Yarrowia* transformants containing plasmids pDG2LGUS, pDG2MGUS and pDG2SGUS, respectively, based on expression of the GUS reporter gene as measured by histochemical assays (Jefferson, R. A., *Plant Mol. Biol. Reporter*, 5:387-405 (1987)).

Specifically, *Y. lipolytica* transformants containing plasmids pDG2LGUS, pDG2MGUS and pDG2SGUS were grown from single colonies in 3 mL MM at 30° C. for 2 days. Then, 1 mL of cells was collected by centrifugation. The remaining cultures were centrifuged and washed 2 times with High Glucose Media ["HGM"], resuspended in 3 mL each of HGM and allowed to grow at 30° C. for another 5 days (HGM comprises per liter: 80 g glucose, 2.58 g KH$_2$PO$_4$ and 5.36 g K$_2$HPO$_4$, pH 7.5 (do not need to adjust)). Cell samples from cultures grown 2 days in MM, as well as cultures grown 2 days in MM and 5 days in HGM were collected by centrifugation, resuspended in 100 µl of histochemical staining buffer, and incubated at 30° C. Staining buffer was prepared by dissolving 5 mg of 5-bromo-4-chloro-3-indolyl glucuronide ["X-Gluc"] in 50 µl dimethyl formamide, followed by the addition of 5 mL 50 mM NaPO$_4$, pH 7.0.

The results (FIG. 5) of histochemical staining showed that the 966 bp DGAT2LM, 722 bp DGAT2M and 484 bp DGAT2S promoters, in constructs pDG2LGUS, pDG2MGUS and pDG2SGUS, respectively, were each active. Comparable strong constitutive expression was observed in *Yarrowia* strains growing either in MM or in nitrogen-limited HGM media.

Based on the above results, one of skill in the art would recognize that the DGAT2LM promoter set forth as SEQ ID NO:4 can be truncated and retain promoter activity. Deleting the region defined by nucleotide positions 1 to 244 of SEQ ID NO:4 resulted in the active mutant promoter described herein as 722 bp DGAT2M, while deleting the region defined by nucleotide positions 1 to 482 of SEQ ID NO:4 resulted in the active mutant promoter described herein as 484 bp DGAT2S (FIG. 1). It is therefore assumed that a variety of modified DGAT2LM promoters could be utilized for expression of a coding region of interest in a *Yarrowia* host cell, wherein the promoter optionally comprises at least one modification selected from the group consisting of: a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481 or 482 consecutive nucleotides, wherein the first nucleotide deleted is the cytosine nucleotide ['C'] at position 1 of SEQ ID NO:4.

Although all of the 5'-truncated promoters derived from the DGAT2LM promoter (SEQ ID NO:4) will comprise a thymine ['T'] to cytosine ['C'] substitution at the nucleotide position corresponding to the −1 position of SEQ ID NO:36 (when the position corresponding to the 'A' nucleotide of the 'ATG' translation initiation site of the DGAT2 gene is considered +1), when compared to the wildtype 5' upstream sequence, one of skill in the art will appreciate that a suitable promoter region of a dgat2 *Yarrowia* gene may optionally comprise a thymine ['T'] or a cytosine ['C'] nucleotide at position −1. Alternately, the modified DGAT2 promoter may also tolerate substitution of an adenine ['A'] nucleotide or guanine ['G'] nucleotide for the wildtype thymine ['T'] at position −1.

Additionally, it is to be noted that SEQ ID NO:4, compared to SEQ ID NO:19, comprises a substitution of a cytosine ['C'] nucleotide for a thymine ['T'] nucleotide at position 201; thus modified DGAT2 promoters may also tolerate substitution of an adenine ['A'] nucleotide or guanine ['G'] nucleotide for the wildtype thymine ['T'] at this position.

Example 5

Synthesis and Transformation of Expression Plasmids pDG2SP2GUS and pDG2SP4GUS Comprising 334 bp DGAT2SP2 and 256 bp DGAT2SP4 Promoters

To perform comparative studies investigating the promoter activity of modified DGAT2 promoters having lengths of 334 bp or 256 bp, expression plasmids pDG2SP2GUS and pDG2SP4GUS were created, respectively, each comprising a modified DGAT2 promoter operably linked to the GUS reporter gene.

First, site-directed mutagenesis was performed using pDG2SGUS (Example 3) as template and oligonucleotides Y2160 (SEQ ID NO:27) and Y2161 (SEQ ID NO:28) as primers. Specifically, primer Y2160 was designed to insert four nucleotides (i.e., TTTA) between nucleotides 150 and 151 of SEQ ID NO:8, thereby resulting in creation of a PmeI site in a 5' portion of the 484 bp DGAT2S promoter in the resultant plasmid, pDG2SGUS-P (SEQ ID NO:29). Plasmid pDG2SGUS-P was then digested with PmeI, and the large PmeI fragment of pDG2SGUS-P was isolated and self-ligated to generate pDG2SP2GUS (SEQ ID NO:9). The DGAT2 promoter fragment in pDG2SP2GUS was 334 bp in length and designated as 334 bp DGAT2SP2 (SEQ ID NO:10).

Similarly, site-directed mutagenesis was performed using pDG2SGUS (Example 3) as template and oligonucleotides Y2164 (SEQ ID NO:31) and Y2165 (SEQ ID NO:32) as primers. Primer Y2164 was designed to insert three nucleotides (i.e., TTT) between nucleotides 228 and 229 of SEQ ID NO:8, thereby resulting in creation of a PmeI site in a 5' portion of the 484 bp DGAT2S promoter in the resultant plasmid, pDG2SGUS-P3 (SEQ ID NO:30). Plasmid pDG2SGUS-P3 was then digested with PmeI, and the large PmeI fragment of pDG2SGUS-P3 was isolated and self-ligated to generate pDG2SP4GUS (SEQ ID NO:11). The DGAT2 promoter fragment in pDG2SP4GUS was 256 bp in length, and was designated as 256 bp DGAT2SP4 (SEQ ID NO:12).

Thus, pDG2SGUS (SEQ ID NO:7; Example 3), pDG2SP2GUS (SEQ ID NO:9) and pDG2SP4GUS (SEQ ID NO:11) are identical expression constructs, with the exception that either a 484 bp DGAT2S (SEQ ID NO:8), 334 bp DGAT2SP2 (SEQ ID NO:10) or 256 bp DGAT2SP4 (SEQ ID NO:12) promoter derived from the 5' upstream region of the *Yarrowia lipolytica* DGAT2 gene was operably linked to the chimeric GUS::XPR2 gene.

Plasmids pDG2SGUS, pDG2SP2GUS and pDG2SP4GUS were transformed separately into *Y. lipolytica* strain Y4001 as described in Example 3. Transformant cells were plated onto MM plates lacking leucine and maintained at 30° C. for 2 to 3 days. Thus, transformants were obtained comprising pDG2SGUS, pDG2SP2GUS and pDG2SP4GUS plasmids, respectively.

Example 6

**Comparative Analysis of 484 bp DGAT2S, 334 bp DGAT2SP2 and 256 DGAT2SP4 Promoter Activities in *Yarrowia lipolytica* Strain Y4001**

The promoter activities of the 484 bp DGAT2S (SEQ ID NO:8), 334 bp DGAT2SP2 (SEQ ID NO:10) and 256 bp DGAT2SP4 (SEQ ID NO:12) promoters were determined in *Yarrowia* transformants containing pDG2SGUS, pDG2SP2GUS, and pDG2SP4GUS, respectively. GUS activity in each expressed construct was measured by histochemical assays as described in Example 4.

The results of histochemical staining showed that the promoter activities of 334 bp DGAT2SP2 (SEQ ID NO:10) and 256 bp DGAT2SP4 (SEQ ID NO:12) functioned with about 70% and 30% of the activity of the 484 bp DGAT2S (SEQ ID NO:8) promoter, respectively. Like the DGAT2S promoter, the DGAT2SP2 and DGAT2SP4 promoters were active when *Yarrowia* was growing in both MM and in nitrogen-limited HGM media.

Based on the above results, one of skill in the art will recognize that the DGAT2LM promoter set forth as SEQ ID NO:4 can be further truncated (i.e., beyond the region defined by nucleotide positions 1 to 482, as demonstrated in Example 4) and retain promoter activity. Specifically, deleting the region defined by nucleotide positions 1 to 632 of SEQ ID NO:4 resulted in the active mutant promoter described herein as 334 bp DGAT2SP2, while deleting the region defined by nucleotide positions 1 to 710 of SEQ ID NO:4 resulted in the active mutant promoter described herein as 256 bp DGAT2SP4 (FIG. 1). It is therefore assumed that a variety of modified DGAT2LM promoters could be utilized for expression of a coding region of interest in a *Yarrowia* host cell, wherein the promoter optionally comprises at least one modification selected from the group consisting of: a deletion at the 5'-terminus of 1 to 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709 or 710 consecutive nucleotides, wherein the first nucleotide deleted is the cytosine nucleotide ['C'] at position 1 of SEQ ID NO:4.

FIGS. 2A, 2B and 2C is an alignment of the following *Y. lipolytica* DGAT2 promoter regions described herein: the *Y. lipolytica* DGAT2F (SEQ ID NO:13) promoter region, which is the 1000 bp 5' upstream sequence (i.e., the −1000 to −1 region) of the *Y. lipolytica* DGAT2, wherein the nucleotide 'A' of the DGAT2 translation initiation codon 'ATG' was designated as +1; the 966 bp DGAT2L (SEQ ID NO:19) promoter region; the 966 bp DGAT2LM (SEQ ID NO:4) promoter region; the 484 bp DGAT2S (SEQ ID NO:8) promoter region; the 334 bp DGAT2SP2 (SEQ ID NO:10) promoter region; and the 256 bp DGAT2SP4 (SEQ ID NO:12) promoter region. Sequence differences are noted with an arrow over the alignment and a box.

All of the modified promoters derived from the DGAT2F promoter set forth as SEQ ID NO:13 (i.e., 966 bp DGAT2L, 966 bp DGAT2LM, 484 bp DGAT2S, 334 bp DGAT2SP2 and 256 bp DGAT2SP4) comprise a thymine ['T'] to cytosine ['C'] substitution at the nucleotide corresponding to position −1 in SEQ ID NO:36. One of skill in the art will appreciate that a suitable promoter region of a dgat2 Yarrowia gene may optionally comprise a thymine ['T'] or a cytosine ['C'] nucleotide at position −1; alternately, the modified DGAT2 promoter may also tolerate substitution of an adenine ['A'] nucleotide or guanine ['G'] nucleotide for the wildtype thymine ['T'] at position −1.

Additionally, it is to be noted that SEQ ID NO:10, compared to SEQ ID NO:19, comprises a substitution of an adenine ['A'] nucleotide for a guanine ['G'] nucleotide at position 632; thus modified DGAT2 promoters may also tolerate substitution of a thymine ['T'] nucleotide or a cytosine ['C'] nucleotide for the wildtype guanine ['G'] at this position.

Example 7

Sequence Analysis of Promoter Regions of a dgat2 Yarrowia Gene

The present Example describes the lack of a TATA-box within promoter regions of the dgat2 Yarrowia gene.

Although promoters interact with the TATA binding protein ["TBP"] to create a transcription initiation complex from which RNA polymerase II transcribes the DNA coding sequence, only some promoters contain a TATA box to which TBP binds directly while other promoters are TATA-less promoters. The "TATA box" or "Goldberg-Hogness box" is a DNA sequence (i.e., cis-regulatory element) found in the promoter region of some genes in archaea and eukaryotes. For example, approximately 24% of human genes contain a TATA box within the core promoter (Yang C, et al., Gene, 389:52-65 (2007)); phylogenetic analysis of six Saccharomyces species revealed that about 20% of the 5,700 yeast genes contained a TATA-box element (Basehoar et al., Cell, 116: 699-709 (2004)). The TATA box has a core DNA sequence of 5'-TATAAA-3' or a variant thereof and is usually located ~200 to 25 base pairs upstream of the transcriptional start site. The transcription initiation complex forms at the site of the TATA box (Smale and Kadonaga, Annual Review Of Biochemistry, 72:449-479 (2003)). This complex comprises the TATA binding protein, RNA polymerase II, and various transcription factors (i.e., TFIID, TFIIA, TFIIB, TFIIF, TFIIE and TFIIH). Both the TATA box itself and the distance between the TATA box and transcription start site affect activity of TATA box-containing promoters in eukaryotes (Zhu et al., The Plant Cell, 7:1681-1689 (1995)).

The genes within Yarrowia can be largely classified into three classes according to their promoter sequences. Specifically, the first class of genes includes those comprising a TATA box, usually, ~130 to 20 base pairs upstream of the gene's transcription start site. The second class of genes includes those comprising an initiator element(s) around the gene's transcription start site. And, the third class of genes lacks both a TATA box and initiator element in the gene's promoter region.

Analysis of the sequence of the 256 bp DGAT2SP4 promoter region (Examples 6 and 7; SEQ ID NO:12) revealed that the promoter region does not contain a typical TATA-box. However, two possible initiator elements were identified within a 51 bp sequence of the DGAT2SP4 promoter region (corresponding to nucleotides 118-169 of SEQ ID NO:12, which is equivalent to the −138 to −87 region upstream of the 'ATG' translation initiation codon of the dgat2 gene). Based on identification of this 51 bp fragment, it is believed that a suitable minimal dgat2 promoter region for basal level transcription initiation would comprise this fragment, set forth herein as SEQ ID NO:33. It is also hypothesized that the 138 base pair sequence (i.e., set forth as SEQ ID NO:34) spanning the −138 to −1 region upstream of the 'ATG' translation initiation codon of the dgat2 gene would be suitable for basal level transcription initiation.

Example 8

Comparison of Various Yarrowia DGAT2 Promoter Regions

The present Example summarizes the relative activity of various dgat2 promoter regions exemplified in Examples 1-6.

It was concluded that the DGAT2 promoter is a very strong constitutive promoter that can be used to drive high level expression of various genes in engineered Yarrowia strains, as shown in Table 4 below.

TABLE 4

Summary of Relative Activity of Various DGAT2 Promoter Regions

| Construct Comprising GUS Reporter | Promoter Operably Linked to GUS Reporter | Promoter Length | Promoter Activity Cultured in MM* | Promoter Activity Cultured in MM + HGM** |
|---|---|---|---|---|
| pDG2LGUS (SEQ ID NO: 3) | DGAT2LM (SEQ ID NO: 4) | 966 bp | +++ | +++ |
| pDG2MGUS (SEQ ID NO: 5) | DGAT2M (SEQ ID NO: 6) | 722 bp | +++ | +++ |
| pDG2SGUS (SEQ ID NO: 7) | DGAT2S (SEQ ID NO: 8) | 484 bp | +++ | +++ |
| pDG2SP2GUS (SEQ ID NO: 9) | DGAT2SP2 (SEQ ID NO: 10) | 334 bp | ++ | ++ |
| pDG2SP4GUS (SEQ ID NO: 11) | DGAT2SP4 (SEQ ID NO: 12) | 256 bp | + | + |

*Cultured in MM refers to 2 days growth in MM.
**Cultured in MM + HGM refers to 2 days growth in MM, followed by 3 days growth in HGM.

What is claimed is:

1. A method for expressing a coding region of interest in a transformed yeast cell comprising:
   a) providing a transformed yeast cell having a recombinant construct, wherein the recombinant construct comprises:
      (1) a promoter region comprising SEQ ID NO:19, SEQ ID NO:4, SEQ ID NO:6, SEQ ID NO:8, SEQ ID NO:10, or SEQ ID NO:12; and
      (2) a coding region of interest which is expressible in the yeast cell; wherein the promoter region is operably linked to the coding region of interest; and
   b) growing the transformed yeast cell of step (a) under conditions whereby the recombinant construct of step (a) is expressed.

2. The method according to claim 1, wherein the promoter region comprises SEQ ID NO:19.

3. The method according to claim 1, wherein the promoter region comprises SEQ ID NO:4, SEQ ID NO:6, SEQ ID NO:8, or SEQ ID NO:10.

4. The method according to claim 1, wherein the promoter region comprises SEQ ID NO:12.

5. The method according to claim 1, wherein the transformed yeast cell is an oleaginous yeast cell.

6. The method of claim 5, wherein the oleaginous yeast cell is a member of a genus selected from the group consisting of *Yarrowia, Candida, Rhodotorula, Rhodosporidium, Cryptococcus, Trichosporon* and *Lipomyces*.

7. The method according to claim 1, wherein the coding region of interest encodes a polypeptide, wherein the polypeptide is selected from the group consisting of: desaturases, elongases, acyltransferases, aminopeptidases, amylases, carbohydrases, carboxypeptidases, catalases, cellulases, chitinases, cutinases, cyclodextrin glycosyltransferases, deoxyribonucleases, esterases, alpha-galactosidases, beta-galactosidases, glucoamylases, alpha-glucosidases, beta-glucanases, beta-glucosidases, invertases, laccases, lipases, mannosidases, mutanases, oxidases, pectinolytic enzymes, peroxidases, phospholipases, phosphatases, phytases, polyphenoloxidases, proteolytic enzymes, ribonucleases, transglutaminases and xylanases.

8. The method according to claim 1, wherein the coding region encodes at least one omega-3 fatty acid or omega-6 fatty acid biosynthetic pathway enzyme, and wherein an omega-3 fatty acid or omega-6 fatty acid is produced in step (b).

9. The method according to claim 8, wherein the omega-3 fatty acid or omega-6 fatty acid biosynthetic pathway enzyme is selected from the group consisting of desaturases and elongases.

10. The method according to claim 8, wherein the transformed yeast cell is a member of a genus selected from the group of consisting of: *Yarrowia, Candida, Rhodotorula, Rhodosporidium, Cryptococcus, Trichosporon* and *Lipomyces*.

11. The method according to claim 8, wherein the omega-3 fatty acid or the omega-6 fatty acid is selected from the group consisting of: linoleic acid, gamma-linolenic acid, eicosadienoic acid, dihomo-gamma-linolenic acid, arachidonic acid, alpha-linoleic acid, stearidonic acid, eicosatrienoic acid, eicosatetraenoic acid, eicosapentaenoic acid, docosatetraenoic acid, omega-6 docosapentaenoic acid, omega-3 docosapentaenoic acid and docosahexaenoic acid.

* * * * *

SEQUENCE LISTING

<160> NUMBER OF SEQ ID NOS: 36

<210> SEQ ID NO 1
<211> LENGTH: 2119
<212> TYPE: DNA
<213> ORGANISM: Yarrowia lipolytica
<220> FEATURE:
<221> NAME/KEY: misc_feature
<222> LOCATION: (291)..(293)
<223> OTHER INFORMATION: translation initiation codon ('ATG'); coding
      sequence 291-1835
<300> PUBLICATION INFORMATION:
<302> TITLE: ACYLTRANSFERASES FOR ALTERATION OF POLYUNSATURATED FATTY
      ACIDS AND OIL CONTENT IN OLEAGINOUS YEASTS
<310> PATENT DOCUMENT NUMBER: U.S. 7,267,976
<311> PATENT FILING DATE: 2004-07-01
<312> PUBLICATION DATE: 2007-09-11
<313> RELEVANT RESIDUES IN SEQ ID NO: (1)..(2119)

<400> SEQUENCE: 1

```
aaacgcaccc actgctcgtc ctccttgctc ctcgaaaccg actcctctac acacgtcaaa      60
tccgaggttg aaatcttccc cacatttggc agccaaacca gcacatccca gcaacctcgc     120
acagcgccga aatcgacctg tcgacttggc acaaaaaaa agcaccggct ctgcaacagt     180
tctcacgacc aattacgtac aagtacgaaa tcgttcgtgg accgtgactg ataagctccc     240 acttttctt ctaacaacag gcaacagaca agtcacacaa aacaaaagct atgactatcg     300
actcacaata ctacaagtcg cgagacaaaa acgacacggc acccaaaatc gcgggaatcc     360
gatatgcccc gctatcgaca ccattactca accgatgtga accttctct ctggtctggc     420 acattttcag cattcccact ttcctcacaa ttttcatgct atgctgcgca attccactgc     480
tctggccatt tgtgattgcg tatgtagtgt acgctgttaa agacgactcc ccgtccaacg     540
gaggagtggt caagcgatac tcgcctattt caagaaactt cttcatctgg aagctctttg     600
gccgctactt ccccataact ctgcacaaga cggtggatct ggagcccacg cacacatact     660
accctctgga cgtccaggag tatcacctga ttgctgagag atactggccg cagaacaagt     720
acctccgagc aatcatctcc accatcgagt actttctgcc cgccttcatg aaacggtctc     780
tttctatcaa cgagcaggag cagcctgccg agcgagatcc tctcctgtct cccgttttctc     840 ccagctctcc gggttctcaa cctgacaagt ggattaacca cgacagcaga tatagccgtg     900
gagaatcatc tggctccaac ggccacgcct cgggctccga acttaacggc aacggcaaca     960
atggcaccac taaccgacga cctttgtcgt ccgcctctgc tggctccact gcatctgatt    1020
ccacgcttct taacgggtcc ctcaactcct acgccaacca gatcattggc gaaaacgacc    1080
cacagctgtc gcccacaaaa ctcaagccca ctggcagaaa atacatcttc ggctaccacc    1140
cccacggcat tatcggcatg ggagcctttg gtggaattgc caccgaggga gctggatggt    1200
ccaagctctt tccgggcatc cctgtttctc ttatgactct caccaacaac ttccgagtgc    1260
ctctctacag agagtacctc atgagtctgg gagtcgcttc tgtctccaag aagtcctgca    1320
aggccctcct caagcgaaac cagtctatct gcattgtcgt tggtggagca caggaaagtc    1380
ttctggccag acccggtgtc atggacctgg tgctactcaa gcgaaagggt tttgttcgac    1440
ttggtatgga ggtcggaaat gtcgcccttg ttcccatcat ggcctttggt gagaacgacc    1500
tctatgacca ggttagcaac acaagtcgt ccaagctgta ccgattccag cagttttgtca    1560 agaacttcct tggattcacc cttccttga tgcatgcccg aggcgtcttc aactacgatg    1620
tcggtcttgt ccctacagg cgaccccgtca acattgtggt tggttccccc attgacttgc    1680
cttatctccc acaccccacc gacgaagaag tgtccgaata ccacgaccga tacatcgccg    1740
```

```
agctgcagcg aatctacaac gagcacaagg atgaatattt catcgattgg accgaggagg    1800
gcaaaggagc cccagagttc cgaatgattg agtaaggaaa actgcctggg ttaggcaaat    1860
agctaatgag tattttttg atggcaacca aatgtagaaa gaaaaaaaaa aaaaaagaaa     1920
aaaaaaagag aatattatat ctatgtaatt ctattaaaag ctctgttgag tgagcggaat    1980
aaatactgtt gaagagggga ttgtgtagag atctgtttac tcaatggcaa actcatctgg    2040
gggagatcct tccactgtgg gaagctcctg gatagccttt gcatcgggt tcaagaagac     2100 cattgtgaac agcccttga                                                 2119
```

```
<210> SEQ ID NO 2
<211> LENGTH: 1578
<212> TYPE: DNA
<213> ORGANISM: Yarrowia lipolytica
<300> PUBLICATION INFORMATION:
<302> TITLE: DIACYLGLYCEROL ACYLTRANSFERASES FOR ALTERATION OF
      POLYUNSATURATED FATTY ACIDS AND OIL CONTENT IN OLEAGINOUS
      ORGANISMS
<310> PATENT DOCUMENT NUMBER: U.S. 7,273,746
<311> PATENT FILING DATE: 2004-12-29
<312> PUBLICATION DATE: 2007-09-25
<313> RELEVANT RESIDUES IN SEQ ID NO: (1)..(1578)

<400> SEQUENCE: 2
```

```
atggaggtcc gacgacgaaa gatagacgtg ctcaaggccc agaaaaacgg ctacgaatcg    60
ggcccaccat ctcgacaatc gtcgcagccc tcctcaagag catcgtccag aacccgcaac    120
aaacactcct cgtccaccct gtcgctcagc ggactgacca tgaaagtcca gaagaaacct    180
gcgggacccc cggcgaactc caaaacgcca ttcctacaca tcaagcccgt gcacacgtgc    240
tgctccacat caatgctttc gcgcgattat gacggctcca accccagctt caagggcttc    300
aaaaacatcg gcatgatcat tctcattgtg ggaaatctac ggctcgcatt cgaaaactac    360
ctcaaatacg gcatttccaa cccgttcttc gaccccaaaa ttactccttc cgagtggcag    420
ctctcaggct tgctcatagt cgtggcctac gcacatatcc tcatggccta cgctattgag    480
agcgctgcca agctgctgtt cctctctagc aaacaccact acatggccgt ggggcttctg    540
cataccatga acactttgtc gtccatctcg ttgctgtcct acgtcgtcta ctactacctg    600
cccaaccccg tggcaggcac aatagtcgag tttgtggccg ttattctgtc tctcaaactc    660
gcctcatacg ccctcactaa ctcggatctc cgaaaagccg caattcatgc ccagaagctc    720
gacaagacgc aagacgataa cgaaaaggaa tccacctcgt cttcctcttc ttcagatgac    780
gcagagactt tggcagacat tgacgtcatt cctgcatact acgcacagct gccctacccc    840
cagaatgtga cgctgtcgaa cctgctgtac ttctggtttg ctcccacact ggtctaccag    900
cccgtgtacc ccaagacgga gcgtattcga cccaagcacg tgatccgaaa cctgtttgag    960
ctcgtctctc tgtgcatgct tattcagttt ctcatcttcc agtacgccta cccccatcatg    1020 cagtcgtgtc tggctctgtt cttccagccc aagctcgatt atgccaacat ctccgagcgc    1080
ctcatgaagt tggcctccgt gtctatgatg gtctggctca ttggattcta cgctttcttc    1140
cagaacggtc tcaatcttat tgccgagctc acctgttttg aaacagaac cttctaccag    1200 cagtggtgga ttcccgctc cattggccag tactggactc tatggaacaa gccagtcaac    1260
cagtacttta gacaccacgt ctacgtgcct cttctcgctc ggggcatgtc gcggttcaat    1320
gcgtcggtgg tggttttctt tttctccgcc gtcatccatg aactgcttgt cggcatcccc    1380
actcacaaca tcatcggagc cgccttcttc ggcatgatgt cgcaggtgcc tctgatcatg    1440
```

```
gctactgaga accttcagca tattaactcc tctctgggcc ccttccttgg caactgtgca      1500
ttctggttca ccttttttcct gggacaaccc acttgtgcat ccttttacta tttggcctac      1560
aactacaagc agaaccag                                                     1578

<210> SEQ ID NO 3
<211> LENGTH: 9499
<212> TYPE: DNA
<213> ORGANISM: Artificial Sequence
<220> FEATURE:
<223> OTHER INFORMATION: Plasmid pDG2LGUS

<400> SEQUENCE: 3
aaacgaattc gcccttccaa tcgattgttg tgaaaattag cacggttata ttagcccgta        60
ataaatgccc gtctccatct tcatatggcc atcaccccgc aaatagccgg ccaatcaggc       120
gtatgtcacc tgttgctcac acgcatgtcc tcggaccgtt gtattgtgca agtaggggta       180 cctcccgat ccatcctcga ccagtggcac gctcaacccc acggttcgct tttctctttt        240
cgtctatcct gaactgagtt ttttttccacg ccaactgata tcccccttacg ttaccccctc     300 atcacctggt gaggcgaaac tgtaaggtga aagctaaaaa tgacatctca gctgcacgaa       360
ggaccggggc ttaaaagacg ggctggtgct tgtgatttaa aactggacaa atctcagctt      420
gcttgaaatt ttggtctcca actgtttccg agcgaatcgc acacaaaccg ggcttctctc       480
tgcagaccac gccccgaaa ctctttctcc caccaccacc aacactccct ttccattccc        540
acaccgttcc tctctcgtgc gtcatccttg cgcaatcatc ttcgtctgcg acatattgta       600
cgacatacag taccacggaa cgtttcagac cgtcgacgtg aacacatctt aggaacagca       660
acctgagcta cagaaatcta tctataggcg ataaaaaaa cgcacccact gctcgtcctc       720
cttgctcctc gaaaccgact cctctacaca cgtcaaatcc gaggttgaaa tcttccccac       780
atttggcagc caaaccagca catcccagca acctcgcaca gcgccgaaat cgacctgtcg       840
acttggccac aaaaaaaagc accggctctg caacagttct cacgaccaat tacgtacaag      900
tacgaaatcg ttcgtggacc gtgactgata agctcccact ttttcttcta acaacaggca       960
acagacaagt cacacaaaac aaaagccatg catggatgg tacgtcctgt agaaaccccca      1020 acccgtgaaa tcaaaaaact cgacggcctg tgggcattca gtctggatcg cgaaaactgt      1080
ggaattgatc agcgttggtg ggaaagcgcg ttacaagaaa gccgggcaat tgctgtgcca      1140
ggcagtttta acgatcagtt cgccgatgca gatattcgta attatgcggg caacgtctgg     1200
tatcagcgcg aagtctttat accgaaaggt tgggcaggcc agcgtatcgt gctgcgtttc      1260
gatgcggtca ctcattacgg caaagtgtgg gtcaataatc aggaagtgat ggagcatcag      1320
ggcggctata cgccatttga agccgatgtc acgccgtatg ttattgccgg aaaagtgta       1380 cgtatcaccg tttgtgtgaa caacgaactg aactggcaga ctatcccgcc gggaatggtg      1440
attaccgacg aaaacggcaa gaaaaagcag tcttacttcc atgatttctt taactatgcc      1500
gggatccatc gcagcgtaat gctctacacc acgccgaaca cctgggtgga cgatatcacc      1560
gtggtgacgc atgtcgcgca agactgtaac cacgcgtctg ttgactggca ggtggtggcc      1620
aatggtgatg tcagcgttga actgcgtgat gcggatcaac aggtggttgc aactggacaa      1680
ggcactagcg ggactttgca agtggtgaat ccgcacctct ggcaaccggg tgaaggttat     1740
ctctatgaac tgtgcgtcac agccaaaagc cagacagagt gtgatatcta cccgcttcgc      1800
gtcggcatcc ggtcagtggc agtgaagggc gaacagttcc tgattaacca caaaccgttc      1860
tactttactg gctttggtcg tcatgaagat gcggacttac gtggcaaagg attcgataac      1920
```

```
gtgctgatgg tgcacgacca cgcattaatg gactggattg gggccaactc ctaccgtacc    1980
tcgcattacc cttacgctga agagatgctc gactgggcag atgaacatgg catcgtggtg    2040
attgatgaaa ctgctgctgt cggctttaac ctctctttag cattggtttt cgaagcgggc    2100
aacaagccga agaactgta cagcgaagag gcagtcaacg ggaaactca gcaagcgcac     2160 ttacaggcga ttaaagagct gatagcgcgt gacaaaaacc acccaagcgt ggtgatgtgg    2220
agtattgcca acgaaccgga tacccgtccg caagtgcacg ggaatatttc gccactggcg    2280
gaagcaacgc gtaaactcga cccgacgcgt ccgatcacct gcgtcaatgt aatgttctgc    2340
gacgctcaca ccgataccat cagcgatctc tttgatgtgc tgtgcctgaa ccgttattac    2400
ggatggtatg tccaaagcgg cgatttggaa acggcagaga aggtactgga aaaagaactt    2460
ctggcctggc aggagaaact gcatcagccg attatcatca ccgaatacgg cgtggatacg    2520
ttagccgggc tgcactcaat gtacaccgac atgtggagtg aagagtatca gtgtgcatgg    2580
ctggatatgt atcaccgcgt ctttgatcgc gtcagcgccg tcgtcggtga acaggtatgg    2640
aatttcgccg attttgcgac ctcgcaaggc atattgcgcg ttggcggtaa caagaaaggg    2700
atcttcactc gcgaccgcaa accgaagtcg gcggcttttc tgctgcaaaa acgctggact    2760
ggcatgaact tcggtgaaaa accgcagcag ggaggcaaac aatgattaat taactagagc    2820
ggccgccacc gcggcccgag attccggcct cttcggccgc caagcgaccc gggtggacgt    2880
ctagaggtac ctagcaatta acagatagtt tgccggtgat aattctctta acctcccaca    2940
ctcctttgac ataacgattt atgtaacgaa actgaaattt gaccagatat tgtgtccgcg    3000
gtggagctcc agcttttgtt cccttttagtg agggttaatt tcgagcttgg cgtaatcatg    3060
gtcatagctg tttcctgtgt gaaattgtta tccgctcaca attccacaca acatacgagc    3120
cggaagcata aagtgtaaag cctggggtgc ctaatgagtg agctaactca cattaattgc    3180
gttgcgctca ctgcccgctt tccagtcggg aaacctgtcg tgccagctgc attaatgaat    3240
cggccaacgc gcgggggagag gcggtttgcg tattgggcgc tcttccgctt cctcgctcac    3300
tgactcgctg cgctcggtcg ttcggctgcg gcgagcggta tcagctcact caaaggcggt    3360
aatacggtta tccacagaat cagggggataa cgcaggaaag aacatgtgag caaaaggcca    3420
gcaaaaggcc aggaaccgta aaaaggccgc gttgctggcg ttttttccata ggctccgccc    3480 ccctgacgag catcacaaaa atcgacgctc aagtcagagg tggcgaaacc cgacaggact    3540
ataaagatac caggcgtttc ccctggaag ctccctcgtg cgctctcctg ttccgaccct    3600
gccgcttacc ggatacctgt ccgcctttct cccttcggga agcgtggcgc tttctcatag    3660
ctcacgctgt aggtatctca gttcggtgta ggtcgttcgc tccaagctgg gctgtgtgca    3720 cgaaccccc gttcagcccg accgctgcgc cttatccggt aactatcgtc ttgagtccaa    3780
cccggtaaga cacgacttat cgccactggc agcagccact ggtaacagga ttagcagagc    3840
gaggtatgta ggcggtgcta cagagttctt gaagtggtgg cctaactacg gctacactag    3900
aaggacagta tttggtatct gcgctctgct gaagccagtt accttcggaa aaagagttgg    3960
tagctcttga tccggcaaac aaaccaccgc tggtagcggt ggtttttttg tttgcaagca    4020
gcagattacg cgcagaaaaa aaggatctca agaagatcct ttgatctttt ctacggggtc    4080
tgacgctcag tggaacgaaa actcacgtta agggattttg gtcatgagat tatcaaaaag    4140
gatcttcacc tagatccttt taaattaaaa atgaagtttt aaatcaatct aaagtatata    4200
tgagtaaact tggtctgaca gttaccaatg cttaatcagt gaggcaccta tctcagcgat    4260
```

-continued

```
ctgtctattt cgttcatcca tagttgcctg actccccgtc gtgtagataa ctacgatacg    4320
ggagggctta ccatctggcc ccagtgctgc aatgataccg cgagacccac gctcaccggc    4380
tccagattta tcagcaataa accagccagc cggaagggcc gagcgcagaa gtggtcctgc    4440
aactttatcc gcctccatcc agtctattaa ttgttgccgg gaagctagag taagtagttc    4500
gccagttaat agtttgcgca acgttgttgc cattgctaca ggcatcgtgg tgtcacgctc    4560
gtcgtttggt atggcttcat tcagctccgg ttcccaacga tcaaggcgag ttacatgatc    4620
ccccatgttg tgcaaaaaag cggttagctc cttcggtcct ccgatcgttg tcagaagtaa    4680
gttggccgca gtgttatcac tcatggttat ggcagcactg cataattctc ttactgtcat    4740
gccatccgta agatgctttt ctgtgactgg tgagtactca accaagtcat tctgagaata    4800
gtgtatgcgg cgaccgagtt gctcttgccc ggcgtcaata cgggataata ccgcgccaca    4860
tagcagaact ttaaaagtgc tcatcattgg aaaacgttct cggggcgaaa actctcaag    4920 gatcttaccg ctgttgagat ccagttcgat gtaacccact cgtgcaccca actgatcttc    4980
agcatctttt actttcacca gcgtttctgg gtgagcaaaa acaggaaggc aaaatgccgc    5040
aaaaaaggga ataagggcga cacggaaatg ttgaatactc atactcttcc ttttcaata    5100 ttattgaagc atttatcagg gttattgtct catgagcgga tacatatttg aatgtattta    5160
gaaaaataaa caaataggg ttccgcgcac atttccccga aaagtgccac ctgacgcgcc    5220
ctgtagcggc gcattaagcg cggcgggtgt ggtggttacg cgcagcgtga ccgctacact    5280
tgccagcgcc ctagcgcccg ctcctttcgc tttcttccct tcctttctcg ccacgttcgc    5340
cggctttccc cgtcaagctc taaatcgggg gctcccttta gggttccgat ttagtgcttt    5400
acggcacctc gaccccaaaa aacttgatta gggtgatggt tcacgtagtg gccatcgcc    5460 ctgatagacg gttttcgcc ctttgacgtt ggagtccacg ttctttaata gtggactctt    5520
gttccaaact ggaacaacac tcaaccctat ctcggtctat tcttttgatt tataagggat    5580
tttgccgatt tcggcctatt ggttaaaaaa tgagctgatt taacaaaaat ttaacgcgaa    5640
ttttaacaaa atattaacgc ttacaatttc cattcgccat tcaggctgcg caactgttgg    5700
gaagggcgat cggtgcgggc ctcttcgcta ttacgccagc tggcgaaagg gggatgtgct    5760
gcaaggcgat taagttgggt aacgccaggg ttttcccagt cacgacgttg taaaacgacg    5820
gccagtgaat tgtaatacga ctcactatag ggcgaattgg gtaccgggcc ccccctcgag    5880
gtcgatggtg tcgataagct tgatatcgaa ttcatgtcac acaaaccgat cttcgcctca    5940
aggaaaccta attctacatc cgagagactg ccgagatcca gtctacactg attaattttc    6000
gggccaataa tttaaaaaaa tcgtgttata taatattata tgtattatat atatacatca    6060
tgatgatact gacagtcatg tcccattgct aaatagacag actccatctg ccgcctccaa    6120
ctgatgttct caatatttaa ggggtcatct cgcattgttt aataataaac agactccatc    6180
taccgcctcc aaatgatgtt ctcaaaatat attgtatgaa cttatttta ttacttagta    6240 ttattagaca acttacttgc tttatgaaaa acacttccta tttaggaaac aatttataat    6300
ggcagttcgt tcatttaaca atttatgtag aataaatgtt ataaatgcgt atgggaaatc    6360
ttaaatatgg atagcataaa tgatatctgc attgcctaat tcgaaatcaa cagcaacgaa    6420
aaaaatccct tgtacaacat aaatagtcat cgagaaatat caactatcaa agaacagcta    6480
ttcacacgtt actattgaga ttattattgg acgagaatca cactcaac tgtctttctc    6540 tcttctagaa atacaggtac aagtatgtac tattctcatt gttcatactt ctagtcattt    6600
catcccacat attccttgga tttctctcca atgaatgaca ttctatcttg caaattcaac    6660
```

```
aattataata agatatacca aagtagcggt atagtggcaa tcaaaaagct tctctggtgt    6720
gcttctcgta tttatttta ttctaatgat ccattaaagg tatatattta ttcttgtta     6780
tataatcctt ttgtttatta catgggctgg atacataaag gtattttgat ttaattttt    6840
gcttaaattc aatcccccct cgttcagtgt caactgtaat ggtaggaaat taccatactt   6900
ttgaagaagc aaaaaaatg aaagaaaaaa aaatcgtat tccaggtta gacgttccgc      6960
agaatctaga atgcggtatg cggtacattg ttcttcgaac gtaaaagttg cgctccctga   7020
gatattgtac atttttgctt ttacaagtac aagtacatcg tacaactatg tactactgtt   7080
gatgcatcca caacagttg ttttgttttt ttttgttttt tttttttcta atgattcat     7140
accgctatgt atacctactt gtacttgtag taagccgggt tattggcgtt caattaatca   7200
tagacttatg aatctgcacg gtgtgcgctg cgagttactt ttagcttatg catgctactt   7260
gggtgtaata ttgggatctg ttcggaaatc aacggatgct caaccgattt cgacagtaat   7320
aatttgaatc gaatcggagc ctaaaatgaa cccgagtata tctcataaaa ttctcggtga   7380
gaggtctgtg actgtcagta caaggtgcct tcattatgcc ctcaaccta ccatacctca    7440
ctgaatgtag tgtacctcta aaatgaaat acagtgccaa aagccaaggc actgagctcg    7500
tctaacggac ttgatataca accaattaaa acaaatgaaa agaaatacag ttctttgtat   7560
catttgtaac aattaccctg tacaaactaa ggtattgaaa tcccacaata ttcccaaagt   7620
ccacccttt ccaaattgtc atgcctacaa ctcatatacc aagcactaac ctaccaaaca    7680
ccactaaaac cccacaaaat atatcttacc gaatatacag taacaagcta ccaccacact   7740
cgttgggtgc agtcgccagc ttaaagatat ctatccacat cagccacaac tcccttcctt   7800
taataaaccg actacaccct tggctattga ggttatgagt gaatatactg tagacaagac   7860
actttcaaga agactgttc caaaacgtac cactgtcctc cactacaaac acacccaatc    7920
tgcttcttct agtcaaggtt gctacaccgg taaattataa atcatcattt cattagcagg   7980
gcagggccct tttatagag tcttatacac tagcggaccc tgccggtaga ccaacccgca    8040
ggcgcgtcag tttgctcctt ccatcaatgc gtcgtagaaa cgacttactc cttcttgagc   8100
agctccttga ccttgttggc aacaagtctc cgacctcgga ggtggaggaa gagcctccga   8160
tatcggcggt agtgatacca gcctcgacgg actccttgac ggcagcctca acagcgtcac   8220
cggcgggctt catgttaaga gagaacttga gcatcatggc ggcagacaga atggtggcaa   8280
tggggttgac cttctgcttg ccgagatcgg gggcagatcc gtgacagggc tcgtacagac   8340
cgaacgcctc gttggtgtcg ggcagagaag ccagagaggc ggaggcagc agacccagag    8400
aaccggggat gacggaggcc tcgtcggaga tgatatcgcc aaacatgttg gtggtgatga   8460
tgataccatt catcttggag ggctgcttga tgaggatcat ggcggccgag tcgatcagct   8520
ggtggttgag ctcgagctgg gggaattcgt ccttgaggac tcgagtgaca gtctttcgcc   8580
aaagtcgaga ggaggccagc acgttggcct tgtcaagaga ccacgggga agagggggt     8640
tgtgctgaag ggccaggaag gcggccattc gggcaattcg ctcaacctca ggaacggagt   8700
aggtctcggt gtcggaagcg acgccagatc cgtcatcctc ctttcgctct ccaaagtaga   8760
tacctccgac gagctctcgg acaatgatga agtcggtgcc ctcaacgttt cggatggggg   8820
agagatcggc gagcttgggc gacagcagct ggcagggtcg caggttggcg tacaggttca   8880
ggtcctttcg cagcttgagg agaccctgct cgggtcgcac gtcggttcgt ccgtcggag    8940
tggtccatac ggtgttggca gcgcctccga cagcaccgag cataatagag tcagcctttc   9000
```

| | | | | |
|---|---|---|---|---|
| ggcagatgtc | gagagtagcg | tcggtgatgg | gctcgccctc | cttctcaatg gcagctcctc | 9060 |
| caatgagtcg | gtcctcaaac | acaaactcgg | tgccggaggc | ctcagcaaca gacttgagca | 9120 |
| ccttgacggc | ctcggcaatc | acctcggggc | cacagaagtc | gccgccgaga agaacaatct | 9180 |
| tcttggagtc | agtcttggtc | ttcttagttt | cgggttccat | tgtggatgtg tgtggttgta | 9240 |
| tgtgtgatgt | ggtgtgtgga | gtgaaaatct | gtggctggca | aacgctcttg tatatatacg | 9300 |
| cacttttgcc | cgtgctatgt | ggaagactaa | acctccgaag | attgtgactc aggtagtgcg | 9360 |
| gtatcggcta | gggacccaaa | ccttgtcgat | gccgatagcg | ctatcgaacg taccccagcc | 9420 |
| ggccgggagt | atgtcggagg | ggacatacga | gatcgtcaag | ggtttgtggc caactggtaa | 9480 |
| ataaatgatg | tcgacgttt | | | | 9499 |

<210> SEQ ID NO 4
<211> LENGTH: 966
<212> TYPE: DNA
<213> ORGANISM: Yarrowia lipolytica

<400> SEQUENCE: 4

| | | | | |
|---|---|---|---|---|
| cgattgttgt | gaaaattagc | acggttatat | tagcccgtaa | taaatgcccg tctccatctt | 60 |
| catatggcca | tcaccccgca | aatagccggc | caatcaggcg | tatgtcacct gttgctcaca | 120 |
| cgcatgtcct | cggaccgttg | tattgtgcaa | gtaggggtac | ctccccgatc catcctcgac | 180 |
| cagtggcacg | ctcaacccca | cggttcgctt | ttctcttttc | gtctatcctg aactgagttt | 240 |
| ttttccacgc | caactgatat | ccccttacgt | taccccctca | tcacctggtg aggcgaaact | 300 |
| gtaaggtgaa | agctaaaaat | gacatctcag | ctgcacgaag | gaccggggct aaaagacgg | 360 |
| gctggtgctt | gtgatttaaa | actggacaaa | tctcagcttg | cttgaaattt tggtctccaa | 420 |
| ctgtttccga | gcgaatcgca | cacaaaccgg | gcttctctct | gcagaccacg cccccgaaac | 480 |
| tctttctccc | accaccacca | acactcccct | tccattccca | caccgttcct ctctcgtgcg | 540 |
| tcatccttgc | gcaatcatct | tcgtctgcga | catattgtac | gacatacagt accacggaac | 600 |
| gtttcagacc | gtcgacgtga | acacatctta | ggaacagcaa | cctgagctac agaaatctat | 660 |
| ctataggcga | ataaaaaaac | gcacccactg | ctcgtcctcc | ttgctcctcg aaaccgactc | 720 |
| ctctacacac | gtcaaatccg | aggttgaaat | cttccccaca | tttggcagcc aaaccagcac | 780 |
| atcccagcaa | cctcgcacag | cgccgaaatc | gacctgtcga | cttggccaca aaaaaagca | 840 |
| ccggctctgc | aacagttctc | acgaccaatt | acgtacaagt | acgaaatcgt tcgtggaccg | 900 |
| tgactgataa | gctcccactt | tttcttctaa | caacaggcaa | cagacaagtc acacaaaaca | 960 |
| aaagcc | | | | | 966 |

<210> SEQ ID NO 5
<211> LENGTH: 9237
<212> TYPE: DNA
<213> ORGANISM: Artificial Sequence
<220> FEATURE:
<223> OTHER INFORMATION: Plasmid pDG2MGUS

<400> SEQUENCE: 5

| | | | | |
|---|---|---|---|---|
| catggcatgg | atggtacgtc | ctgtagaaac | cccaacccgt | gaaatcaaaa aactcgacgg | 60 |
| cctgtgggca | ttcagtctgg | atcgcgaaaa | ctgtggaatt | gatcagcgtt ggtgggaaag | 120 |
| cgcgttacaa | gaaagccggg | caattgctgt | gccaggcagt | tttaacgatc agttcgccga | 180 |
| tgcagatatt | cgtaattatg | cgggcaacgt | ctggtatcag | cgcgaagtct ttataccgaa | 240 |
| aggttgggca | ggccagcgta | tcgtgctgcg | tttcgatgcg | gtcactcatt acggcaaagt | 300 |

-continued

```
gtgggtcaat aatcaggaag tgatggagca tcagggcggc tatacgccat ttgaagccga      360
tgtcacgccg tatgttattg ccgggaaaag tgtacgtatc accgtttgtg tgaacaacga      420
actgaactgg cagactatcc cgccgggaat ggtgattacc gacgaaaacg gcaagaaaaa      480
gcagtcttac ttccatgatt tctttaacta tgccgggatc catcgcagcg taatgctcta      540
caccacgccg aacacctggg tggacgatat caccgtggtg acgcatgtcg cgcaagactg      600
taaccacgcg tctgttgact ggcaggtggt ggccaatggt gatgtcagcg ttgaactgcg      660
tgatgcggat caacaggtgg ttgcaactgg acaaggcact agcgggactt gcaagtggt       720 gaatccgcac ctctggcaac cgggtgaagg ttatctctat gaactgtgcg tcacagccaa      780
aagccagaca gagtgtgata tctacccgct tcgcgtcggc atccggtcag tggcagtgaa      840
gggcgaacag ttcctgatta accacaaacc gttctacttt actggctttg gtcgtcatga      900
agatgcggac ttacgtggca aaggattcga taacgtgctg atggtgcacg accacgcatt      960
aatggactgg attggggcca actcctaccg tacctcgcat tacccttacg ctgaagagat     1020
gctcgactgg gcagatgaac atggcatcgt ggtgattgat gaaactgctg ctgtcggctt     1080
taacctctct ttaggcattg gtttcgaagc gggcaacaag ccgaaagaac tgtacagcga     1140
agaggcagtc aacggggaaa ctcagcaagc gcacttacag gcgattaaag agctgatagc     1200
gcgtgacaaa aaccacccaa gcgtggtgat gtggagtatt gccaacgaac cggatacccg     1260
tccgcaagtg cacgggaata tttcgccact ggcggaagca acgcgtaaac tcgacccgac     1320
gcgtccgatc acctgcgtca atgtaatgtt ctgcgacgct cacaccgata ccatcagcga     1380
tctctttgat gtgctgtgcc tgaaccgtta ttacggatgg tatgtccaaa gcggcgattt     1440
ggaaacggca gagaaggtac tggaaaaaga acttctggcc tggcaggaga aactgcatca     1500
gccgattatc atcaccgaat acggcgtgga tacgttagcc gggctgcact caatgtacac     1560
cgacatgtgg agtgaagagt atcagtgtgc atggctggat atgtatcacc gcgtctttga     1620
tcgcgtcagc gccgtcgtcg gtgaacaggt atggaatttc gccgattttg cgacctcgca     1680
aggcatattg cgcgttggcg gtaacaagaa agggatcttc actcgcgacc gcaaaccgaa     1740
gtcggcggct tttctgctgc aaaaacgctg gactggcatg aacttcggtg aaaaaccgca     1800
gcagggaggc aaacaatgat taattaacta gagcggccgc caccgcggcc cgagattccg     1860
gcctcttcgg ccgccaagcg acccgggtgg acgtctagag gtacctagca attaacagat     1920
agtttgccgg tgataattct cttaacctcc cacactcctt tgacataacg atttatgtaa     1980
cgaaactgaa atttgaccag atattgtgtc cgcggtggag ctccagcttt tgttcccttt     2040
agtgagggtt aatttcgagc ttggcgtaat catggtcata gctgtttcct gtgtgaaatt     2100
gttatccgct cacaattcca cacaacatac gagccggaag cataaagtgt aaagcctggg     2160
gtgcctaatg agtgagctaa ctcacattaa ttgcgttgcg ctcactgccc gctttccagt     2220
cgggaaacct gtcgtgccag ctgcattaat gaatcggcca acgcgcgggg agaggcggtt     2280
tgcgtattgg gcgctcttcc gcttcctcgc tcactgactc gctgcgctcg tcgttcggc      2340 tgcggcgagc ggtatcagct cactcaaagg cggtaatacg gttatccaca gaatcagggg     2400
ataacgcagg aaagaacatg tgagcaaaag gccagcaaaa ggccaggaac cgtaaaaagg     2460
ccgcgttgct ggcgtttttc cataggctcc gccccctga cgagcatcac aaaaatcgac       2520
gctcaagtca gaggtggcga aacccgacag gactataaag ataccaggcg tttccccctg     2580
gaagctccct cgtgcgctct cctgttccga ccctgccgct taccggatac ctgtccgcct     2640
```

```
ttctcccttc gggaagcgtg gcgctttctc atagctcacg ctgtaggtat ctcagttcgg      2700
tgtaggtcgt tcgctccaag ctgggctgtg tgcacgaacc ccccgttcag cccgaccgct      2760
gcgccttatc cggtaactat cgtcttgagt ccaacccggt aagacacgac ttatcgccac      2820
tggcagcagc cactggtaac aggattagca gagcgaggta tgtaggcggt gctacagagt      2880
tcttgaagtg gtggcctaac tacggctaca ctagaaggac agtatttggt atctgcgctc      2940
tgctgaagcc agttaccttc ggaaaaagag ttggtagctc ttgatccggc aaacaaacca      3000
ccgctggtag cggtggtttt tttgtttgca agcagcagat tacgcgcaga aaaaaggat      3060 ctcaagaaga cctttgatc ttttctacgg ggtctgacgc tcagtggaac gaaaactcac      3120
gttaagggat tttggtcatg agattatcaa aaaggatctt cacctagatc cttttaaatt      3180
aaaaatgaag ttttaaatca atctaaagta tatatgagta aacttggtct gacagttacc      3240
aatgcttaat cagtgaggca cctatctcag cgatctgtct atttcgttca tccatagttg      3300
cctgactccc cgtcgtgtag ataactacga tacgggaggg cttaccatct ggccccagtg      3360
ctgcaatgat accgcgagac ccacgctcac cggctccaga tttatcagca ataaaccagc      3420
cagccggaag ggccgagcgc agaagtggtc ctgcaacttt atccgcctcc atccagtcta      3480
ttaattgttg ccgggaagct agagtaagta gttcgccagt taatagtttg cgcaacgttg      3540
ttgccattgc tacaggcatc gtggtgtcac gctcgtcgtt tggtatggct tcattcagct      3600
ccggttccca acgatcaagg cgagttacat gatcccccat gttgtgcaaa aaagcggtta      3660
gctccttcgg tcctccgatc gttgtcagaa gtaagttggc cgcagtgtta tcactcatgg      3720
ttatggcagc actgcataat tctcttactg tcatgccatc cgtaagatgc ttttctgtga      3780
ctggtgagta ctcaaccaag tcattctgag aatagtgtat gcggcgaccg agttgctctt      3840
gcccggcgtc aatacgggat aataccgcgc cacatagcag aactttaaaa gtgctcatca      3900
ttggaaaacg ttcttcgggg cgaaaactct caaggatctt accgctgttg agatccagtt      3960
cgatgtaacc cactcgtgca cccaactgat cttcagcatc ttttactttc accagcgttt      4020
ctgggtgagc aaaaacagga aggcaaaatg ccgcaaaaaa gggaataagg gcgacacgga      4080
aatgttgaat actcatactc ttcctttttc aatattattg aagcatttat cagggttatt      4140
gtctcatgag cggatacata tttgaatgta tttagaaaaa taaacaaata ggggttccgc      4200
gcacatttcc ccgaaaagtg ccacctgacg cgcctgtag cggcgcatta agcgcggcgg      4260
gtgtggtggt tacgcgcagc gtgaccgcta cacttgccag cgccctagcg cccgctcctt      4320
tcgctttctt cccttccttt ctcgccacgt tcgccggctt tccccgtcaa gctctaaatc      4380
gggggctccc tttagggttc cgatttagtg ctttacggca cctcgacccc aaaaaacttg      4440
attagggtga tggttcacgt agtgggccat cgccctgata dacggttttt cgcccttga       4500 cgttggagtc cacgttcttt aatagtggac tcttgttcca aactggaaca cactcaacc       4560 ctatctcggt ctattctttt gatttataag ggatttgcc gatttcggcc tattggttaa      4620
aaaatgagct gatttaacaa aaatttaacg cgaattttaa caaatatatta acgcttacaa      4680 tttccattcg ccattcaggc tgcgcaactg ttgggaaggg cgatcggtgc gggcctcttc      4740
gctattacgc cagctggcga aagggggatg tgctgcaagg cgattaagtt gggtaacgcc      4800
agggttttcc cagtcacgac gttgtaaaac gacggccagt gaattgtaat acgactcact      4860
atagggcgaa ttgggtaccg gccccccct cgaggtcgat ggtgtcgata agcttgatat      4920
cgaattcatg tcacacaaac cgatcttcgc ctcaaggaaa cctaattcta catccgagag      4980
actgccgaga tccagtctac actgattaat tttcgggcca ataatttaaa aaaatcgtgt      5040
```

-continued

```
tatataatat tatatgtatt atatatatac atcatgatga tactgacagt catgtcccat    5100
tgctaaatag acagactcca tctgccgcct ccaactgatg ttctcaatat ttaaggggtc    5160
atctcgcatt gtttaataat aaacagactc catctaccgc ctccaaatga tgttctcaaa    5220
atatattgta tgaacttatt tttattactt agtattatta gacaacttac ttgctttatg    5280
aaaaacactt cctatttagg aaacaattta taatggcagt tcgttcattt aacaatttat    5340
gtagaataaa tgttataaat gcgtatggga aatcttaaat atggatagca taatgatat     5400
ctgcattgcc taattcgaaa tcaacagcaa cgaaaaaaat cccttgtaca acataaatag    5460
tcatcgagaa atatcaacta tcaaagaaca gctattcaca cgttactatt gagattatta    5520
ttggacgaga atcacacact caactgtctt tctctcttct agaaatacag gtacaagtat    5580
gtactattct cattgttcat acttctagtc atttcatccc acatattcct tggatttctc    5640
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat ccttttgttt attacatggg    5820
ctggatacat aaaggtattt tgatttaatt ttttgcttaa attcaatccc ccctcgttca    5880
gtgtcaactg taatggtagg aaattaccat acttttgaag aagcaaaaaa aatgaaagaa    5940
aaaaaaaatc gtatttccag gttagacgtt ccgcagaatc tagaatgcgg tatgcggtac    6000
attgttcttc gaacgtaaaa gttgcgctcc ctgagatatt gtacatttt gcttttacaa     6060
gtacaagtac atcgtacaac tatgtactac tgttgatgca tccacaacag tttgttttgt    6120
ttttttttgt ttttttttt tctaatgatt cattaccgct atgtatacct acttgtactt     6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaagaaat acagttcttt gtatcatttg taacaattac cctgtacaaa     6600
ctaaggtatt gaaatcccac aatattccca aagtccaccc ctttccaaat tgtcatgcct    6660
acaactcata taccaagcac taacctacca acaccacta aaacccccaca aaatatatct    6720
taccgaatat acagtaacaa gctaccacca cactcgttgg gtgcagtcgc cagcttaaag    6780
atatctatcc acatcagcca caactcccett cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg cccttttat agagtcttat     7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatgggt tgaccttctg cttgccgaga    7320
tcggggggcag atccgtgaca gggctcgtac agaccgaacg cctcgttggt gtcgggcaga    7380
```

```
gaagccagag aggcggaggg cagcagaccc agagaaccgg ggatgacgga ggcctcgtcg   7440
gagatgatat cgccaaacat gttggtggtg atgatgatac cattcatctt ggagggctgc   7500
ttgatgagga tcatggcggc cgagtcgatc agctggtggt tgagctcgag ctgggggaat   7560
tcgtccttga ggactcgagt gacagtcttt cgccaaagtc gagaggaggc cagcacgttg   7620
gccttgtcaa gagaccacac gggaagaggg gggttgtgct gaagggccag gaaggcggcc   7680
attcgggcaa ttcgctcaac ctcaggaacg gagtaggtct cggtgtcgga agcgacgcca   7740
gatccgtcat cctcctttcg ctctccaaag tagataccct cgacgagctc tcggacaatg   7800
atgaagtcgg tgccctcaac gtttcggatg ggggagagat cggcgagctt gggcgacagc   7860
agctggcagg gtcgcaggtt ggcgtacagg ttcaggtcct ttcgcagctt gaggagaccc   7920
tgctcgggtc gcacgtcggt tcgtccgtcg ggagtggtcc atacggtgtt ggcagcgcct   7980
ccgacagcac cgagcataat agagtcagcc tttcggcaga tgtcgagagt agcgtcggtg   8040
atgggctcgc cctccttctc aatggcagct cctccaatga gtcggtcctc aaacacaaac   8100
tcggtgccgg aggcctcagc aacagacttg agcaccttga cggcctcggc aatcacctcg   8160
gggccacaga gtcgccgcc gagaagaaca atcttcttgg agtcagtctt ggtcttctta   8220
gtttcgggtt ccattgtgga tgtgtgtggt tgtatgtgtg atgtggtgtg tggagtgaaa   8280
atctgtggct ggcaaacgct cttgtatata tacgcacttt tgcccgtgct atgtggaaga   8340
ctaaacctcc gaagattgtg actcaggtag tgcggtatcg gctagggacc caaaccttgt   8400
cgatgccgat agcgctatcg aacgtacccc agccggccgg gagtatgtcg gaggggacat   8460
acgagatcgt caagggtttg tggccaactg gtaaataaat gatgtcgacg tttaaaccac   8520
gccaactgat atccccttac gttaccccct catcacctgg tgaggcgaaa ctgtaaggtg   8580
aaagctaaaa atgacatctc agctgcacga aggaccgggg cttaaaagac gggctggtgc   8640
ttgtgattta aaactggaca atctcagct tgcttgaaat tttggtctcc aactgtttcc   8700
gagcgaatcg cacacaaacc gggcttctct ctgcagacca cgcccccgaa actctttctc   8760
ccaccaccac caacactccc tttccattcc cacaccgttc ctctctcgtg cgtcatcctt   8820
gcgcaatcat cttcgtctgc gacatattgt acgacataca gtaccacgga acgtttcaga   8880
ccgtcgacgt gaacacatct taggaacagc aacctgagct acagaaatct atctataggc   8940
ggataaaaaa acgcacccac tgctcgtcct ccttgctcct cgaaaccgac tcctctacac   9000
acgtcaaatc cgaggttgaa atcttcccca catttggcag ccaaaccagc acatcccagc   9060
aacctcgcac agcgccgaaa tcgacctgtc gacttggcca caaaaaaag caccggctct   9120 gcaacagttc tcacgaccaa ttacgtacaa gtacgaaatc gttcgtggac cgtgactgat   9180
aagctcccac ttttcttct aacaacaggc aacagacaag tcacacaaaa caaaagc    9237
```

<210> SEQ ID NO 6
<211> LENGTH: 722
<212> TYPE: DNA
<213> ORGANISM: Yarrowia lipolytica

<400> SEQUENCE: 6

```
ccacgccaac tgatatcccc ttacgttacc ccctcatcac ctggtgaggc gaaactgtaa     60
ggtgaaagct aaaaatgaca tctcagctgc acgaaggacc ggggcttaaa agacgggctg    120
gtgcttgtga tttaaaactg gacaaatctc agcttgcttg aaattttggt ctccaactgt    180
ttccgagcga atcgcacaca aaccgggctt ctctctgcag accacgcccc cgaaactctt    240
tctcccacca ccaccaacac tcccttccca ttcccacacc gttcctctct cgtgcgtcat    300
```

| | |
|---|---|
| ccttgcgcaa tcatcttcgt ctgcgacata ttgtacgaca tacagtacca cggaacgttt | 360 |
| cagaccgtcg acgtgaacac atcttaggaa cagcaacctg agctacagaa atctatctat | 420 |
| aggcggataa aaaaacgcac ccactgctcg tcctccttgc tcctcgaaac cgactcctct | 480 |
| acacacgtca atccgaggt tgaaatcttc cccacatttg gcagccaaac cagcacatcc | 540 |
| cagcaacctc gcacagcgcc gaaatcgacc tgtcgacttg gccacaaaaa aaagcaccgg | 600 |
| ctctgcaaca gttctcacga ccaattacgt acaagtacga aatcgttcgt ggaccgtgac | 660 |
| tgataagctc ccacttttc ttctaacaac aggcaacaga caagtcacac aaaacaaaag | 720 |
| cc | 722 |

<210> SEQ ID NO 7
<211> LENGTH: 9016
<212> TYPE: DNA
<213> ORGANISM: Artificial Sequence
<220> FEATURE:
<223> OTHER INFORMATION: Plasmid pDG2SGUS

<400> SEQUENCE: 7

| | |
|---|---|
| catggcatgg atggtacgtc ctgtagaaac cccaacccgt gaaatcaaaa aactcgacgg | 60 |
| cctgtgggca ttcagtctgg atcgcgaaaa ctgtggaatt gatcagcgtt ggtgggaaag | 120 |
| cgcgttacaa gaaagccggg caattgctgt gccaggcagt tttaacgatc agttcgccga | 180 |
| tgcagatatt cgtaattatg cgggcaacgt ctggtatcag cgcgaagtct ttataccgaa | 240 |
| aggttgggca ggccagcgta tcgtgctgcg tttcgatgcg gtcactcatt acggcaaagt | 300 |
| gtgggtcaat aatcaggaag tgatggagca tcagggcggc tatacgccat ttgaagccga | 360 |
| tgtcacgccg tatgttattg ccgggaaaag tgtacgtatc accgtttgtg tgaacaacga | 420 |
| actgaactgg cagactatcc cgccgggaat ggtgattacc gacgaaaacg gcaagaaaaa | 480 |
| gcagtcttac ttccatgatt tctttaacta tgccggatc catcgcagcg taatgctcta | 540 |
| caccacgccg aacacctggg tggacgatat caccgtggtg acgcatgtcg cgcaagactg | 600 |
| taaccacgcg tctgttgact ggcaggtggt ggccaatggt gatgtcagcg ttgaactgcg | 660 |
| tgatgcggat caacaggtgg ttgcaactgg acaaggcact agcgggactt gcaagtggt | 720 |
| gaatccgcac ctctggcaac cgggtgaagg ttatctctat gaactgtgcg tcacagccaa | 780 |
| aagccagaca gagtgtgata tctacccgct tcgcgtcggc atccggtcag tggcagtgaa | 840 |
| gggcgaacag ttcctgatta ccacaaaacc gttctacttt actggctttg gtcgtcatga | 900 |
| agatgcggac ttacgtggca aaggattcga taacgtgctg atggtgcacg accacgcatt | 960 |
| aatggactgg attggggcca actcctaccg tacctcgcat taccccttacg ctgaagagat | 1020 |
| gctcgactgg gcagatgaac atggcatcgt ggtgattgat gaaactgctg ctgtcggctt | 1080 |
| taacctctct ttaggcattg gtttcgaagc gggcaacaag ccgaaagaac tgtacagcga | 1140 |
| agaggcagtc aacggggaaa ctcagcaagc gcacttacag gcgattaaag agctgatagc | 1200 |
| gcgtgacaaa aaccacccaa gcgtggtgat gtggagtatt gccaacgaac cggatacccg | 1260 |
| tccgcaagtg cacgggaata tttcgccact ggcggaagca acgcgtaaac tcgacccgac | 1320 |
| gcgtccgatc acctgcgtca atgtaatgtt ctgcgacgct cacaccgata ccatcagcga | 1380 |
| tctctttgat gtgctgtgcc tgaaccgtta ttacggatgg tatgtccaaa gcggcgattt | 1440 |
| ggaaacggca gagaaggtac tggaaaaaga acttctggcc tggcaggaga aactgcatca | 1500 |
| gccgattatc atcaccgaat acggcgtgga tacgttagcc gggctgcact caatgtacac | 1560 |

```
cgacatgtgg agtgaagagt atcagtgtgc atggctggat atgtatcacc gcgtctttga    1620
tcgcgtcagc gccgtcgtcg gtgaacaggt atggaatttc gccgattttg cgacctcgca    1680
aggcatattg cgcgttggcg gtaacaagaa agggatcttc actcgcgacc gcaaaccgaa    1740
gtcggcggct tttctgctgc aaaaacgctg gactggcatg aacttcggtg aaaaaccgca    1800
gcagggaggc aaacaatgat taattaacta gagcggccgc accgcggcc cgagattccg     1860 gcctcttcgg ccgccaagcg acccgggtgg acgtctagag gtacctagca attaacagat    1920
agtttgccgg tgataattct cttaacctcc cacactcctt tgacataacg atttatgtaa    1980
cgaaactgaa atttgaccag atattgtgtc cgcggtggag ctccagcttt tgttcccttt    2040
agtgagggtt aatttcgagc ttggcgtaat catggtcata gctgtttcct gtgtgaaatt    2100
gttatccgct cacaattcca cacaacatac gagccggaag cataaagtgt aaagcctggg    2160
gtgcctaatg agtgagctaa ctcacattaa ttgcgttgcg ctcactgccc gctttccagt    2220
cgggaaacct gtcgtgccag ctgcattaat gaatcggcca acgcgcgggg agaggcggtt    2280
tgcgtattgg gcgctcttcc gcttcctcgc tcactgactc gctgcgctcg gtcgttcggc    2340
tgcggcgagc ggtatcagct cactcaaagg cggtaatacg ttatccaca gaatcagggg     2400 ataacgcagg aaagaacatg tgagcaaaag gccagcaaaa ggccaggaac cgtaaaaagg    2460
ccgcgttgct ggcgtttttc cataggctcc gcccccctga cgagcatcac aaaaatcgac    2520
gctcaagtca gaggtggcga aacccgacag gactataaag ataccaggcg tttccccctg    2580
gaagctccct cgtgcgctct cctgttccga ccctgccgct taccggatac ctgtccgcct    2640
ttctcccttc gggaagcgtg gcgctttctc atagctcacg ctgtaggtat ctcagttcgg    2700
tgtaggtcgt tcgctccaag ctgggctgtg tgcacgaacc ccccgttcag cccgaccgct    2760
gcgccttatc cggtaactat cgtcttgagt ccaacccggt aagacacgac ttatcgccac    2820
tggcagcagc cactggtaac aggattagca gagcgaggta tgtaggcggt gctacagagt    2880
tcttgaagtg gtggcctaac tacggctaca ctagaaggac agtatttggt atctgcgctc    2940
tgctgaagcc agttaccttc ggaaaaagag ttggtagctc ttgatccggc aaacaaacca    3000
ccgctggtag cggtggtttt tttgtttgca agcagcagat tacgcgcaga aaaaaaggat    3060
ctcaagaaga tcctttgatc ttttctacgg ggtctgacgc tcagtggaac gaaaactcac    3120
gttaagggat tttggtcatg agattatcaa aaaggatctt cacctagatc cttttaaatt    3180
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaccagc    3420 cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
```

```
cgatgtaacc cactcgtgca cccaactgat cttcagcatc ttttactttc accagcgttt   4020
ctgggtgagc aaaaacagga aggcaaaatg ccgcaaaaaa gggaataagg gcgacacgga   4080
aatgttgaat actcatactc ttccttttc aatattattg aagcatttat cagggttatt    4140
gtctcatgag cggatacata tttgaatgta tttagaaaaa taaacaaata ggggttccgc   4200
gcacatttcc ccgaaaagtg ccacctgacg cgccctgtag cggcgcatta gcgcggcgg    4260 gtgtggtggt tacgcgcagc gtgaccgcta cacttgccag cgccctagcg cccgctcctt   4320
tcgctttctt cccttccttt ctcgccacgt tcgccggctt tccccgtcaa gctctaaatc    4380
gggggctccc tttaggggtt cgatttagtg ctttacggca cctcgacccc aaaaaacttg   4440
attagggtga tggttcacgt agtgggccat cgccctgata cacggttttt cgccctttga   4500
cgttggagtc cacgttcttt aatagtggac tcttgttcca aactggaaca acactcaacc   4560
ctatctcggt ctattctttt gatttataag gattttgcc gatttcggcc tattggttaa    4620
aaaatgagct gatttaacaa aaatttaacg cgaatttaa caaatatta acgcttacaa     4680 tttccattcg ccattcaggc tgcgcaactg ttgggaaggg cgatcggtgc gggcctcttc   4740
gctattacgc cagctggcga aagggggatg tgctgcaagg cgattaagtt gggtaacgcc   4800
agggttttcc cagtcacgac gttgtaaaac gacggccagt gaattgtaat acgactcact   4860
atagggcgaa ttgggtaccg gcccccccct cgaggtcgat ggtgtcgata agcttgatat   4920
cgaattcatg tcacacaaac cgatcttcgc ctcaaggaaa cctaattcta catccgagag   4980
actgccgaga tccagtctac actgattaat tttcgggcca ataatttaaa aaaatcgtgt   5040
tatataatat tatatgtatt atatatatac atcatgatga tactgacagt catgtcccat   5100
tgctaaatag acagactcca tctgccgcct ccaactgatg ttctcaatat ttaaggggtc   5160
atctcgcatt gtttaataat aaacagactc catctaccgc ctccaaatga tgttctcaaa   5220
atatattgta tgaacttatt tttattactt agtattatta gacaacttac ttgctttatg   5280
aaaaacactt cctatttagg aaacaattta taatggcagt tcgttcattt aacaatttat   5340
gtagaataaa tgttataaat gcgtatggga atcttaaat atggatagca taatgatat    5400 ctgcattgcc taattcgaaa tcaacagcaa cgaaaaaat cccttgtaca acataaatag    5460
tcatcgagaa atatcaacta tcaaagaaca gctattcaca cgttactatt gagattatta   5520
ttggacgaga atcacacact caactgtctt tctctcttct agaaatacag gtacaagtat   5580
gtactattct cattgttcat acttctagtc atttcatccc acatattcct tggatttctc   5640
tccaatgaat gacattctat cttgcaaatt caacaattat aataagatat accaaagtag   5700
cggtatagtg gcaatcaaaa agcttctctg gtgtgcttct cgtatttatt tttattctaa   5760
tgatccatta aaggtatata tttatttctt gttataat ccttttgttt attacatggg     5820
ctggatacat aaaggtattt tgatttaatt ttttgcttaa attcaatccc cctcgttca    5880 gtgtcaactg taatggtagg aaattaccat acttttgaag aagcaaaaaa aatgaaagaa   5940 aaaaaaatc gtatttccag gttagacgtt ccgcagaatc tagaatgcgg tatgcggtac    6000
attgttcttc gaacgtaaaa gttgcgctcc ctgagatatt gtacattttt gcttttacaa   6060
gtacaagtac atcgtacaac tatgtactac tgttgatgca tccacaacag tttgttttgt   6120
ttttttttgt ttttttttt tctaatgatt cattaccgct atgtatacct acttgtactt    6180
gtagtaagcc gggttattgg cgttcaatta atcatagact tatgaatctg cacggtgtgc   6240
gctgcgagtt acttttagct tatgcatgct acttgggtgt aatattggga tctgttcgga   6300
```

```
aatcaacgga tgctcaaccg atttcgacag taataatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaagaaat acagttcttt gtatcatttg taacaattac cctgtacaaa     6600
ctaaggtatt gaaatcccac aatattccca aagtccaccc cttcccaaat tgtcatgcct    6660
acaactcata taccaagcac taacctacca aacaccacta aaccccaca aaatatatct     6720
taccgaatat acagtaacaa gctaccacca cactcgttgg gtgcagtcgc agcttaaag     6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg cccttttat agagtcttat     7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatggggt tgaccttctg cttgccgaga    7320
tcggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctgggggaat    7560
tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagataccct cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga gtcgccgcc gagaagaaca atcttcttgg agtcagtctt ggtcttctta    8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
ctaaacctcc gaagattgtg actcaggtag tgcggtatcg gctagggacc caaaccttgt    8400
cgatgccgat agcgctatcg aacgtacccc agccggccgg gagtatgtcg gaggggacat    8460
acgagatcgt caagggtttg tggccaactg gtaaataaat gatgtcgacg tttaaacgaa    8520
ttcgccctat cgattctctcc caccaccacc aacactccct ttccattccc acaccgttcc    8580
tctctcgtgc gtcatccttg cgcaatcatc ttcgtctgcg acatattgta cgacatacag    8640
taccacggaa cgtttcagac cgtcgacgtg aacacatctt aggaacagca acctgagcta    8700
```

```
cagaaatcta tctataggcg ataaaaaaa cgcacccact gctcgtcctc cttgctcctc    8760
gaaaccgact cctctacaca cgtcaaatcc gaggttgaaa tcttccccac atttggcagc    8820
caaaccagca catcccagca acctcgcaca gcgccgaaat cgacctgtcg acttggccac    8880
aaaaaaaagc accggctctg caacagttct cacgaccaat tacgtacaag tacgaaatcg    8940
ttcgtggacc gtgactgata agctcccact ttttcttcta acaacaggca acagacaagt    9000
cacacaaaac aaaagc                                                    9016
```

<210> SEQ ID NO 8
<211> LENGTH: 484
<212> TYPE: DNA
<213> ORGANISM: Yarrowia lipolytica

<400> SEQUENCE: 8

```
tttctcccac caccaccaac actcccttc cattcccaca ccgttcctct ctcgtgcgtc     60
atccttgcgc aatcatcttc gtctgcgaca tattgtacga catacagtac cacgaaacgt    120
ttcagaccgt cgacgtgaac acatcttagg aacagcaacc tgagctacag aaatctatct    180
ataggcggat aaaaaaacgc acccactgct cgtcctcctt gctcctcgaa accgactcct    240
ctacacacgt caaatccgag gttgaaatct tccccacatt tggcagccaa accagcacat    300
cccagcaacc tcgcacagcg ccgaaatcga cctgtcgact tggccacaaa aaaagcacc    360 ggctctgcaa cagttctcac gaccaattac gtacaagtac gaaatcgttc gtggaccgtg    420
actgataagc tcccactttt tcttctaaca acaggcaaca gacaagtcac acaaaacaaa    480
agcc                                                                 484
```

<210> SEQ ID NO 9
<211> LENGTH: 8847
<212> TYPE: DNA
<213> ORGANISM: Artificial Sequence
<220> FEATURE:
<223> OTHER INFORMATION: Plasmid pDG2SP2GUS

<400> SEQUENCE: 9

```
aaacagcaac ctgagctaca gaaatctatc tataggcgga taaaaaaacg cacccactgc     60
tcgtcctcct tgctcctcga aaccgactcc tctacacacg tcaaatccga ggttgaaatc    120
ttccccacat ttggcagcca aaccagcaca tcccagcaac ctcgcacagc gccgaaatcg    180
acctgtcgac ttggccacaa aaaaagcac cggctctgca acagttctca cgaccaatta    240
cgtacaagta cgaaatcgtt cgtggaccgt gactgataag ctcccacttt tcttctaac    300 aacaggcaac agacaagtca cacaaaacaa agccatggc atggatggta cgtcctgtag    360
aaaccccaac ccgtgaaatc aaaaaactcg acggcctgtg gcattcagt ctggatcgcg    420 aaaactgtgg aattgatcag cgttggtggg aaagcgcgtt acaagaaagc cgggcaattg    480
ctgtgccagg cagttttaac gatcagttcg ccgatgcaga tattcgtaat tatgcgggca    540
acgtctggta tcagcgcgaa gtctttatac cgaaaggttg gcaggccag cgtatcgtgc    600 tgcgtttcga tgcggtcact cattacggca agtgtgggt caataatcag gaagtgatgg    660
agcatcaggc ggctatacg ccatttgaag ccgatgtcac gccgtatgtt attgccggga    720
aaagtgtacg tatcaccgtt tgtgtgaaca cgaactgaa ctggcagact atcccgccgg    780
gaatggtgat taccgacgaa aacggcaaga aaaagcagtc ttacttccat gatttcttta    840
actatgccgg gatccatcgc agcgtaatgc tctacaccac gccgaacacc tgggtggacg    900
```

```
atatcaccgt ggtgacgcat gtcgcgcaag actgtaacca cgcgtctgtt gactggcagg     960
tggtggccaa tggtgatgtc agcgttgaac tgcgtgatgc ggatcaacag gtggttgcaa    1020
ctggacaagg cactagcggg actttgcaag tggtgaatcc gcacctctgg caaccgggtg    1080
aaggttatct ctatgaactg tgcgtcacag ccaaaagcca gacagagtgt gatatctacc    1140
cgcttcgcgt cggcatccgg tcagtggcag tgaagggcga acagttcctg attaaccaca    1200
aaccgttcta ctttactggc tttggtcgtc atgaagatgc ggacttacgt ggcaaaggat    1260
tcgataacgt gctgatggtg cacgaccacg cattaatgga ctggattggg gccaactcct    1320
accgtacctc gcattaccct tacgctgaag agatgctcga ctgggcagat gaacatggca    1380
tcgtggtgat tgatgaaact gctgctgtcg gctttaacct ctctttaggc attggtttcg    1440
aagcgggcaa caagccgaaa gaactgtaca gcgaagaggc agtcaacggg aaactcagc     1500
aagcgcactt acaggcgatt aaagagctga tagcgcgtga caaaaaccac caagcgtgg     1560
tgatgtggag tattgccaac gaaccggata cccgtccgca agtgcacggg aatatttcgc    1620
cactggcgga agcaacgcgt aaactcgacc cgacgcgtcc gatcacctgc gtcaatgtaa    1680
tgttctgcga cgctcacacc gataccatca gcgatctctt tgatgtgctg tgcctgaacc    1740
gttattacgg atggtatgtc caaagcggcg atttggaaac ggcagagaag gtactggaaa    1800
aagaacttct ggcctggcag gagaaactgc atcagccgat tatcatcacc gaatacggcg    1860
tggatacgtt agccgggctg cactcaatgt acaccgacat gtggagtgaa gagtatcagt    1920
gtgcatggct ggatatgtat caccgcgtct ttgatcgcgt cagcgccgtc gtcggtgaac    1980
aggtatggaa tttcgccgat tttgcgacct cgcaagcat attgcgcgtt ggcggtaaca    2040
agaaagggat cttcactcgc gaccgcaaac cgaagtcggc ggcttttctg ctgcaaaaac    2100
gctggactgg catgaacttc ggtgaaaaac cgcagcaggg aggcaaacaa tgattaatta    2160
actagagcgg ccgccaccgc ggcccgagat tccggcctct tcggccgcca agcgacccgg    2220
gtggacgtct agaggtacct agcaattaac agatagtttg ccggtgataa ttctcttaac    2280
ctcccacact cctttgacat aacgatttat gtaacgaaac tgaaatttga ccagatattg    2340
tgtccgcggt ggagctccag cttttgttcc ctttagtgag ggttaatttc gagcttggcg    2400
taatcatggt catagctgtt tcctgtgtga aattgttatc cgctcacaat tccacacaac    2460
atacgagccg gaagcataaa gtgtaaagcc tggggtgcct aatgagtgag ctaactcaca    2520
ttaattgcgt tgcgctcact gcccgctttc cagtcgggaa acctgtcgtg ccagctgcat    2580
taatgaatcg gccaacgcgc ggggagaggc ggtttgcgta ttgggcgctc ttccgcttcc    2640
tcgctcactg actcgctgcg ctcggtcgtt cggctgcggc gagcggtatc agctcactca    2700
aaggcggtaa tacggttatc cacagaatca ggggataacg caggaaagaa catgtgagca    2760
aaaggccagc aaaaggccag gaaccgtaaa aaggccgcgt tgctggcgtt tttccatagg    2820
ctccgccccc ctgacgagca tcacaaaaat cgacgctcaa gtcagaggtg gcgaaacccg    2880
acaggactat aaagatacca ggcgtttccc cctggaagct ccctcgtgcg ctctcctgtt    2940
ccgaccctgc cgcttaccgg atacctgtcc gcctttctcc cttcgggaag cgtggcgctt    3000
tctcatagct cacgctgtag gtatctcagt tcggtgtagg tcgttcgctc caagctgggc    3060
tgtgtgcacg aaccccccgt tcagcccgac cgctgcgcct tatccggtaa ctatcgtctt    3120
gagtccaacc cggtaagaca cgacttatcg ccactggcag cagccactgg taacaggatt    3180
agcagagcga ggtatgtagg cggtgctaca gagttcttga agtggtggcc taactacggc    3240
tacactagaa ggacagtatt tggtatctgc gctctgctga agccagttac cttcggaaaa    3300
```

-continued

```
agagttggta gctcttgatc cggcaaacaa accaccgctg gtagcggtgg tttttttgtt    3360
tgcaagcagc agattacgcg cagaaaaaaa ggatctcaag aagatccttt gatcttttct    3420
acggggtctg acgctcagtg gaacgaaaac tcacgttaag ggattttggt catgagatta    3480
tcaaaaagga tcttcaccta gatccttttt aattaaaaat gaagttttaa atcaatctaa    3540
agtatatatg agtaaacttg gtctgacagt taccaatgct taatcagtga ggcacctatc    3600
tcagcgatct gtctatttcg ttcatccata gttgcctgac tccccgtcgt gtagataact    3660
acgatacggg agggcttacc atctggcccc agtgctgcaa tgataccgcg agacccacgc    3720
tcaccggctc cagatttatc agcaataaac cagccagccg gaagggccga gcgcagaagt    3780
ggtcctgcaa ctttatccgc ctccatccag tctattaatt gttgccggga agctagagta    3840
agtagttcgc cagttaatag tttgcgcaac gttgttgcca ttgctacagg catcgtggtg    3900
tcacgctcgt cgtttggtat ggcttcattc agctccggtt cccaacgatc aaggcgagtt    3960
acatgatccc ccatgttgtg caaaaaagcg gttagctcct tcggtcctcc gatcgttgtc    4020
agaagtaagt tggccgcagt gttatcactc atggttatgg cagcactgca taattctctt    4080
actgtcatgc catccgtaag atgcttttct gtgactggtg agtactcaac caagtcattc    4140
tgagaatagt gtatgcggcg accgagttgc tcttgcccgg cgtcaatacg ggataatacc    4200
gcgccacata gcagaacttt aaaagtgctc atcattggaa aacgttcttc ggggcgaaaa    4260
ctctcaagga tcttaccgct gttgagatcc agttcgatgt aacccactcg tgcacccaac    4320
tgatcttcag catcttttac tttcaccagc gtttctgggt gagcaaaaac aggaaggcaa    4380
aatgccgcaa aaaagggaat aagggcgaca cggaaatgtt gaatactcat actcttcctt    4440
tttcaatatt attgaagcat ttatcagggt tattgtctca tgagcggata catatttgaa    4500
tgtatttaga aaaataaaca ataggggtt ccgcgcacat ttccccgaaa agtgccacct    4560
gacgcgccct gtagcggcgc attaagcgcg gcgggtgtgg tggttacgcg cagcgtgacc    4620
gctacacttg ccagcgccct agcgcccgct cctttcgctt tcttcccttc ctttctcgcc    4680
acgttcgccg gctttccccg tcaagctcta aatcggggc tccctttagg gttccgattt    4740
agtgctttac ggcacctcga cccaaaaaa cttgattagg gtgatggttc acgtagtggg    4800
ccatcgccct gatagacggt ttttcgccct ttgacgttgg agtccacgtt ctttaatagt    4860
ggactcttgt tccaaactgg aacaacactc aaccctatct cggtctattc ttttgattta    4920
taagggattt tgccgatttc ggcctattgg ttaaaaaatg agctgattta acaaaaattt    4980
aacgcgaatt ttaacaaaat attaacgctt acaatttcca ttcgccattc aggctgcgca    5040
actgttggga agggcgatcg gtgcgggcct cttcgctatt acgccagctg gcgaaagggg    5100
gatgtgctgc aaggcgatta agttgggtaa cgccagggtt ttcccagtca cgacgttgta    5160
aaacgacggc cagtgaattg taatacgact cactataggg cgaattgggt accgggcccc    5220
ccctcgaggt cgatggtgtc gataagcttg atatcgaatt catgtcacac aaaccgatct    5280
tcgcctcaag gaaacctaat tctacatccg agagactgcc gagatccagt ctacactgat    5340
taattttcgg gccaataatt taaaaaaatc gtgttatata atattatatg tattatatat    5400
atacatcatg atgatactga cagtcatgtc ccattgctaa atagacagac tccatctgcc    5460
gcctccaact gatgttctca atatttaagg ggtcatctcg cattgtttaa taataaacag    5520
actccatcta ccgcctccaa atgatgttct caaatatat tgtatgaact tatttttatt    5580
acttagtatt attagacaac ttacttgctt tatgaaaaac acttcctatt taggaaacaa    5640
```

```
tttataatgg cagttcgttc atttaacaat ttatgtagaa taaatgttat aaatgcgtat     5700
gggaaatctt aaatatggat agcataaatg atatctgcat tgcctaattc gaaatcaaca     5760
gcaacgaaaa aaatcccttg tacaacataa atagtcatcg agaaatatca actatcaaag     5820
aacagctatt cacacgttac tattgagatt attattggac gagaatcaca cactcaactg     5880
tctttctctc ttctagaaat acaggtacaa gtatgtacta ttctcattgt tcatacttct     5940
agtcatttca tcccacatat tccttggatt tctctccaat gaatgacatt ctatcttgca     6000
aattcaacaa ttataataag atataccaaa gtagcggtat agtggcaatc aaaaagcttc     6060
tctggtgtgc ttctcgtatt tattttatt ctaatgatcc attaaaggta tatatttatt      6120
tcttgttata taatcctttt gtttattaca tgggctggat acataaaggt attttgattt     6180
aattttttgc ttaaattcaa tccccctcg ttcagtgtca actgtaatgg taggaaatta      6240
ccatactttt gaagaagcaa aaaaatgaa agaaaaaaaa aatcgtattt ccaggttaga      6300
cgttccgcag aatctagaat gcggtatgcg gtacattgtt cttcgaacgt aaaagttgcg     6360
ctccctgaga tattgtacat ttttgctttt acaagtacaa gtacatcgta caactatgta     6420
ctactgttga tgcatccaca acagtttgtt ttgtttttt ttgttttttt tttttctaat      6480
gattcattac cgctatgtat acctacttgt acttgtagta agccgggtta ttggcgttca     6540
attaatcata gacttatgaa tctgcacggt gtgcgctgcg agttacttt agcttatgca      6600 tgctacttgg gtgtaatatt gggatctgtt cggaaatcaa cggatgctca accgatttcg     6660
acagtaataa tttgaatcga atcggagcct aaaatgaacc cgagtatatc tcataaaatt     6720
ctcggtgaga ggtctgtgac tgtcagtaca aggtgcttc attatgccct caaccttacc      6780
atacctcact gaatgtagtg tacctctaaa aatgaaatac agtgccaaaa gccaaggcac     6840
tgagctcgtc taacggactt gatatacaac caattaaaac aaatgaaaag aaatacagtt     6900
ctttgtatca tttgtaacaa ttaccctgta caaactaagg tattgaaatc ccacaatatt     6960
cccaaagtcc accccttcc aaattgtcat gcctacaact catataccaa gcactaacct      7020
accaaacacc actaaaaccc cacaaaatat atcttaccga atatacagta acaagctacc     7080
accacactcg ttgggtgcag tcgccagctt aaagatatct atccacatca gccacaactc     7140
ccttccttta ataaaccgac tacacccttg gctattgagg ttatgagtga atatactgta     7200
gacaagacac tttcaagaag actgtttcca aaacgtacca ctgtcctcca ctacaaacac     7260
acccaatctg cttcttctag tcaaggttgc tacaccggta aattataaat catcatttca     7320
ttagcagggc agggcccttt ttatagagtc ttatacacta gcggaccctg ccggtagacc     7380
aacccgcagg cgcgtcagtt tgctccttcc atcaatgcgt cgtagaaacg acttactcct     7440
tcttgagcag ctccttgacc ttgttggcaa caagtctccg acctcggagg tggaggaaga     7500
gcctccgata tcggcggtag tgataccagc ctcgacggac tccttgacgg cagcctcaac     7560
agcgtcaccg gcgggcttca tgttaagaga gaacttgagc atcatggcgg cagacagaat     7620
ggtggcaatg gggttgacct tctgcttgcc gagatcgggg gcagatccgt gacagggctc     7680
gtacagaccg aacgcctcgt tggtgtcggg cagagaagcc agagaggcgg agggcagcag     7740
acccagagaa ccggggatga cggaggcctc gtcgagatg atatcgccaa acatgttggt     7800
ggtgatgatg ataccattca tcttggaggg ctgcttgatg aggatcatgg cggccgagtc     7860
gatcagctgg tggttgagct cgagctgggg gaattcgtcc ttgaggactc gagtgacagt     7920
cttttcgcca agtcgagagg aggccagcac gttggccttg tcaagagacc acacgggaag     7980 agggggggttg tgctgaaggg ccaggaaggc ggccattcgg gcaattcgct caacctcagg     8040
```

```
aacggagtag gtctcggtgt cggaagcgac gccagatccg tcatcctcct ttcgctctcc      8100
aaagtagata cctccgacga gctctcggac aatgatgaag tcggtgccct caacgtttcg      8160
gatgggggag agatcggcga gcttgggcga cagcagctgg cagggtcgca ggttggcgta      8220
caggttcagg tcctttcgca gcttgaggag accctgctcg ggtcgcacgt cggttcgtcc      8280
gtcgggagtg gtccatacgg tgttggcagc gcctccgaca gcaccgagca taatagagtc      8340
agcctttcgg cagatgtcga gagtagcgtc ggtgatgggc tcgccctcct tctcaatggc      8400
agctcctcca atgagtcggt cctcaaacac aaactcggtg ccggaggcct cagcaacaga      8460
cttgagcacc ttgacggcct cggcaatcac ctcggggcca cagaagtcgc cgccgagaag      8520
aacaatcttc ttggagtcag tcttggtctt cttagtttcg ggttccattg tggatgtgtg      8580
tggttgtatg tgtgatgtgg tgtgtggagt gaaaatctgt ggctggcaaa cgctcttgta      8640
tatatacgca ctttttgcccg tgctatgtgg aagactaaac ctccgaagat tgtgactcag      8700
gtagtgcggt atcggctagg gacccaaacc ttgtcgatgc cgatagcgct atcgaacgta      8760
ccccagccgg ccgggagtat gtcggagggg acatacgaga tcgtcaaggg tttgtggcca      8820
actggtaaat aaatgatgtc gacgttt                                          8847

<210> SEQ ID NO 10
<211> LENGTH: 334
<212> TYPE: DNA
<213> ORGANISM: Yarrowia lipolytica

<400> SEQUENCE: 10
aacagcaacc tgagctacag aaatctatct ataggcggat aaaaaaacgc acccactgct       60
cgtcctcctt gctcctcgaa accgactcct ctacacacgt caaatccgag gttgaaatct      120
tccccacatt tggcagccaa accagcacat cccagcaacc tcgcacagcg ccgaaatcga      180
cctgtcgact tggccacaaa aaaagcaccg gctctgcaa cagttctcac gaccaattac       240
gtacaagtac gaaatcgttc gtggaccgtg actgataagc tcccactttt tcttctaaca      300
acaggcaaca gacaagtcac acaaaacaaa agcc                                  334

<210> SEQ ID NO 11
<211> LENGTH: 8768
<212> TYPE: DNA
<213> ORGANISM: Artificial Sequence
<220> FEATURE:
<223> OTHER INFORMATION: Plasmid pDG2SP4GUS

<400> SEQUENCE: 11
aaaccgactc ctctacacac gtcaaatccg aggttgaaat cttccccaca tttggcagcc       60
aaaccagcac atcccagcaa cctcgcacag cgccgaaatc gacctgtcga cttggccaca      120
aaaaaagcca ccggctctgc aacagttctc acgaccaatt acgtacaagt acgaaatcgt      180
tcgtggaccg tgactgataa gctcccactt ttcttctaa caacaggcaa cagacaagtc      240
acacaaaaca aaagccatgg catggatggt acgtcctgta gaaaccccaa cccgtgaaat      300 caaaaactc gacggcctgt gggcattcag tctggatcgc gaaaactgtg gaattgatca       360
gcgttggtgg gaaagcgcgt tacaagaaag ccgggcaatt gctgtgccag gcagttttaa      420
cgatcagttc gccgatgcag atattcgtaa ttatgcgggc aacgtctggt atcagcgcga      480
agtctttata ccgaaaggtt gggcaggcca gcgtatcgtg ctgcgtttcg atgcggtcac      540
tcattacggc aaagtgtggg tcaataatca ggaagtgatg gagcatcagg gcggctatac      600
```

```
gccatttgaa gccgatgtca cgccgtatgt tattgccggg aaaagtgtac gtatcaccgt    660
ttgtgtgaac aacgaactga actggcagac tatcccgccg ggaatggtga ttaccgacga    720
aaacggcaag aaaaagcagt cttacttcca tgatttcttt aactatgccg ggatccatcg    780
cagcgtaatg ctctacacca cgccgaacac ctgggtggac gatatcaccg tggtgacgca    840
tgtcgcgcaa gactgtaacc acgcgtctgt tgactggcag gtggtggcca atggtgatgt    900
cagcgttgaa ctgcgtgatg cggatcaaca ggtggttgca actggacaag cactagcgg     960 gactttgcaa gtggtgaatc cgcacctctg caaccgggt gaaggttatc tctatgaact    1020
gtgcgtcaca gccaaaagcc agacagagtg tgatatctac ccgcttcgcg tcggcatccg   1080
gtcagtggca gtgaagggcg aacagttcct gattaaccac aaaccgttct actttactgg   1140 cttttggtcgt catgaagatg cggacttacg tggcaaagga ttcgataacg tgctgatggt  1200
gcacgaccac gcattaatgg actggattgg ggccaactcc taccgtacct cgcattaccc   1260
ttacgctgaa gagatgctcg actgggcaga tgaacatggc atcgtggtga ttgatgaaac   1320
tgctgctgtc ggctttaacc tctctttagg cattggtttc gaagcgggca acaagccgaa   1380
agaactgtac agcgaagagg cagtcaacgg ggaaactcag caagcgcact acaggcgat    1440 taaagagctg atagcgcgtg acaaaaacca cccaagcgtg gtgatgtgga gtattgccaa   1500
cgaaccggat acccgtccgc aagtgcacgg gaatatttcg ccactggcgg aagcaacgcg   1560
taaactcgac ccgacgcgtc cgatcacctg cgtcaatgta atgttctgcg acgctcacac   1620
cgataccatc agcgatctct ttgatgtgct gtgcctgaac cgttattacg gatggtatgt   1680
ccaaagcgga gatttggaaa cggcagagaa ggtactggaa aaagaacttc tggcctggca   1740
ggagaaactg catcagccga ttatcatcac cgaatacggc gtggatacgt agccgggct    1800 gcactcaatg tacaccgaca tgtggagtga agagtatcag tgtgcatggc tggatatgta   1860
tcaccgcgtc tttgatcgcg tcagcgccgt cgtcggtgaa caggtatgga atttcgccga   1920
ttttgcgacc tcgcaaggca tattgcgcgt tggcggtaac aagaaaggga tcttcactcg   1980
cgaccgcaaa ccgaagtcgg cggctttttct gctgcaaaaa cgctggactg catgaactt    2040 cggtgaaaaa ccgcagcagg gaggcaaaca atgattaatt aactagagcg ccgccaccg    2100 cggcccgaga ttccggcctc ttcggccgcc aagcgacccg ggtggacgtc tagaggtacc   2160
tagcaattaa cagatagttt gccggtgata attctcttaa cctcccacac tcctttgaca   2220
taacgattta tgtaacgaaa ctgaaatttg accagatatt gtgtccgcgg tggagctcca   2280
gcttttgttc cctttagtga gggttaattt cgagcttggc gtaatcatgg tcatagctgt   2340
ttcctgtgtg aaattgttat ccgctcacaa ttccacacaa catacgagcc ggaagcataa   2400
agtgtaaagc ctggggtgcc taatgagtga gctaactcac attaattgcg ttgcgctcac   2460
tgcccgcttt ccagtcggga aacctgtcgt gccagctgca ttaatgaatc ggccaacgcg   2520
cggggagagg cggtttgcgt attgggcgct cttccgcttc ctcgctcact gactcgctgc   2580
gctcggtcgt tcggctgcgg cgagcggtat cagctcactc aaaggcggta atacggttat   2640
ccacagaatc aggggataac gcaggaaaga acatgtgagc aaaaggccag caaaaggcca   2700
ggaaccgtaa aaaggccgcg ttgctggcgt ttttccatag gctccgcccc cctgacgagc   2760
atcacaaaaa tcgacgctca agtcagaggt ggcgaaaccc gacaggacta taaagatacc   2820
aggcgtttcc ccctggaagc tccctcgtgc gctctcctgt tccgaccctg ccgcttaccg   2880
gatacctgtc cgcctttctc ccttcgggaa gcgtggcgct ttctcatagc tcacgctgta   2940
ggtatctcag ttcggtgtag tcgttcgct ccaagctggg ctgtgtgcac gaaccccccg     3000
```

| | |
|---|---|
| ttcagcccga ccgctgcgcc ttatccggta actatcgtct tgagtccaac ccggtaagac | 3060 |
| acgacttatc gccactggca gcagccactg gtaacaggat tagcagagcg aggtatgtag | 3120 |
| gcggtgctac agagttcttg aagtggtggc ctaactacgg ctacactaga aggacagtat | 3180 |
| ttggtatctg cgctctgctg aagccagtta ccttcggaaa aagagttggt agctcttgat | 3240 |
| ccggcaaaca aaccaccgct ggtagcggtg gttttttgt ttgcaagcag cagattacgc | 3300 |
| gcagaaaaaa aggatctcaa gaagatcctt tgatctttc tacggggtct gacgctcagt | 3360 |
| ggaacgaaaa ctcacgttaa gggattttgg tcatgagatt atcaaaaagg atcttcacct | 3420 |
| agatccttt aaattaaaaa tgaagtttta atcaatcta agtatatat gagtaaactt | 3480 |
| ggtctgacag ttaccaatgc ttaatcagtg aggcacctat ctcagcgatc tgtctatttc | 3540 |
| gttcatccat agttgcctga ctccccgtcg tgtagataac tacgatacgg gagggcttac | 3600 |
| catctggccc cagtgctgca atgataccgc gagacccacg ctcaccggct ccagatttat | 3660 |
| cagcaataaa ccagccagcc ggaagggccg agcgcagaag tggtcctgca actttatccg | 3720 |
| cctccatcca gtctattaat tgttgccggg aagctagagt aagtagttcg ccagttaata | 3780 |
| gtttgcgcaa cgttgttgcc attgctacag gcatcgtggt gtcacgctcg tcgtttggta | 3840 |
| tggcttcatt cagctccggt tcccaacgat caaggcgagt tacatgatcc cccatgttgt | 3900 |
| gcaaaaaagc ggttagctcc ttcggtcctc cgatcgttgt cagaagtaag ttggccgcag | 3960 |
| tgttatcact catggttatg gcagcactgc ataattctct tactgtcatg ccatccgtaa | 4020 |
| gatgcttttc tgtgactggt gagtactcaa ccaagtcatt ctgagaatag tgtatgcggc | 4080 |
| gaccgagttg ctcttgcccg gcgtcaatac gggataatac cgcgccacat agcagaactt | 4140 |
| taaaagtgct catcattgga aaacgttctt cggggcgaaa actctcaagg atcttaccgc | 4200 |
| tgttgagatc cagttcgatg taacccactc gtgcacccaa ctgatcttca gcatctttta | 4260 |
| ctttcaccag cgtttctggg tgagcaaaaa caggaaggca aaatgccgca aaaagggaa | 4320 |
| taagggcgac acggaaatgt tgaatactca tactcttcct ttttcaatat tattgaagca | 4380 |
| tttatcaggg ttattgtctc atgagcggat acatatttga atgtatttag aaaaataaac | 4440 |
| aaatagggt tccgcgcaca tttccccgaa aagtgccacc tgacgcgccc tgtagcggcg | 4500 |
| cattaagcgc ggcgggtgtg gtggttacgc gcagcgtgac cgctacactt gccagcgccc | 4560 |
| tagcgcccgc tcctttcgct ttcttccctt cctttctcgc cacgttcgcc ggctttcccc | 4620 |
| gtcaagctct aaatcggggg ctccctttag ggttccgatt tagtgcttta cggcacctcg | 4680 |
| accccaaaaa acttgattag ggtgatggtt cacgtagtgg gccatcgccc tgatagacgg | 4740 |
| tttttcgccc tttgacgttg gagtccacgt tctttaatag tggactcttg ttccaaactg | 4800 |
| gaacaacact caaccctatc tcggtctatt cttttgattt ataagggatt ttgccgattt | 4860 |
| cggcctattg gttaaaaaat gagctgattt aacaaaaatt taacgcgaat tttaacaaaa | 4920 |
| tattaacgct tacaatttcc attcgccatt caggctgcgc aactgttggg aagggcgatc | 4980 |
| ggtgcgggcc tcttcgctat tacgccagct ggcgaaaggg ggatgtgctg caaggcgatt | 5040 |
| aagttgggta acgccagggt tttcccagtc acgacgttgt aaaacgacgg ccagtgaatt | 5100 |
| gtaatacgac tcactatagg gcgaattggg taccgggccc cccctcgagg tcgatggtgt | 5160 |
| cgataagctt gatatcgaat tcatgtcaca caaaccgatc ttcgcctcaa ggaaacctaa | 5220 |
| ttctacatcc gagagactgc cgagatccag tctacactga ttaattttcg gccaataat | 5280 |
| ttaaaaaaat cgtgttatat aatattatat gtattatata tatacatcat gatgatactg | 5340 |

```
acagtcatgt cccattgcta aatagacaga ctccatctgc cgcctccaac tgatgttctc    5400
aatatttaag gggtcatctc gcattgttta ataataaaca gactccatct accgcctcca    5460
aatgatgttc tcaaaatata ttgtatgaac ttattttat tacttagtat tattagacaa     5520
cttacttgct ttatgaaaaa cacttcctat ttaggaaaca atttataatg gcagttcgtt    5580
catttaacaa tttatgtaga ataaatgtta taaatgcgta tgggaaatct taaatatgga    5640
tagcataaat gatatctgca ttgcctaatt cgaaatcaac agcaacgaaa aaatcccctt    5700
gtacaacata aatagtcatc gagaaatatc aactatcaaa gaacagctat tcacacgtta    5760
ctattgagat tattattgga cgagaatcac acactcaact gtctttctct cttctagaaa    5820
tacaggtaca agtatgtact attctcattg ttcatacttc tagtcatttc atcccacata    5880
ttccttggat ttctctccaa tgaatgacat tctatcttgc aaattcaaca attataataa    5940
gatataccaa agtagcggta tagtggcaat caaaaagctt ctctggtgtg cttctcgtat    6000 ttattttat tctaatgatc cattaaaggt atatatttat ttcttgttat ataatccttt     6060
tgtttattac atgggctgga tacataaagg tattttgatt taattttttg cttaaattca    6120 atccccctc gttcagtgtc aactgtaatg gtaggaaatt accatacttt tgaagaagca     6180 aaaaaatga aagaaaaaa aatcgtatt tccaggttag acgttccgca gaatctagaa        6240
tgcggtatgc ggtacattgt tcttcgaacg taaaagttgc gctccctgag atattgtaca    6300
tttttgcttt tacaagtaca agtacatcgt acaactatgt actactgttg atgcatccac    6360
aacagtttgt tttgtttttt tttgtttttt tttttctaa tgattcatta ccgctatgta     6420
tacctacttg tacttgtagt aagccgggtt attggcgttc aattaatcat agacttatga    6480
atctgcacgg tgtgcgctgc gagttacttt tagcttatgc atgctacttg ggtgtaatat    6540
tgggatctgt tcggaaatca acggatgctc aaccgatttc gacagtaata atttgaatcg    6600
aatcggagcc taaaatgaac ccgagtatat ctcataaaat tctcggtgag aggtctgtga    6660
ctgtcagtac aaggtgcctt cattatgccc tcaaccttac catacctcac tgaatgtagt    6720
gtacctctaa aaatgaaata cagtgccaaa agccaaggca ctgagctcgt ctaacggact    6780
tgatatacaa ccaattaaaa caaatgaaaa gaaatacagt tctttgtatc atttgtaaca    6840
attaccctgt acaaactaag gtattgaaat cccacaatat tcccaaagtc caccccttc     6900 caaattgtca tgcctacaac tcatatacca agcactaacc taccaaacac cactaaaacc    6960
ccacaaaata tatcttaccg aatatacagt aacaagctac caccacactc gttgggtgca    7020
gtcgccagct taaagatatc tatccacatc agccacaact cccttccttt aataaaccga    7080
ctacaccctt ggctattgag gttatgagtg aatatactgt agacaagaca ctttcaagaa    7140
gactgtttcc aaaacgtacc actgtcctcc actacaaaca cacccaatct gcttcttcta    7200
gtcaaggttg ctacaccggt aaattataaa tcatcatttc attagcaggg cagggcccctt   7260 tttatagagt cttatacact agcggaccct gccggtagac caacccgcag gcgcgtcagt    7320
ttgctccttc catcaatgcg tcgtagaaac gacttactcc ttcttgagca gctccttgac    7380
cttgttggca acaagtctcc gacctcggag gtggaggaag agcctccgat atcggcggta    7440
gtgataccag cctcgacgga ctccttgacg gcagcctcaa cagcgtcacc ggcgggcttc    7500
atgttaagag agaacttgag catcatggcg gcagacagaa tggtggcaat ggggttgacc    7560
ttctgcttgc cgagatcggg ggcagatccg tgacagggct cgtacagacc gaacgcctcg    7620
ttggtgtcgg gcagagaagc cagagaggcg gagggcagca gacccagaga accggggatg    7680
acggaggcct cgtcggagat gatatcgcca aacatgttgg tggtgatgat gataccattc    7740
```

```
atcttggagg gctgcttgat gaggatcatg gcggccgagt cgatcagctg gtggttgagc    7800
tcgagctggg ggaattcgtc cttgaggact cgagtgacag tctttcgcca aagtcgagag    7860
gaggccagca cgttggcctt gtcaagagac cacacgggaa aggggggtt gtgctgaagg     7920 gccaggaagg cggccattcg ggcaattcgc tcaacctcag gaacgagta ggtctcggtg     7980 tcggaagcga cgccagatcc gtcatcctcc tttcgctctc caaagtagat acctccgacg    8040
agctctcgga caatgatgaa gtcggtgccc tcaacgtttc ggatggggga gagatcggcg    8100
agcttgggcg acagcagctg gcagggtcgc aggttggcgt acaggttcag gtcctttcgc    8160
agcttgagga gaccctgctc gggtcgcacg tcggttcgtc cgtcgggagt ggtccatacg    8220
gtgttggcag cgcctccgac agcaccgagc ataatagagt cagccttcg gcagatgtcg      8280 agagtagcgt cggtgatggg ctcgccctcc ttctcaatgg cagctcctcc aatgagtcgg    8340
tcctcaaaca caaactcggt gccggaggcc tcagcaacag acttgagcac cttgacggcc    8400
tcggcaatca cctcggggcc acagaagtcg ccgccgagaa gaacaatctt cttggagtca    8460
gtcttggtct tcttagtttc gggttccatt gtggatgtgt gtggttgtat gtgtgatgtg    8520
gtgtgtggag tgaaaatctg tggctggcaa acgctcttgt atatatacgc acttttgccc    8580
gtgctatgtg gaagactaaa cctccgaaga ttgtgactca ggtagtgcgg tatcggctag    8640
ggacccaaac cttgtcgatg ccgatagcgc tatcgaacgt accccagccg gcgggagta     8700 tgtcggaggg gacatacgag atcgtcaagg gtttgtggcc aactggtaaa taaatgatgt    8760
cgacgttt                                                             8768

<210> SEQ ID NO 12
<211> LENGTH: 256
<212> TYPE: DNA
<213> ORGANISM: Yarrowia lipolytica

<400> SEQUENCE: 12
aaaccgactc ctctacacac gtcaaatccg aggttgaaat cttccccaca tttggcagcc     60
aaaccagcac atcccagcaa cctcgcacag cgccgaaatc gacctgtcga cttggccaca    120
aaaaaaagca ccggctctgc aacagttctc acgaccaatt acgtacaagt acgaaatcgt    180
tcgtggaccg tgactgataa gctcccactt tttcttctaa caacaggcaa cagacaagtc    240
acacaaaaca aaagcc                                                    256

<210> SEQ ID NO 13
<211> LENGTH: 1000
<212> TYPE: DNA
<213> ORGANISM: Yarrowia lipolytica

<400> SEQUENCE: 13
atgctgcggg cggatcctgg tgcatttttg cttgcgattg ttgtgaaaat tagcacggtt     60
atattagccc gtaataaatg cccgtctcca tcttcatatg gccatcaccc cgcaaatagc    120
cggccaatca ggcgtatgtc acctgttgct cacacgcatg tcctcggacc gttgtattgt    180
gcaagtaggg gtacctcccc gatccatcct cgaccagtgg cacgctcaac cccatggttc    240
gcttttctct tttcgtctat cctgaactga gttttttcc acgccaactg atatcccctt     300
acgttacccc ctcatcacct ggtgaggcga aactgtaagg tgaaagctaa aaatgacatc    360
tcagctgcac gaaggaccgg ggcttaaaag acgggctggt gcttgtgatt taaaactgga    420
caaatctcag cttgcttgaa atttggtct ccaactgttt ccgagcgaat cgcacacaaa     480
```

| | |
|---|---|
| ccgggcttct ctctgcagac cacgccccg aaactctttc tcccaccacc accaacactc | 540 |
| cctttccatt cccacaccgt tcctctctcg tgcgtcatcc ttgcgcaatc atcttcgtct | 600 |
| gcgacatatt gtacgacata cagtaccacg gaacgtttca gaccgtcgac gtgaacacat | 660 |
| cttaggaaca gcaacctgag ctacagaaat ctatctatag gcggataaaa aaacgcaccc | 720 |
| actgctcgtc ctccttgctc ctcgaaaccg actcctctac acacgtcaaa tccgaggttg | 780 |
| aaatcttccc cacatttggc agccaaacca gcacatccca gcaacctcgc acagcgccga | 840 |
| aatcgacctg tcgacttggc cacaaaaaaa agcaccggct ctgcaacagt tctcacgacc | 900 |
| aattacgtac aagtacgaaa tcgttcgtgg accgtgactg ataagctccc acttttctt | 960 |
| ctaacaacag gcaacagaca agtcacacaa aacaaaagct | 1000 |

<210> SEQ ID NO 14
<211> LENGTH: 31
<212> TYPE: DNA
<213> ORGANISM: Artificial Sequence
<220> FEATURE:
<223> OTHER INFORMATION: Primer Y1189

<400> SEQUENCE: 14

| | |
|---|---|
| tccaatcgat tgttgtgaaa attagcacgg t | 31 |

<210> SEQ ID NO 15
<211> LENGTH: 37
<212> TYPE: DNA
<213> ORGANISM: Artificial Sequence
<220> FEATURE:
<223> OTHER INFORMATION: Primer Y1191

<400> SEQUENCE: 15

| | |
|---|---|
| ctttccatgg cttttgtttt gtgtgacttg tctgttg | 37 |

<210> SEQ ID NO 16
<211> LENGTH: 37
<212> TYPE: DNA
<213> ORGANISM: Artificial Sequence
<220> FEATURE:
<223> OTHER INFORMATION: Primer Y1190

<400> SEQUENCE: 16

| | |
|---|---|
| tccaatcgat ttctcccacc accaacaa ctccctt | 37 |

<210> SEQ ID NO 17
<211> LENGTH: 4936
<212> TYPE: DNA
<213> ORGANISM: Artificial Sequence
<220> FEATURE:
<223> OTHER INFORMATION: Plasmid pT-DG2LPro

<400> SEQUENCE: 17

| | |
|---|---|
| agcgcccaat acgcaaaccg cctctccccg cgcgttggcc gattcattaa tgcagctggc | 60 |
| acgacaggtt tcccgactgg aaagcgggca gtgagcgcaa cgcaattaat gtgagttagc | 120 |
| tcactcatta ggcaccccag gctttacact ttatgcttcc ggctcgtatg ttgtgtggaa | 180 |
| ttgtgagcgg ataacaattt cacacaggaa acagctatga ccatgattac gccaagctca | 240 |
| gaattaaccc tcactaaagg gactagtcct gcaggtttaa acgaattcgc cttccaatc | 300 |
| gattgttgtg aaaattagca cggttatatt agcccgtaat aaatgccgt ctccatcttc | 360 |
| atatggccat caccccgcaa atagccggcc aatcaggcgt atgtcacctg ttgctcacac | 420 |
| gcatgtcctc ggaccgttgt attgtgcaag taggggtacc tccccgatcc atcctcgacc | 480 |

```
agtggcacgc tcaaccccat ggttcgcttt tctcttttcg tctatcctga actgagtttt    540
tttccacgcc aactgatatc cccttacgtt accccctcat cacctggtga ggcgaaactg    600
taaggtgaaa gctaaaaatg acatctcagc tgcacgaagg accggggctt aaaagacggg    660
ctggtgcttg tgatttaaaa ctggacaaat ctcagcttgc ttgaaatttt ggtctccaac    720
tgtttccgag cgaatcgcac acaaaccggg cttctctctg cagaccacgc ccccgaaact    780
ctttctccca ccaccaccaa cactcccttt ccattcccac accgttcctc tctcgtgcgt    840
catccttgcg caatcatctt cgtctgcgac atattgtacg acatacagta ccacggaacg    900
tttcagaccg tcgacgtgaa cacatcttag gaacagcaac ctgagctaca gaaatctatc    960
tataggcgga taaaaaaacg cacccactgc tcgtcctcct tgctcctcga aaccgactcc   1020
tctacacacg tcaaatccga ggttgaaatc ttccccacat ttggcagcca aaccagcaca   1080
tcccagcaac ctcgcacagc gccgaaatcg acctgtcgac ttggccacaa aaaaaagcac   1140
cggctctgca acagttctca cgaccaatta cgtacaagta cgaaatcgtt cgtggaccgt   1200
gactgataag ctcccacttt ttcttctaac aacaggcaac agacaagtca cacaaaacaa   1260
aagccatgga aagtaagggc gaattcgcgg ccgctaaatt caattcgccc tatagtgagt   1320
cgtattacaa ttcactggcc gtcgttttac aacgtcgtga ctgggaaaac cctggcgtta   1380
cccaacttaa tcgccttgca gcacatcccc ctttcgccag ctggcgtaat agcgaagagg   1440
cccgcaccga tcgcccttcc caacagttgc gcagcctata cgtacggcag tttaaggttt   1500
acacctataa aagagagagc cgttatcgtc tgtttgtgga tgtacagagt gatattattg   1560
acacgccggg cgacggatg tgatccccc tggccagtgc acgtctgctg tcagataaag   1620
tctcccgtga actttacccg gtggtgcata tcggggatga agctggcgc atgatgacca   1680 ccgatatggc cagtgtgccg gtctccgtta tcggggaaga agtggctgat ctcagccacc   1740
gcgaaaatga catcaaaaac gccattaacc tgatgttctg gggaatataa atgtcaggca   1800
tgagattatc aaaaaggatc ttcacctaga tccttttcac gtagaaagcc agtccgcaga   1860
aacggtgctg accccggatg aatgtcagct actgggctat ctggacaagg gaaaacgcaa   1920
gcgcaaagag aaagcaggta gcttgcagtg gcttacatg gcgatagcta gactgggcgg   1980
ttttatggac agcaagcgaa ccggaattgc cagctggggc gccctctggt aaggttggga   2040
agccctgcaa agtaaactgg atggctttct tgccgccaag gatctgatgg cgcagggggat   2100 caagctctga tcaagagaca ggatgaggat cgtttcgcat gattgaacaa gatggattgc   2160
acgcaggttc tccggccgct tgggtggaga ggctattcgg ctatgactgg gcacaacaga   2220
caatcggctg ctctgatgcc gccgtgttcc ggctgtcagc gcaggggcgc ccggttcttt   2280
ttgtcaagac cgacctgtcc ggtgccctga atgaactgca agacgaggca gcgcggctat   2340
cgtggctggc cacgacgggc gttccttgcg cagctgtgct cgacgttgtc actgaagcgg   2400
gaagggactg gctgctattg ggcgaagtgc cggggcagga tctcctgtca tctcaccttg   2460
ctcctgccga gaaagtatcc atcatggctg atgcaatgcg gcggctgcat acgcttgatc   2520
cggctacctg cccattcgac caccaagcga aacatcgcat cgagcgagca cgtactcgga   2580
tggaagccgg tcttgtcgat caggatgatc tggacgaaga gcatcagggg ctcgcgccag   2640
ccgaactgtt cgccaggctc aaggcgagca tgcccgacgg cgaggatctc gtcgtgaccc   2700
atggcgatgc ctgcttgccg aatatcatgg tggaaaatgg ccgcttttct ggattcatcg   2760
actgtggccg gctgggtgtg gcggaccgct atcaggacat agcgttggct acccgtgata   2820
```

```
ttgctgaaga gcttggcggc gaatgggctg accgcttcct cgtgctttac ggtatcgccg    2880
ctcccgattc gcagcgcatc gccttctatc gccttcttga cgagttcttc tgaattatta    2940
acgcttacaa tttcctgatg cggtattttc tccttacgca tctgtgcggt atttcacacc    3000
gcatcaggtg gcacttttcg gggaaatgtg cgcggaaccc ctatttgttt attttttctaa   3060
atacattcaa atatgtatcc gctcatgaga ttatcaaaaa ggatcttcac ctagatcctt    3120
ttaaattaaa aatgaagttt taaatcaatc taaagtatat atgagtaaac ttggtctgac    3180
agttaccaat gcttaatcag tgaggcacct atctcagcga tctgtctatt tcgttcatcc    3240
atagttgcct gactccccgt cgtgtagata actacgatac gggagggctt accatctggc    3300
cccagtgctg caatgatacc gcgagaccca cgctcaccgg ctccagattt atcagcaata    3360
aaccagccag ccggaagggc cgagcgcaga agtggtcctg caactttatc cgcctccatc    3420
cagtctatta attgttgccg ggaagctaga gtaagtagtt cgccagttaa tagtttgcgc    3480
aacgttgttg ccattgctac aggcatcgtg gtgtcacgct cgtcgtttgg tatggcttca    3540
ttcagctccg gttcccaacg atcaaggcga gttacatgat cccccatgtt gtgcaaaaaa    3600
gcggttagct ccttcggtcc tccgatcgtt gtcagaagta agttggccgc agtgttatca    3660
ctcatggtta tggcagcact gcataattct cttactgtca tgccatccgt aagatgcttt    3720
tctgtgactg gtgagtactc aaccaagtca ttctgagaat agtgtatgcg gcgaccgagt    3780
tgctcttgcc cggcgtcaat acgggataat accgcgccac atagcagaac tttaaaagtg    3840
ctcatcattg gaaaacgttc ttcggggcga aaactctcaa ggatcttacc gctgttgaga    3900
tccagttcga tgtaacccac tcgtgcaccc aactgatctt cagcatcttt tactttcacc    3960
agcgtttctg ggtgagcaaa aacaggaagg caaaatgccg caaaaaaggg aataagggcg    4020
acacggaaat gttgaatact catactcttc cttttcaat attattgaag catttatcag    4080
ggttattgtc tcatgaccaa atcccttaa cgtgagtttt cgttccactg agcgtcagac    4140
cccgtagaaa agatcaaagg atcttcttga gatcctttt tctgcgcgt aatctgctgc    4200
ttgcaaacaa aaaaaccacc gctaccagcg gtggtttgtt tgccggatca agagctacca    4260
actcttttc cgaaggtaac tggcttcagc agagcgcaga taccaaatac tgttcttcta    4320
gtgtagccgt agttaggcca ccacttcaag aactctgtag caccgcctac atacctcgct    4380
ctgctaatcc tgttaccagt ggctgctgcc agtggcgata gtcgtgtct taccgggttg    4440
gactcaagac gatagttacc ggataaggcg cagcggtcgg gctgaacggg gggttcgtgc    4500
acacagccca gcttggagcg aacgacctac accgaactga tacctaca gcgtgagcta    4560
tgagaaagcg ccacgcttcc cgaagggaga aaggcggaca ggtatccggt aagcggcagg    4620
gtcggaacag gagagcgcac gagggagctt ccagggggaa acgcctggta tctttatagt    4680
cctgtcgggt ttcgccacct ctgacttgag cgtcgatttt tgtgatgctc gtcaggggggg   4740
cggagcctat ggaaaaacgc cagcaacgcg gcctttttac ggttcctggc cttttgctgg    4800
ccttttgctc acatgttctt tcctgcgtta tcccctgatt ctgtggataa ccgtattacc    4860
gcctttgagt gagctgatac cgctcgccgc agccgaacga ccgagcgcag cgagtcagtg    4920
agcgaggaag cggaag                                                   4936
```

<210> SEQ ID NO 18
<211> LENGTH: 4449
<212> TYPE: DNA
<213> ORGANISM: Artificial Sequence
<220> FEATURE:
<223> OTHER INFORMATION: Plasmid pT-DG2SPro

<400> SEQUENCE: 18

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctca     240
gaattaaccc tcactaaagg gactagtcct gcaggtttaa acgaattcgc cctatcgatt     300
tctcccacca ccaccaacac tccctttcca ttcccacacc gttcctctct cgtgcgtcat     360
ccttgcgcaa tcatcttcgt ctgcgacata ttgtacgaca tacagtacca cggaacgttt     420
cagaccgtcg acgtgaacac atcttaggaa cagcaacctg agctacagaa atctatctat     480
aggcggataa aaaacgcac ccactgctcg tcctccttgc tcctcgaaac cgactcctct     540
acacacgtca atccgaggt tgaaatcttc cccacatttg gcagccaaac cagcacatcc     600
cagcaacctc gcacagcgcc gaaatcgacc tgtcgacttg ccacaaaaa aaagcaccgg     660
ctctgcaaca gttctcacga ccaattacgt acaagtacga atcgttcgt ggaccgtgac      720
tgataagctc ccacttttc ttctaacaac aggcaacaga caagtcacac aaaacaaaag     780
ccatggtaag ggcgaattcg cggccgctaa attcaattcg ccctatagtg agtcgtatta     840
caattcactg gccgtcgttt tacaacgtcg tgactgggaa aaccctggcg ttacccaact     900
taatcgcctt gcagcacatc ccctttcgc cagctggcgt aatagcgaag aggcccgcac     960
cgatcgccct tcccaacagt tgcgcagcct atacgtacgg cagtttaagg tttacaccta    1020
taaaagagag agccgttatc gtctgtttgt ggatgtacag agtgatatta ttgacacgcc    1080
ggggcgacgg atggtgatcc ccctggccag tgcacgtctg ctgtcagata aagtctcccg    1140
tgaactttac ccggtggtgc atatcgggga tgaaagctgg cgcatgatga ccaccgatat    1200
ggccagtgtg ccggtctccg ttatcgggga agaagtggct gatctcagcc accgcgaaaa    1260
tgacatcaaa aacgccatta acctgatgtt ctggggaata taaatgtcag gcatgagatt    1320
atcaaaaagg atcttcacct agatcctttt cacgtagaaa gccagtccgc agaaacggtg    1380
ctgaccccgg atgaatgtca gctactgggc tatctggaca agggaaaacg caagcgcaaa    1440
gagaaagcag gtagcttgca gtgggcttac atggcgatag ctagactggg cggttttatg    1500
gacagcaagc gaaccggaat tgccagctgg ggcgccctct ggtaaggttg ggaagccctg    1560
caaagtaaac tggatggctt tcttgccgcc aaggatctga tggcgcaggg gatcaagctc    1620
tgatcaagag acaggatgag gatcgtttcg catgattgaa caagatggat tgcacgcagg    1680
ttctccggcc gcttgggtgg agaggctatt cggctatgac tgggcacaac agacaatcgg    1740
ctgctctgat gccgccgtgt tccggctgtc agcgcagggg cgcccggttc tttttgtcaa    1800
gaccgacctg tccggtgccc tgaatgaact gcaagacgag gcagcgcggc tatcgtggct    1860
ggccacgacg ggcgttcctt gcgcagctgt gctcgacgtt gtcactgaag cgggaaggga    1920
ctggctgcta ttgggcgaag tgccggggca ggatctcctg tcatctcacc ttgctcctgc    1980
cgagaaagta tccatcatgg ctgatgcaat gcggcggctg catacgcttg atccggctac    2040
ctgcccattc gaccaccaag cgaaacatcg catcgagcga gcacgtactc ggatggaagc    2100
cggtcttgtc gatcaggatg atctggacga agagcatcag gggctcgcgc cagccgaact    2160
gttcgccagg ctcaaggcga gcatgcccga cggcgaggat ctcgtcgtga cccatggcga    2220
tgcctgcttg ccgaatatca tggtggaaaa tggccgcttt tctggattca tcgactgtgg    2280
```

```
ccggctgggt gtggcggacc gctatcagga catagcgttg gctacccgtg atattgctga    2340
agagcttggc ggcgaatggg ctgaccgctt cctcgtgctt tacggtatcg ccgctcccga    2400
ttcgcagcgc atcgccttct atcgccttct tgacgagttc ttctgaatta ttaacgctta    2460
caatttcctg atgcggtatt ttctccttac gcatctgtgc ggtatttcac accgcatcag    2520
gtggcacttt tcggggaaat gtgcgcggaa ccctatttg tttattttc taaatacatt     2580 caaatatgta tccgctcatg agattatcaa aaaggatctt cacctagatc cttttaaatt    2640
aaaaatgaag ttttaaatca atctaaagta tatatgagta aacttggtct gacagttacc    2700
aatgcttaat cagtgaggca cctatctcag cgatctgtct atttcgttca tccatagttg    2760
cctgactccc cgtcgtgtag ataactacga tacgggaggg cttaccatct ggccccagtg    2820
ctgcaatgat accgcgagac ccacgctcac cggctccaga tttatcagca ataaaccagc    2880
cagccggaag ggccgagcgc agaagtggtc ctgcaacttt atccgcctcc atccagtcta    2940
ttaattgttg ccgggaagct agagtaagta gttcgccagt taatagtttg cgcaacgttg    3000
ttgccattgc tacaggcatc gtggtgtcac gctcgtcgtt tggtatggct tcattcagct    3060
ccggttccca acgatcaagg cgagttacat gatcccccat gttgtgcaaa aaagcggtta    3120
gctccttcgg tcctccgatc gttgtcagaa gtaagttggc cgcagtgtta tcactcatgg    3180
ttatggcagc actgcataat tctcttactg tcatgccatc cgtaagatgc ttttctgtga    3240
ctggtgagta ctcaaccaag tcattctgag aatagtgtat gcggcgaccg agttgctctt    3300
gcccggcgtc aatacgggat aataccgcgc cacatagcag aactttaaaa gtgctcatca    3360
ttggaaaacg ttcttcgggg cgaaaactct caaggatctt accgctgttg agatccagtt    3420
cgatgtaacc cactcgtgca cccaactgat cttcagcatc ttttactttc accagcgttt    3480
ctgggtgagc aaaaacagga aggcaaaatg ccgcaaaaaa gggaataagg gcgacacgga    3540
aatgttgaat actcatactc ttccttttc aatattattg aagcatttat cagggttatt    3600
gtctcatgac caaaatccct taacgtgagt tttcgttcca ctgagcgtca ccccgtag     3660 aaaagatcaa aggatcttct tgagatcctt ttttctgcg cgtaatctgc tgcttgcaaa     3720
caaaaaaacc accgctacca gcggtggttt gtttgccgga tcaagagcta ccaactcttt    3780
ttccgaaggt aactggcttc agcagagcgc agataccaaa tactgttctt ctagtgtagc    3840
cgtagttagg ccaccacttc aagaactctg tagcaccgcc tacataccte gctctgctaa    3900 tcctgttacc agtggctgct gccagtggcg ataagtcgtg tcttaccggg ttggactcaa    3960
gacgatagtt accggataag gcgcagcggt cgggctgaac ggggggttcg tgcacacagc    4020
ccagcttgga gcgaacgacc tacaccgaac tgagatacct acagcgtgag ctatgagaaa    4080
gcgccacgct tcccgaaggg agaaaggcgg acaggtatcc ggtaagcggc agggtcggaa    4140
caggagagcg cacgagggag cttccagggg gaaacgcctg gtatctttat agtcctgtcg    4200
ggtttcgcca cctctgactt gagcgtcgat ttttgtgatg ctcgtcaggg gggcggagcc    4260 tatgaaaaa cgccagcaac gcggcctttt tacggttcct ggccttttgc tggccttttg    4320
ctcacatgtt ctttcctgcg ttatcccctg attctgtgga taaccgtatt accgcctttg    4380
agtgagctga taccgctcgc cgcagccgaa cgaccgagcg cagcgagtca gtgagcgagg    4440
aagcggaag                                                            4449
```

<210> SEQ ID NO 19
<211> LENGTH: 966
<212> TYPE: DNA
<213> ORGANISM: Yarrowia lipolytica

<400> SEQUENCE: 19

```
cgattgttgt gaaaattagc acggttatat tagcccgtaa taaatgcccg tctccatctt      60
catatggcca tcaccccgca aatagccggc caatcaggcg tatgtcacct gttgctcaca     120
cgcatgtcct cggaccgttg tattgtgcaa gtaggggtac ctccccgatc catcctcgac     180
cagtggcacg ctcaacccca tggttcgctt ttctcttttc gtctatcctg aactgagttt     240
ttttccacgc caactgatat ccccttacgt taccccctca tcacctggtg aggcgaaact     300
gtaaggtgaa agctaaaaat gacatctcag ctgcacgaag gaccggggct aaaagacgg      360
gctggtgctt gtgatttaaa actggacaaa tctcagcttg cttgaaattt tggtctccaa     420
ctgtttccga gcgaatcgca cacaaaccgg gcttctctct gcagaccacg ccccgaaac      480
tctttctccc accaccacca acactccctt tccattccca caccgttcct ctctcgtgcg     540
tcatccttgc gcaatcatct tcgtctgcga catattgtac gacatacagt accacggaac     600
gtttcagacc gtcgacgtga acacatctta ggaacagcaa cctgagctac agaaatctat     660
ctataggcgg ataaaaaaac gcacccactg ctcgtcctcc ttgctcctcg aaaccgactc     720
ctctacacac gtcaaatccg aggttgaaat cttccccaca tttggcagcc aaaccagcac     780
atcccagcaa cctcgcacag cgccgaaatc gacctgtcga cttggccaca aaaaaaagca     840
ccggctctgc aacagttctc acgaccaatt acgtacaagt acgaaatcgt tcgtggaccg     900
tgactgataa gctcccactt tttcttctaa caacaggcaa cagacaagtc acacaaaaca     960
aaagcc                                                                966
```

<210> SEQ ID NO 20
<211> LENGTH: 4936
<212> TYPE: DNA
<213> ORGANISM: Artificial Sequence
<220> FEATURE:
<223> OTHER INFORMATION: Plasmid pT-DGAT2LPro-(-N)

<400> SEQUENCE: 20

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctca     240
gaattaaccc tcactaaagg gactagtcct gcaggtttaa acgaattcgc cttccaatc      300
gattgttgtg aaaattagca cggttatatt agcccgtaat aaatgcccgt ctccatcttc     360
atatggccat caccccgcaa atagccggcc aatcaggcgt atgtcacctg ttgctcacac     420
gcatgtcctc ggaccgttgt attgtgcaag taggggtacc tccccgatcc atcctcgacc     480
agtggcacgc tcaaccccac ggttcgcttt tctcttttcg tctatcctga actgagtttt     540
tttccacgcc aactgatatc cccttacgtt accccctcat cacctggtga ggcgaaactg     600
taaggtgaaa gctaaaaatg acatctcagc tgcacgaagg accggggctt aaaagacggg     660
ctggtgcttg tgatttaaaa ctggacaaat ctcagcttgc ttgaaatttt ggtctccaac     720
tgtttccgag cgaatcgcac acaaaccggg cttctctctg cagaccacgc cccgaaact      780
ctttctccca ccaccacaa cactcccttt ccattccac accgttcctc tctcgtgcgt      840
catccttgcg caatcatctt cgtctgcgac atattgtacg acatacagta ccacggaacg     900
tttcagaccg tcgacgtgaa cacatcttag gaacagcaac ctgagctaca gaaatctatc     960
```

```
tataggcgga taaaaaaacg cacccactgc tcgtcctcct tgctcctcga aaccgactcc   1020
tctacacacg tcaaatccga ggttgaaatc ttccccacat ttggcagcca aaccagcaca   1080
tcccagcaac ctcgcacagc gccgaaatcg acctgtcgac ttggccacaa aaaaagcac    1140 cggctctgca acagttctca cgaccaatta cgtacaagta cgaaatcgtt cgtggaccgt   1200
gactgataag ctcccacttt ttcttctaac aacaggcaac agacaagtca cacaaaacaa   1260
aagccatgga aagtaagggc gaattcgcgg ccgctaaatt caattcgccc tatagtgagt   1320
cgtattacaa ttcactggcc gtcgttttac aacgtcgtga ctgggaaaac cctggcgtta   1380
cccaacttaa tcgccttgca gcacatcccc ctttcgccag ctggcgtaat agcgaagagg   1440
cccgcaccga tcgcccttcc caacagttgc gcagcctata cgtacggcag tttaaggttt   1500
acacctataa aagagagagc cgttatcgtc tgtttgtgga tgtacagagt gatattattg   1560
acacgccggg gcgacggatg gtgatccccc tggccagtgc acgtctgctg tcagataaag   1620
tctcccgtga actttacccg gtggtgcata tcgggatga aagctggcgc atgatgacca    1680
ccgatatggc cagtgtgccg gtctccgtta tcggggaaga agtggctgat ctcagccacc   1740
gcgaaaatga catcaaaaac gccattaacc tgatgttctg gggaatataa atgtcaggca   1800
tgagattatc aaaaaggatc ttcacctaga tccttttcac gtagaaagcc agtccgcaga   1860
aacggtgctg accccggatg aatgtcagct actgggctat ctggacaagg gaaaacgcaa   1920
gcgcaaagag aaagcaggta gcttgcagtg ggcttacatg gcgatagcta actgggcgg    1980 ttttatggac agcaagcgaa ccggaattgc cagctggggc gccctctggt aaggttggga   2040
agccctgcaa agtaaactgg atggctttct tgccgccaag gatctgatgg cgcaggggat   2100
caagctctga tcaagagaca ggatgaggat cgtttcgcat gattgaacaa gatggattgc   2160
acgcaggttc tccggccgct tgggtggaga ggctattcgg ctatgactgg gcacaacaga   2220
caatcggctg ctctgatgcc gccgtgttcc ggctgtcagc gcaggggcgc ccggttcttt   2280
ttgtcaagac cgacctgtcc ggtgccctga atgaactgca agacgaggca gcgcggctat   2340
cgtggctggc cacgacgggc gttccttgcg cagctgtgct cgacgttgtc actgaagcgg   2400
gaagggactg gctgctattg ggcgaagtgc cggggcagga tctcctgtca tctcaccttg   2460
ctcctgccga gaaagtatcc atcatggctg atgcaatgcg gcggctgcat acgcttgatc   2520
cggctacctg cccattcgac caccaagcga aacatcgcat cgagcgagca cgtactcgga   2580
tggaagccgg tcttgtcgat caggatgatc tggacgaaga gcatcagggg ctcgcgccag   2640
ccgaactgtt cgccaggctc aaggcgagca tgcccgacgg cgaggatctc gtcgtgaccc   2700
atggcgatgc ctgcttgccg aatatcatgg tggaaaatgg ccgcttttct ggattcatcg   2760
actgtggccg gctgggtgtg gcggaccgct atcaggacat agcgttggct acccgtgata   2820
ttgctgaaga gcttggcggc gaatgggctg accgcttcct cgtgctttac ggtatcgccg   2880
ctcccgattc gcagcgcatc gccttctatc gccttcttga cgagttcttc tgaattatta   2940
acgcttacaa tttcctgatg cggtatttc tccttacgca tctgtgcggt atttcacacc   3000
gcatcaggtg gcacttttcg gggaaatgtg cgcggaaccc ctatttgttt attttttctaa   3060 atacattcaa atatgtatcc gctcatgaga ttatcaaaaa ggatcttcac ctagatcctt   3120
ttaaattaaa aatgaagttt taaatcaatc taaagtatat atgagtaaac ttggtctgac   3180
agttaccaat gcttaatcag tgaggcacct atctcagcga tctgtctatt tcgttcatcc   3240
atagttgcct gactccccgt cgtgtagata actacgatac gggagggctt accatctggc   3300
cccagtgctg caatgatacc gcgagaccca cgctcaccgg ctccagattt atcagcaata   3360
```

```
aaccagccag ccggaagggc cgagcgcaga agtggtcctg caactttatc cgcctccatc   3420
cagtctatta attgttgccg ggaagctaga gtaagtagtt cgccagttaa tagtttgcgc   3480
aacgttgttg ccattgctac aggcatcgtg gtgtcacgct cgtcgtttgg tatggcttca   3540
ttcagctccg gttcccaacg atcaaggcga gttacatgat cccccatgtt gtgcaaaaaa   3600
gcggttagct ccttcggtcc tccgatcgtt gtcagaagta agttggccgc agtgttatca   3660
ctcatggtta tggcagcact gcataattct cttactgtca tgccatccgt aagatgcttt   3720
tctgtgactg gtgagtactc aaccaagtca ttctgagaat agtgtatgcg cgaccgagt   3780 tgctcttgcc cggcgtcaat acgggataat accgcgccac atagcagaac tttaaaagtg   3840
ctcatcattg gaaaacgttc ttcggggcga aaactctcaa ggatcttacc gctgttgaga   3900
tccagttcga tgtaacccac tcgtgcaccc aactgatctt cagcatcttt tactttcacc   3960
agcgtttctg ggtgagcaaa aacaggaagg caaaatgccg caaaaaaggg aataagggcg   4020
acacggaaat gttgaatact catactcttc cttttcaat attattgaag catttatcag   4080
ggttattgtc tcatgaccaa aatcccttaa cgtgagtttt cgttccactg agcgtcagac   4140
cccgtagaaa agatcaaagg atcttcttga gatcctttt ttctgcgcgt aatctgctgc   4200
ttgcaaacaa aaaaccacc gctaccagcg gtggtttgtt tgccggatca agagctacca   4260
actctttttc cgaaggtaac tggcttcagc agagcgcaga taccaaatac tgttcttcta   4320
gtgtagccgt agttaggcca ccacttcaag aactctgtag caccgcctac atacctcgct   4380
ctgctaatcc tgttaccagt ggctgctgcc agtggcgata gtcgtgtct taccgggttg   4440 gactcaagac gatagttacc ggataaggcg cagcggtcgg gctgaacggg gggttcgtgc   4500
acacagccca gcttggagcg aacgacctac accgaactga atacctaca gcgtgagcta   4560 tgagaaagcg ccacgcttcc cgaagggaga aaggcggaca ggtatccggt aagcggcagg   4620
gtcggaacag gagagcgcac gagggagctt ccaggggaa acgcctggta tctttatagt   4680
cctgtcgggt ttcgccacct ctgacttgag cgtcgatttt tgtgatgctc gtcagggggg   4740
cggagcctat ggaaaaacgc cagcaacgcg gcctttttac ggttcctggc cttttgctgg   4800
ccttttgctc acatgttctt tcctgcgtta tcccctgatt ctgtggataa ccgtattacc   4860
gcctttgagt gagctgatac cgctcgccgc agccgaacga ccgagcgcag cgagtcagtg   4920
agcgaggaag cggaag                                                   4936

<210> SEQ ID NO 21
<211> LENGTH: 35
<212> TYPE: DNA
<213> ORGANISM: Artificial Sequence
<220> FEATURE:
<223> OTHER INFORMATION: Primer Y1192

<400> SEQUENCE: 21
tggcacgctc aaccccacgg ttcgcttttc tcttt                               35

<210> SEQ ID NO 22
<211> LENGTH: 35
<212> TYPE: DNA
<213> ORGANISM: Artificial Sequence
<220> FEATURE:
<223> OTHER INFORMATION: Primer Y1193

<400> SEQUENCE: 22
aaagagaaaa gcgaaccgtg gggttgagcg tgcca                               35
```

<210> SEQ ID NO 23
<211> LENGTH: 4935
<212> TYPE: DNA
<213> ORGANISM: Artificial Sequence
<220> FEATURE:
<223> OTHER INFORMATION: Plasmid pT-DGAT2LPro-P

<400> SEQUENCE: 23

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctca     240
gaattaaccc tcactaaagg actagtcct gcaggtttaa acgaattcgc cttccaatc      300
gattgttgtg aaaattagca cggttatatt agcccgtaat aaatgccgt ctccatcttc     360
atatggccat caccccgcaa atagccggcc aatcaggcgt atgtcacctg ttgctcacac     420
gcatgtcctc ggaccgttgt attgtgcaag tagggggtacc tccccgatcc atcctcgacc    480
agtggcacgc tcaaccccat ggttcgcttt tctcttttcg tctatcctga actgagttta    540
aaccacgcca actgatatcc ccttacgtta cccccctcatc acctggtgag gcgaaactgt    600
aaggtgaaag ctaaaaatga catctcagct gcacgaagga ccggggctta aagacgggc     660
tggtgcttgt gatttaaaac tggacaaatc tcagcttgct tgaaattttg gtctccaact    720
gtttccgagc gaatcgcaca caaaccgggc ttctctctgc agaccacgcc cccgaaactc    780
tttctcccac caccaccaac actcccttttc cattcccaca ccgttcctct ctcgtgcgtc    840
atccttgcgc aatcatcttc gtctgcgaca tattgtacga catacagtac cacggaacgt    900
ttcagaccgt cgacgtgaac acatcttagg aacagcaacc tgagctacag aaatctatct    960
ataggcggat aaaaaaacgc acccactgct cgtcctcctt gctcctcgaa accgactcct   1020
ctacacacgt caaatccgag gttgaaatct tccccacatt tggcagccaa accagcacat   1080
cccagcaacc tcgcacagcg ccgaaatcga cctgtcgact tggccacaaa aaaagcacc   1140
ggctctgcaa cagttctcac gaccaattac gtacaagtac gaaatcgttc gtggaccgtg   1200
actgataagc tcccactttt tcttctaaca acaggcaaca gacaagtcac acaaaacaaa   1260
agccatggaa agtaagggcg aattcgcggc cgctaaattc aattcgccct atagtgagtc   1320
gtattacaat tcactggccg tcgttttaca acgtcgtgac tgggaaaacc ctggcgttac   1380
ccaacttaat cgccttgcag cacatccccc tttcgccagc tggcgtaata gcgaagaggc   1440
ccgcaccgat cgcccttccc aacagttgcg cagcctatac gtacggcagt taaggttta   1500
cacctataaa agagagagcc gttatcgtct gtttgtggat gtacagagtg atattattga   1560
cacgccgggg cgacggatgg tgatccccct ggccagtgca cgtctgctgt cagataaagt   1620
ctcccgtgaa ctttacccgg tggtgcatat cggggatgaa agctggcgca tgatgaccac   1680
cgatatggcc agtgtgccgg tctccgttat cggggaagaa gtggctgatc tcagccaccg   1740
cgaaaatgac atcaaaaacg ccattaacct gatgttctgg ggaatataaa tgtcaggcat   1800
gagattatca aaaaggatct tcacctagat ccttttcacg tagaaagcca gtccgcagaa   1860
acggtgctga ccccggatga atgtcagcta ctgggctatc tggacaaggg aaaacgcaag   1920
cgcaaagaga aagcaggtag cttgcagtgg gcttacatgg cgatagctag actgggcggt   1980
tttatggaca gcaagcgaac cggaattgcc agctggggcg ccctctggta aggttgggaa   2040
gccctgcaaa gtaaactgga tggctttctt gccgccaagg atctgatggc gcaggggatc   2100
```

-continued

```
aagctctgat caagagacag gatgaggatc gtttcgcatg attgaacaag atggattgca    2160
cgcaggttct ccggccgctt gggtggagag gctattcggc tatgactggg cacaacagac    2220
aatcggctgc tctgatgccg ccgtgttccg gctgtcagcg caggggcgcc cggttctttt    2280
tgtcaagacc gacctgtccg gtgccctgaa tgaactgcaa gacgaggcag cgcggctatc    2340
gtggctggcc acgacgggcg ttccttgcgc agctgtgctc gacgttgtca ctgaagcggg    2400
aagggactgg ctgctattgg gcgaagtgcc ggggcaggat ctcctgtcat ctcaccttgc    2460
tcctgccgag aaagtatcca tcatggctga tgcaatgcgg cggctgcata cgcttgatcc    2520
ggctacctgc ccattcgacc accaagcgaa acatcgcatc gagcgagcac gtactcggat    2580
ggaagccggt cttgtcgatc aggatgatct ggacgaagag catcaggggc tcgcgccagc    2640
cgaactgttc gccaggctca aggcgagcat gcccgacggc gaggatctcg tcgtgaccca    2700
tggcgatgcc tgcttgccga atatcatggt ggaaaatggc cgcttttctg gattcatcga    2760
ctgtggccgg ctgggtgtgg cggaccgcta tcaggacata gcgttggcta cccgtgatat    2820
tgctgaagag cttggcggcg aatgggctga ccgcttcctc gtgctttacg gtatcgccgc    2880
tcccgattcg cagcgcatcg ccttctatcg ccttcttgac gagttcttct gaattattaa    2940
cgcttacaat ttcctgatgc ggtatttcct ccttacgcat ctgtgcggta tttcacaccg    3000
catcaggtgg cacttttcgg ggaaatgtgc gcggaacccc tatttgttta ttttttctaaa   3060 tacattcaaa tatgtatccg ctcatgagat tatcaaaaag gatcttcacc tagatccttt    3120
taaattaaaa atgaagtttt aaatcaatct aaagtatata tgagtaaact tggtctgaca    3180
gttaccaatg cttaatcagt gaggcaccta tctcagcgat ctgtctattt cgttcatcca    3240
tagttgcctg actccccgtc gtgtagataa ctacgatacg ggagggctta ccatctggcc    3300
ccagtgctgc aatgataccg cgagacccac gctcaccggc tccagattta tcagcaataa    3360
accagccagc cggaagggcc gagcgcagaa gtggtcctgc aactttatcc gcctccatcc    3420
agtctattaa ttgttgccgg gaagctagag taagtagttc gccagttaat agtttgcgca    3480
acgttgttgc cattgctaca ggcatcgtgg tgtcacgctc gtcgtttggt atggcttcat    3540
tcagctccgg ttcccaacga tcaaggcgag ttacatgatc ccccatgttg tgcaaaaaag    3600
cggttagctc cttcggtcct ccgatcgttg tcagaagtaa gttggccgca gtgttatcac    3660
tcatggttat ggcagcactg cataattctc ttactgtcat gccatccgta agatgctttt    3720
ctgtgactgg tgagtactca accaagtcat tctgagaata gtgtatgcgg cgaccgagtt    3780
gctcttgccc ggcgtcaata cgggataata ccgcgccaca tagcagaact ttaaaagtgc    3840
tcatcattgg aaaacgttct tcggggcgaa aactctcaag gatcttaccg ctgttgagat    3900
ccagttcgat gtaacccact cgtgcaccca actgatcttc agcatctttt actttcacca    3960
gcgtttctgg gtgagcaaaa acaggaaggc aaaatgccgc aaaaaaggga ataagggcga    4020
cacgaaaatg ttgaatactc atactcttcc ttttttcaata ttattgaagc atttatcagg   4080
gttattgtct catgaccaaa atcccttaac gtgagttttc gttccactga gcgtcagacc    4140
ccgtagaaaa gatcaaagga tcttcttgag atcctttttt tctgcgcgta atctgctgct    4200
tgcaaacaaa aaaaccaccg ctaccagcgg tggtttgttt gccggatcaa gagctaccaa    4260 ctcttttttcc gaaggtaact ggcttcagca gagcgcagat accaaatact gttcttctag    4320
tgtagccgta gttaggccac cacttcaaga actctgtagc accgcctaca tacctcgctc    4380
tgctaatcct gttaccagtg gctgctgcca gtggcgataa gtcgtgtctt accgggttgg    4440
```

| | |
|---|---|
| actcaagacg atagttaccg ataaggcgc agcggtcggg ctgaacgggg ggttcgtgca | 4500 |
| cacagcccag cttggagcga acgacctaca ccgaactgag atacctacag cgtgagctat | 4560 |
| gagaaagcgc cacgcttccc gaagggagaa aggcggacag gtatccggta agcggcaggg | 4620 |
| tcggaacagg agagcgcacg agggagcttc caggggggaaa cgcctggtat ctttatagtc | 4680 |
| ctgtcgggtt tcgccacctc tgacttgagc gtcgattttt gtgatgctcg tcaggggggc | 4740 |
| ggagcctatg gaaaaacgcc agcaacgcgg ccttttttacg gttcctggcc ttttgctggc | 4800 |
| cttttgctca catgttcttt cctgcgttat cccctgattc tgtggataac cgtattaccg | 4860 |
| cctttgagtg agctgatacc gctcgccgca gccgaacgac cgagcgcagc gagtcagtga | 4920 |
| gcgaggaagc ggaag | 4935 |

<210> SEQ ID NO 24
<211> LENGTH: 39
<212> TYPE: DNA
<213> ORGANISM: Artificial Sequence
<220> FEATURE:
<223> OTHER INFORMATION: Primer Y1220

<400> SEQUENCE: 24

| | |
|---|---|
| ctatcctgaa ctgagtttaa accacgccaa ctgatatcc | 39 |

<210> SEQ ID NO 25
<211> LENGTH: 39
<212> TYPE: DNA
<213> ORGANISM: Artificial Sequence
<220> FEATURE:
<223> OTHER INFORMATION: Primer Y1221

<400> SEQUENCE: 25

| | |
|---|---|
| ggatatcagt tggcgtggtt taaactcagt tcaggatag | 39 |

<210> SEQ ID NO 26
<211> LENGTH: 965
<212> TYPE: DNA
<213> ORGANISM: Yarrowia lipolytica

<400> SEQUENCE: 26

| | |
|---|---|
| cgattgttgt gaaaattagc acggttatat tagcccgtaa taaatgcccg tctccatctt | 60 |
| catatggcca tcaccccgca aatagccggc caatcaggcg tatgtcacct gttgctcaca | 120 |
| cgcatgtcct cggaccgttg tattgtgcaa gtaggggtac ctccccgatc catcctcgac | 180 |
| cagtggcacg ctcaaccca tggttcgctt ttctcttttc gtctatcctg aactgagttt | 240 |
| aaaccacgcc aactgatatc cccttacgtt accccctcat cacctggtga ggcgaaactg | 300 |
| taaggtgaaa gctaaaaatg acatctcagc tgcacgaagg accggggctt aaaagacggg | 360 |
| ctggtgcttg tgatttaaaa ctggacaaat ctcagcttgc ttgaaatttt ggtctccaac | 420 |
| tgtttccgag cgaatcgcac acaaaccggg cttctctctg cagaccacgc ccccgaaact | 480 |
| cttttctccca ccaccaccaa cactcccttt ccattcccac accgttcctc tctcgtgcgt | 540 |
| catccttgcg caatcatctt cgtctgcgac atattgtacg acatacagta ccacggaacg | 600 |
| tttcagaccg tcgacgtgaa cacatcttag gaacagcaac ctgagctaca gaaatctatc | 660 |
| tataggcgga taaaaaaacg cacccactgc tcgtcctcct tgctcctcga aaccgactcc | 720 |
| tctacacacg tcaaatccga ggttgaaatc ttccccacat ttggcagcca aaccagcaca | 780 |
| tcccagcaac ctcgcacagc gccgaaatcg acctgtcgac ttggcacaa aaaaagcac | 840 |
| cggctctgca acagttctca cgaccaatta cgtacaagta cgaaatcgtt cgtggaccgt | 900 |

```
gactgataag ctcccacttt ttcttctaac aacaggcaac agacaagtca cacaaaacaa    960
aagcc                                                                965

<210> SEQ ID NO 27
<211> LENGTH: 38
<212> TYPE: DNA
<213> ORGANISM: Artificial Sequence
<220> FEATURE:
<223> OTHER INFORMATION: Primer Y2160

<400> SEQUENCE: 27
cgtgaacaca tcttaggttt aaacagcaac ctgagcta                             38

<210> SEQ ID NO 28
<211> LENGTH: 38
<212> TYPE: DNA
<213> ORGANISM: Artificial Sequence
<220> FEATURE:
<223> OTHER INFORMATION: Primer Y2161

<400> SEQUENCE: 28
tagctcaggt tgctgtttaa acctaagatg tgttcacg                             38

<210> SEQ ID NO 29
<211> LENGTH: 9020
<212> TYPE: DNA
<213> ORGANISM: Artificial Sequence
<220> FEATURE:
<223> OTHER INFORMATION: Plasmid pDG2SGUS-P

<400> SEQUENCE: 29
catggcatgg atggtacgtc ctgtagaaac cccaacccgt gaaatcaaaa aactcgacgg     60
cctgtgggca ttcagtctgg atcgcgaaaa ctgtggaatt gatcagcgtt ggtgggaaag    120
cgcgttacaa gaaagccggg caattgctgt gccaggcagt tttaacgatc agttcgccga    180
tgcagatatt cgtaattatg cgggcaacgt ctggtatcag cgcgaagtct ttataccgaa    240
aggttgggca ggccagcgta tcgtgctgcg tttcgatgcg gtcactcatt acggcaaagt    300
gtgggtcaat aatcaggaag tgatggagca tcagggcggc tatacgccat ttgaagccga    360
tgtcacgccg tatgttattg ccgggaaaag tgtacgtatc accgtttgtg tgaacaacga    420
actgaactgg cagactatcc cgccgggaat ggtgattacc gacgaaaacg gcaagaaaaa    480
gcagtcttac ttccatgatt tctttaacta tgccgggatc catcgcagcg taatgctcta    540
cacccacgcc aacacctggg tggacgatat caccgtggtg acgcatgtcg cgcaagactg    600
taaccacgcg tctgttgact ggcaggtggt ggccaatggt gatgtcagcg ttgaactgcg    660
tgatgcggat caacaggtgg ttgcaactgg acaaggcact agcgggactt tgcaagtggt    720
gaatccgcac ctctggcaac cgggtgaagg ttatctctat gaactgtgcg tcacagccaa    780
aagccagaca gagtgtgata tctacccgct tcgcgtcggc atccggtcag tggcagtgaa    840
gggcgaacag ttcctgatta accacaaacc gttctacttt actggctttg gtcgtcatga    900
agatgcggac ttacgtggca aaggattcga taacgtgctg atggtgcacg accacgcatt    960
aatggactgg attggggcca actcctaccg tacctcgcat taccctacg ctgaagagat    1020 gctcgactgg gcagatgaac atggcatcgt ggtgattgat gaaactgctg ctgtcggctt    1080
taacctctct ttaggcattg gtttcgaagc gggcaacaag ccgaaagaac tgtacagcga    1140
agaggcagtc aacgggaaa ctcagcaagc gcacttacag gcgattaaag agctgatagc    1200
```

-continued

```
gcgtgacaaa aaccacccaa gcgtggtgat gtggagtatt gccaacgaac cggatacccg      1260
tccgcaagtg cacgggaata tttcgccact ggcggaagca acgcgtaaac tcgacccgac      1320
gcgtccgatc acctgcgtca atgtaatgtt ctgcgacgct cacaccgata ccatcagcga      1380
tctctttgat gtgctgtgcc tgaaccgtta ttacggatgg tatgtccaaa gcggcgattt      1440
ggaaacggca gagaaggtac tggaaaaaga acttctggcc tggcaggaga aactgcatca      1500
gccgattatc atcaccgaat acggcgtgga tacgttagcc gggctgcact caatgtacac      1560
cgacatgtgg agtgaagagt atcagtgtgc atggctggat atgtatcacc gcgtctttga      1620
tcgcgtcagc gccgtcgtcg gtgaacaggt atggaatttc gccgattttg cgacctcgca      1680
aggcatattg cgcgttggcg gtaacaagaa agggatcttc actcgcgacc gcaaaccgaa      1740
gtcggcggct tttctgctgc aaaaacgctg gactggcatg aacttcggtg aaaaaccgca      1800
gcagggaggc aaacaatgat taattaacta gagcggccgc caccgcggcc cgagattccg      1860
gcctcttcgg ccgccaagcg acccgggtgg acgtctagag gtacctagca attaacagat      1920
agtttgccgg tgataattct cttaacctcc cacactcctt tgacataacg atttatgtaa      1980
cgaaactgaa atttgaccag atattgtgtc cgcggtggag ctccagcttt tgttcccttt      2040
agtgagggtt aatttcgagc ttggcgtaat catggtcata gctgtttcct gtgtgaaatt      2100
gttatccgct cacaattcca cacaacatac gagccggaag cataaagtgt aaagcctggg      2160
gtgcctaatg agtgagctaa ctcacattaa ttgcgttgcg ctcactgccc gctttccagt      2220
cgggaaacct gtcgtgccag ctgcattaat gaatcggcca acgcgcgggg agaggcggtt      2280
tgcgtattgg gcgctcttcc gcttcctcgc tcactgactc gctgcgctcg tcgttcggc      2340 tgcggcgagc ggtatcagct cactcaaagg cggtaatacg ttatccaca gaatcagggg      2400 ataacgcagg aaagaacatg tgagcaaaag gccagcaaaa ggccaggaac cgtaaaaagg      2460
ccgcgttgct ggcgtttttc cataggctcc gcccccctga cgagcatcac aaaaatcgac      2520
gctcaagtca gaggtggcga aacccgacag gactataaag ataccaggcg tttccccctg      2580
gaagctccct cgtgcgctct cctgttccga ccctgccgct taccggatac ctgtccgcct      2640
ttctcccttc gggaagcgtg gcgctttctc atagctcacg ctgtaggtat ctcagttcgg      2700
tgtaggtcgt tcgctccaag ctgggctgtg tgcacgaacc ccccgttcag cccgaccgct      2760
gcgccttatc cggtaactat cgtcttgagt ccaacccggt aagacacgac ttatcgccac      2820
tggcagcagc cactggtaac aggattagca gagcgaggta tgtaggcggt gctacagagt      2880
tcttgaagtg gtggcctaac tacggctaca ctagaaggac agtatttggt atctgcgctc      2940
tgctgaagcc agttaccttc ggaaaaagag ttggtagctc ttgatccggc aaacaaacca      3000
ccgctggtag cggtggtttt tttgtttgca agcagcagat tacgcgcaga aaaaaaggat      3060
ctcaagaaga tcctttgatc ttttctacgg ggtctgacgc tcagtggaac gaaaactcac      3120
gttaagggat tttggtcatg agattatcaa aaaggatctt cacctagatc cttttaaatt      3180
aaaaatgaag ttttaaatca atctaaagta tatatgagta aacttggtct gacagttacc      3240
aatgcttaat cagtgaggca cctatctcag cgatctgtct atttcgttca tccatagttg      3300
cctgactccc cgtcgtgtag ataactacga tacgggaggg cttaccatct ggccccagtg      3360
ctgcaatgat accgcgagac ccacgctcac cggctccaga tttatcagca ataaaccagc      3420
cagccggaag ggccgagcgc agaagtggtc ctgcaacttt atccgcctcc atccagtcta      3480
ttaattgttg ccgggaagct agagtaagta gttcgccagt taatagtttg cgcaacgttg      3540
ttgccattgc tacaggcatc gtggtgtcac gctcgtcgtt tggtatggct tcattcagct      3600
```

```
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg gcgacacgga    4080
aatgttgaat actcatactc ttcctttttc aatattattg aagcatttat cagggttatt    4140
gtctcatgag cggatacata tttgaatgta tttagaaaaa taaacaaata ggggttccgc    4200
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt tccccgtcaa gctctaaatc    4380
gggggctccc tttagggttc cgatttagtg ctttacggca cctcgacccc aaaaaacttg    4440
attagggtga tggttcacgt agtgggccat cgccctgata cggttttt cgccctttga    4500 cgttggagtc cacgttcttt aatagtggac tcttgttcca aactgaaca cactcaacc    4560 ctatctcggt ctattctttt gatttataag gattttgcc gatttcggcc tattggttaa    4620
aaaatgagct gatttaacaa aaatttaacg cgaattttaa caaatatta acgcttacaa    4680 tttccattcg ccattcaggc tgcgcaactg ttgggaaggg cgatcggtgc gggcctcttc    4740
gctattacgc cagctggcga aaggggatg tgctgcaagg cgattaagtt gggtaacgcc    4800
agggttttcc cagtcacgac gttgtaaaac gacggccagt gaattgtaat acgactcact    4860 ataggcgaa ttgggtaccg gccccccct cgaggtcgat ggtgtcgata agcttgatat    4920
cgaattcatg tcacacaaac cgatcttcgc ctcaaggaaa cctaattcta catccgagag    4980
actgccgaga tccagtctac actgattaat tttcgggcca ataatttaaa aaaatcgtgt    5040
tatataatat tatatgtatt atatatatac atcatgatga tactgacagt catgtcccat    5100
tgctaaatag acagactcca tctgccgcct ccaactgatg ttctcaatat ttaaggggtc    5160
atctcgcatt gtttaataat aaacagactc catctaccgc ctccaaatga tgttctcaaa    5220
atatattgta tgaacttatt tttattactt agtattatta gacaacttac ttgctttatg    5280
aaaaacactt cctatttagg aaacaattta taatggcagt tcgttcattt aacaatttat    5340
gtagaataaa tgttataaat gcgtatggga atcttaaat atggatagca taatgatat    5400 ctgcattgcc taattcgaaa tcaacagcaa cgaaaaaaat cccttgtaca acataaatag    5460
tcatcgagaa atatcaacta tcaaagaaca gctattcaca cgttactatt gagattatta    5520
ttggacgaga atcacacact caactgtctt tctctcttct agaaatacag gtacaagtat    5580
gtactattct cattgttcat acttctagtc atttcatccc acatattcct tggatttctc    5640
tccaatgaat gacattctat cttgcaaatt caacaattat aataagatat accaaagtag    5700
cggtatagtg gcaatcaaaa agcttctctg gtgtgcttct cgtatttatt tttatttctaa    5760 tgatccatta aggtatata tttatttctt gttatataat cctttttgttt attacatggg    5820 ctggatacat aaaaggtattt tgatttaatt ttttgcttaa attcaatccc cctcgttca    5880 gtgtcaactg taatggtagg aaattaccat acttttgaag aagcaaaaaa aatgaaagaa    5940
```

```
aaaaaaaatc gtatttccag gttagacgtt ccgcagaatc tagaatgcgg tatgcggtac    6000
attgttcttc gaacgtaaaa gttgcgctcc ctgagatatt gtacatttt gcttttacaa    6060 gtacaagtac atcgtacaac tatgtactac tgttgatgca tccacaacag tttgttttgt    6120
ttttttttgt tttttttttt tctaatgatt cattaccgct atgtatacct acttgtactt    6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg agcctaaaa     6360 tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata taaccaat     6540 taaacaaat gaaagaaat acagttcttt gtatcatttg taacaattac cctgtacaaa     6600
ctaaggtatt gaaatcccac aatattccca aagtccaccc ctttccaaat tgtcatgcct    6660
acaactcata taccaagcac taacctacca aacaccacta aaaccccaca aaatatatct    6720
taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg ccctttttat agagtcttat    7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatgggt tgaccttctg cttgccgaga    7320
tcgggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctggggaat     7560 tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagataccctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga gtcgccgcc gagaagaaca atcttcttgg agtcagtctt ggtcttctta    8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
```

```
ctaaacctcc gaagattgtg actcaggtag tgcggtatcg gctagggacc caaaccttgt    8400
cgatgccgat agcgctatcg aacgtacccc agccggccgg gagtatgtcg gaggggacat    8460
acgagatcgt caagggtttg tggccaactg gtaaataaat gatgtcgacg tttaaacgaa    8520
ttcgccctat cgatttctcc caccaccacc aacactccct ttccattccc acaccgttcc    8580
tctctcgtgc gtcatccttg cgcaatcatc ttcgtctgcg acatattgta cgacatacag    8640
taccacggaa cgtttcagac cgtcgacgtg aacacatctt aggtttaaac agcaacctga    8700
gctacagaaa tctatctata ggcggataaa aaaacgcacc cactgctcgt cctccttgct    8760
cctcgaaacc gactcctcta cacacgtcaa atccgaggtt gaaatcttcc ccacatttgg    8820
cagccaaacc agcacatccc agcaacctcg cacagcgccg aaatcgacct gtcgacttgg    8880
ccacaaaaaa aagcaccggc tctgcaacag ttctcacgac caattacgta caagtacgaa    8940
atcgttcgtg gaccgtgact gataagctcc cactttttct tctaacaaca ggcaacagac    9000
aagtcacaca aaacaaaagc                                                9020

<210> SEQ ID NO 30
<211> LENGTH: 9019
<212> TYPE: DNA
<213> ORGANISM: Artificial Sequence
<220> FEATURE:
<223> OTHER INFORMATION: Plasmid pDG2SGUS-P3

<400> SEQUENCE: 30
catggcatgg atggtacgtc ctgtagaaac cccaacccgt gaaatcaaaa aactcgacgg      60
cctgtgggca ttcagtctgg atcgcgaaaa ctgtggaatt gatcagcgtt ggtgggaaag     120
cgcgttacaa gaaagccggg caattgctgt gccaggcagt tttaacgatc agttcgccga     180
tgcagatatt cgtaattatg cgggcaacgt ctggtatcag cgcgaagtct ttataccgaa     240
aggttgggca ggccagcgta tcgtgctgcg tttcgatgcg gtcactcatt acggcaaagt     300
gtgggtcaat aatcaggaag tgatggagca tcagggcggc tatacgccat ttgaagccga     360
tgtcacgccg tatgttattg ccgggaaaag tgtacgtatc accgtttgtg tgaacaacga     420
actgaactgg cagactatcc cgccgggaat ggtgattacc gacgaaaacg gcaagaaaaa     480
gcagtcttac ttccatgatt tctttaacta tgccgggatc catcgcagcg taatgctcta     540
caccacgccg aacaccctgg gtggacgtat caccgtggtg acgcatgtcg cgcaagactg     600
taaccacgcg tctgttgact ggcaggtggt ggccaatggt gatgtcagcg ttgaactgcg     660
tgatgcggat caacaggtgg ttgcaactgg acaaggcact agcgggactt tgcaagtggt     720
gaatccgcac ctctggcaac cgggtgaagg ttatctctat gaactgtgcg tcacagccaa     780
aagccagaca gagtgtgata tctacccgct tcgcgtcggc atccggtcag tggcagtgaa     840
gggcgaacag ttcctgatta accacaaacc gttctacttt actggctttg tcgtcatga      900
agatgcggac ttacgtggca aaggattcga taacgtgctg atggtgcacg accacgcatt     960
aatggactgg attggggcca actcctaccg tacctcgcat taccctttacg ctgaagagat    1020
gctcgactgg gcagatgaac atggcatcgt ggtgattgat gaaactgctg ctgtcggctt    1080
taacctctct ttaggcattg gtttcgaagc gggcaacaag ccgaaagaac tgtacagcga    1140
agaggcagtc aacggggaaa ctcagcaagc gcacttacag gcgattaaag agctgatagc    1200
gcgtgacaaa aaccacccaa gcgtggtgat gtggagtatt gccaacgaac cggataccgg    1260
tccgcaagtg cacgggaata tttcgccact ggcggaagca acgcgtaaac tcgacccgac    1320
```

```
gcgtccgatc acctgcgtca atgtaatgtt ctgcgacgct cacaccgata ccatcagcga    1380
tctctttgat gtgctgtgcc tgaaccgtta ttacggatgg tatgtccaaa gcggcgattt    1440
ggaaacggca gagaaggtac tggaaaaaga acttctggcc tggcaggaga aactgcatca    1500
gccgattatc atcaccgaat acggcgtgga tacgttagcc gggctgcact caatgtacac    1560
cgacatgtgg agtgaagagt atcagtgtgc atggctggat atgtatcacc gcgtctttga    1620
tcgcgtcagc gccgtcgtcg gtgaacaggt atggaatttc gccgattttg cgacctcgca    1680
aggcatattg cgcgttggcg gtaacaagaa agggatcttc actcgcgacc gcaaaccgaa    1740
gtcggcggct tttctgctgc aaaaacgctg gactggcatg aacttcggtg aaaaaccgca    1800
gcagggaggc aaacaatgat taattaacta gagcggccgc caccgcggcc cgagattccg    1860
gcctcttcgg ccgccaagcg acccgggtgg acgtctagag gtacctagca attaacagat    1920
agtttgccgg tgataattct cttaacctcc cacactcctt tgacataacg atttatgtaa    1980
cgaaactgaa atttgaccag atattgtgtc cgcggtggag ctccagcttt tgttcccttt    2040
agtgagggtt aatttcgagc ttggcgtaat catggtcata gctgtttcct gtgtgaaatt    2100
gttatccgct cacaattcca cacaacatac gagccggaag cataaagtgt aaagcctggg    2160
gtgcctaatg agtgagctaa ctcacattaa ttgcgttgcg ctcactgccc gctttccagt    2220
cgggaaacct gtcgtgccag ctgcattaat gaatcggcca acgcgcgggg agaggcggtt    2280
tgcgtattgg gcgctcttcc gcttcctcgc tcactgactc gctgcgctcg gtcgttcggc    2340
tgcggcgagc ggtatcagct cactcaaagg cggtaatacg ttatccaca gaatcagggg    2400
ataacgcagg aaagaacatg tgagcaaaag gccagcaaaa ggccaggaac cgtaaaaagg    2460
ccgcgttgct ggcgtttttc cataggctcc gcccccctga cgagcatcac aaaaatcgac    2520
gctcaagtca gaggtggcga aacccgacag gactataaag ataccaggcg tttccccctg    2580
gaagctccct cgtgcgctct cctgttccga ccctgccgct taccggatac ctgtccgcct    2640
ttctccctt gggaagcgtg gcgctttctc atagctcacg ctgtaggtat ctcagttcgg    2700
tgtaggtcgt tcgctccaag ctgggctgtg tgcacgaacc ccccgttcag cccgaccgct    2760
gcgccttatc cggtaactat cgtcttgagt ccaacccggt aagacacgac ttatcgccac    2820
tggcagcagc cactggtaac aggattagca gagcgaggta tgtaggcggt gctacagagt    2880
tcttgaagtg gtggcctaac tacggctaca ctagaaggac agtatttggt atctgcgctc    2940
tgctgaagcc agttaccttc ggaaaaagag ttggtagctc ttgatccggc aaacaaacca    3000
ccgctggtag cggtggtttt tttgtttgca agcagcagat tacgcgcaga aaaaaggat    3060
ctcaagaaga tcctttgatc ttttctacgg ggtctgacgc tcagtggaac gaaaactcac    3120
gttaagggat tttggtcatg agattatcaa aaaggatctt cacctagatc ctttaaatt    3180
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaaccagc    3420
cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatccccat gttgtgcaaa aaagcggtta    3660
gctccttcgg tcctccgatc gttgtcagaa gtaagttggc cgcagtgtta tcactcatgg    3720
```

```
ttatggcagc actgcataat tctcttactg tcatgccatc cgtaagatgc ttttctgtga   3780
ctggtgagta ctcaaccaag tcattctgag aatagtgtat gcggcgaccg agttgctctt   3840
gcccggcgtc aatacgggat aataccgcgc cacatagcag aactttaaaa gtgctcatca   3900
ttggaaaacg ttcttcgggg cgaaaactct caaggatctt accgctgttg agatccagtt   3960
cgatgtaacc cactcgtgca cccaactgat cttcagcatc ttttactttc accagcgttt   4020
ctgggtgagc aaaaacagga aggcaaaatg ccgcaaaaaa gggaataagg gcgacacgga   4080
aatgttgaat actcatactc ttcctttttc aatattattg aagcatttat cagggttatt   4140
gtctcatgag cggatacata tttgaatgta tttagaaaaa taaacaaata ggggttccgc   4200
gcacatttcc ccgaaaagtg ccacctgacg cgccctgtag cggcgcatta agcgcggcgg   4260
gtgtggtggt tacgcgcagc gtgaccgcta cacttgccag cgccctagcg cccgctcctt   4320
tcgctttctt cccttccttt ctcgccacgt tcgccggctt tccccgtcaa gctctaaatc   4380
gggggctccc tttagggttc cgatttagtg ctttacggca cctcgacccc aaaaaacttg   4440
attagggtga tggttcacgt agtgggccat cgccctgata cggtttttt cgcccttttga  4500
cgttggagtc cacgttcttt aatagtggac tcttgttcca aactgaaaca acactcaacc   4560
ctatctcggt ctattctttt gatttataag ggattttgcc gatttcggcc tattggttaa   4620
aaaatgagct gatttaacaa aaatttaacg cgaattttaa caaaatatta cgcttacaa    4680
tttccattcg ccattcaggc tgcgcaactg ttgggaaggg cgatcggtgc gggcctcttc   4740
gctattacgc cagctggcga aaggggggatg tgctgcaagg cgattaagtt gggtaacgcc   4800
agggttttcc cagtcacgac gttgtaaaac gacggccagt gaattgtaat acgactcact   4860
atagggcgaa ttgggtaccg ggccccccct cgaggtcgat ggtgtcgata agcttgatat   4920
cgaattcatg tcacacaaac cgatcttcgc ctcaaggaaa cctaattcta catccgagag   4980
actgccgaga tccagtctac actgattaat tttcgggcca ataatttaaa aaaatcgtgt   5040
tatataatat tatatgtatt atatatatac atcatgatga tactgacagt catgtcccat   5100
tgctaaatag acagactcca tctgccgcct ccaactgatg ttctcaatat ttaagggggtc  5160
atctcgcatt gtttaataat aaacagactc catctaccgc ctccaaatga tgttctcaaa   5220
atatattgta tgaacttatt tttattactt agtattatta gacaacttac ttgctttatg   5280
aaaaacactt cctatttagg aaacaattta taatggcagt tcgttcattt aacaatttat   5340
gtagaataaa tgttataaat gcgtatggga atcttaaat atggatagca taatgatat    5400
ctgcattgcc taattcgaaa tcaacagcaa cgaaaaaaat cccttgtaca acataaaatag  5460
tcatcgagaa atatcaacta tcaaagaaca gctattcaca cgttactatt gagattatta   5520
ttggacgaga atcacacact caactgtctt tctctcttct agaaatacag gtacaagtat   5580
gtactattct cattgttcat acttctagtc atttcatccc acatattcct tggatttctc   5640
tccaatgaat gacattctat cttgcaaatt caacaattat aataagatat accaaagtag   5700
cggtatagtg gcaatcaaaa agcttctctg gtgtgcttct cgtatttatt tttattctaa   5760
tgatccatta aaggtatata tttatttctt gttatataat cctttttgttt attacatggg  5820
ctggatacat aaaggtattt tgatttaatt ttttgcttaa attcaatccc ccctcgttca   5880
gtgtcaactg taatggtagg aaattaccat acttttgaag aagcaaaaaa aatgaaagaa   5940
aaaaaaaatc gtatttccag gttagacgtt ccgcagaatc tagaatgcgg tatgcggtac   6000
attgttcttc gaacgtaaaa gttgcgctcc ctgagatatt gtacattttt gcttttacaa   6060
```

```
gtacaagtac atcgtacaac tatgtactac tgttgatgca tccacaacag tttgttttgt    6120 tttttttgt tttttttttt tctaatgatt cattaccgct atgtatacct acttgtactt      6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg agcctaaaa     6360 tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540 taaacaaat gaaagaaat acagttcttt gtatcatttg taacaattac cctgtacaaa      6600
ctaaggtatt gaaatcccac aatattccca aagtccaccc cttttccaaat tgtcatgcct   6660 acaactcata taccaagcac taacctacca aacaccacta aaaccccaca aaatatatct    6720
taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac   6900
gtaccactgt cctccactac aaacacaccc aatctgcttc ttctagtcaa ggttgctaca    6960
ccggtaaatt ataaatcatc atttcattag cagggcaggg ccctttttat agagtcttat    7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg   7200
acggactcct tgacggcagc ctcaacagcg tcaccggcgg gcttcatgtt aagagagaac    7260
ttgagcatca tggcggcaga cagaatggtg gcaatggggt tgaccttctg cttgccgaga    7320 tcggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctgggggaat    7560
tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga gtcgccgcc gagaagaaca atcttcttgg agtcagtctt ggtcttctta      8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
ctaaacctcc gaagattgtg actcaggtag tgcggtatcg gctagggacc caaaccttgt    8400
cgatgccgat agcgctatcg aacgtacccc agccggccgg gagtatgtcg gagggacat     8460
```

```
acgagatcgt caagggtttg tggccaactg gtaaataaat gatgtcgacg tttaaacgaa    8520
ttcgccctat cgatttctcc caccaccacc aacactccct ttccattccc acaccgttcc    8580
tctctcgtgc gtcatccttg cgcaatcatc ttcgtctgcg acatattgta cgacatacag    8640
taccacggaa cgtttcagac cgtcgacgtg aacacatctt aggaacagca acctgagcta    8700
cagaaatcta tctataggcg gataaaaaaa cgcacccact gctcgtcctc cttgctcctc    8760
gtttaaaccg actcctctac acacgtcaaa tccgaggttg aaatcttccc cacatttggc    8820
agccaaacca gcacatccca gcaacctcgc acagcgccga aatcgacctg tcgacttggc    8880
cacaaaaaaa agcaccggct ctgcaacagt tctcacgacc aattacgtac aagtacgaaa    8940
tcgttcgtgg accgtgactg ataagctccc acttttcttc ctaacaacag gcaacagaca    9000
agtcacacaa aacaaaagc                                                 9019
```

<210> SEQ ID NO 31
<211> LENGTH: 38
<212> TYPE: DNA
<213> ORGANISM: Artificial Sequence
<220> FEATURE:
<223> OTHER INFORMATION: Primer Y2164

<400> SEQUENCE: 31

```
gtcctccttg ctcctcgttt aaaccgactc ctctacac                            38
```

<210> SEQ ID NO 32
<211> LENGTH: 38
<212> TYPE: DNA
<213> ORGANISM: Artificial Sequence
<220> FEATURE:
<223> OTHER INFORMATION: Primer Y2165

<400> SEQUENCE: 32

```
gtgtagagga gtcggtttaa acgaggagca aggaggac                            38
```

<210> SEQ ID NO 33
<211> LENGTH: 51
<212> TYPE: DNA
<213> ORGANISM: Yarrowia lipolytica

<400> SEQUENCE: 33

```
caaaaaaaag caccggctct gcaacagttc tcacgaccaa ttacgtacaa g             51
```

<210> SEQ ID NO 34
<211> LENGTH: 138
<212> TYPE: DNA
<213> ORGANISM: Yarrowia lipolytica

<400> SEQUENCE: 34

```
caaaaaaaag caccggctct gcaacagttc tcacgaccaa ttacgtacaa gtacgaaatc    60
gttcgtggac cgtgactgat aagctcccac ttttcttct aacaacaggc aacagacaag   120
tcacacaaaa caaaagcc                                                 138
```

<210> SEQ ID NO 35
<211> LENGTH: 9348
<212> TYPE: DNA
<213> ORGANISM: Artificial Sequence
<220> FEATURE:
<223> OTHER INFORMATION: Plasmid pDMW212

<400> SEQUENCE: 35

```
ggtggagctc cagcttttgt tcccttagt gagggttaat ttcgagcttg gcgtaatcat    60
ggtcatagct gtttcctgtg tgaaattgtt atccgctcac aattccacac aacatacgag   120
ccggaagcat aaagtgtaaa gcctggggtg cctaatgagt gagctaactc acattaattg   180
cgttgcgctc actgcccgct ttccagtcgg gaaacctgtc gtgccagctg cattaatgaa   240
tcggccaacg cgcggggaga ggcggtttgc gtattgggcg ctcttccgct tcctcgctca   300
ctgactcgct gcgctcggtc gttcggctgc ggcgagcggt atcagctcac tcaaaggcgg   360
taatacggtt atccacagaa tcaggggata acgcaggaaa gaacatgtga gcaaaaggcc   420
agcaaaaggc caggaaccgt aaaaaggccg cgttgctggc gtttttccat aggctccgcc   480
cccctgacga gcatcacaaa aatcgacgct caagtcagag gtggcgaaac ccgacaggac   540
tataaagata ccaggcgttt ccccctggaa gctccctcgt gcgctctcct gttccgaccc   600
tgccgcttac cggatacctg tccgcctttc tcccttcggg aagcgtggcg ctttctcata   660
gctcacgctg taggtatctc agttcggtgt aggtcgttcg ctccaagctg ggctgtgtgc   720
acgaaccccc cgttcagccc gaccgctgcg ccttatccgg taactatcgt cttgagtcca   780
acccggtaag acacgactta tcgccactgg cagcagccac tggtaacagg attagcagag   840
cgaggtatgt aggcggtgct acagagttct tgaagtggtg gcctaactac ggctacacta   900
gaaggacagt atttggtatc tgcgctctgc tgaagccagt taccttcgga aaaagagttg   960
gtagctcttg atccggcaaa caaaccaccg ctggtagcgg tggtttttt gtttgcaagc   1020
agcagattac gcgcagaaaa aaaggatctc aagaagatcc tttgatcttt tctacggggt   1080
ctgacgctca gtggaacgaa aactcacgtt aagggatttt ggtcatgaga ttatcaaaaa   1140
ggatcttcac ctagatcctt ttaaattaaa aatgaagttt taaatcaatc taaagtatat   1200
atgagtaaac ttggtctgac agttaccaat gcttaatcag tgaggcacct atctcagcga   1260
tctgtctatt tcgttcatcc atagttgcct gactccccgt cgtgtagata actacgatac   1320
gggagggctt accatctggc cccagtgctg caatgatacc gcgagaccca cgctcaccgg   1380
ctccagattt atcagcaata aaccagccag ccggaagggc cgagcgcaga agtggtcctg   1440
caactttatc cgcctccatc cagtctatta attgttgccg ggaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc cttttttcaat  2100
attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg ggctcccttt agggttccga tttagtgctt   2400
```

```
tacggcacct cgaccccaaa aaacttgatt agggtgatgg ttcacgtagt gggccatcgc   2460
cctgatagac ggttttttcgc cctttgacgt tggagtccac gttctttaat agtggactct  2520
tgttccaaac tggaacaaca ctcaaccta tctcggtcta ttcttttgat ttataaggga    2580
ttttgccgat ttcggcctat tggttaaaaa atgagctgat ttaacaaaaa tttaacgcga   2640
attttaacaa atattaacg cttacaattt ccattcgcca ttcaggctgc gcaactgttg    2700
ggaagggcga tcggtgcggg cctcttcgct attacgccag ctggcgaaag ggggatgtgc   2760
tgcaaggcga ttaagttggg taacgccagg gttttcccag tcacgacgtt gtaaaacgac   2820
ggccagtgaa ttgtaatacg actcactata gggcgaattg ggtaccgggc cccccctcga   2880
ggtcgatggt gtcgataagc ttgatatcga attcatgtca cacaaaccga tcttcgcctc   2940
aaggaaacct aattctacat ccgagagact gccgagatcc agtctacact gattaatttt   3000
cgggccaata atttaaaaaa atcgtgttat ataatattat atgtattata tatatacatc   3060
atgatgatac tgacagtcat gtcccattgc taaatagaca gactccatct gccgcctcca   3120
actgatgttc tcaatattta aggggtcatc tcgcattgtt taataataaa cagactccat   3180
ctaccgcctc caaatgatgt tctcaaaata tattgtatga acttattttt attacttagt   3240
attattagac aacttacttg ctttatgaaa acacttcct atttaggaaa caatttataa     3300
tggcagttcg ttcatttaac aatttatgta gaataaatgt tataaatgcg tatgggaaat    3360
cttaaatatg gatagcataa atgatatctg cattgcctaa ttcgaaatca acagcaacga   3420
aaaaaatccc ttgtacaaca taaatagtca tcgagaaata tcaactatca aagaacagct   3480
attcacacgt tactattgag attattattg gacgagaatc acacactcaa ctgtctttct   3540
ctcttctaga aatacaggta caagtatgta ctattctcat tgttcatact tctagtcatt    3600
tcatcccaca tattccttgg atttctctcc aatgaatgac attctatctt gcaaattcaa   3660
caattataat aagatatacc aaagtagcgg tatagtggca atcaaaaagc ttctctggtg   3720
tgcttctcgt atttattttt attctaatga tccattaaag gtatatattt atttcttgtt    3780
atataatcct tttgtttatt acatgggctg gatacataaa ggtattttga tttaatttt    3840 tgcttaaatt caatcccccc tcgttcagtg tcaactgtaa tggtaggaaa ttaccatact   3900
tttgaagaag caaaaaaaat gaaagaaaaa aaaaatcgta tttccaggtt agacgttccg   3960
cagaatctag aatgcggtat gcggtacatt gttcttcgaa cgtaaaagtt gcgctccctg   4020
agatattgta cattttttgct tttacaagta caagtacatc gtacaactat gtactactgt   4080
tgatgcatcc acaacagttt gttttgtttt ttttgtttt tttttttct aatgattcat     4140 taccgctatg tatacctact tgtacttgta gtaagccggg ttattggcgt tcaattaatc   4200
atagacttat gaatctgcac ggtgtgcgct gcgagttact tttagcttat gcatgctact    4260
tgggtgtaat attgggatct gttcggaaat caacggatgc tcaaccgatt tcgacagtaa   4320
taatttgaat cgaatcggag cctaaaatga acccgagtat atctcataaa attctcggtg   4380
agaggtctgt gactgtcagt acaaggtgcc ttcattatgc cctcaacctt accatacctc   4440
actgaatgta gtgtacctct aaaaatgaaa tacagtgcca aaagccaagg cactgagctc   4500
gtctaacgga cttgatatac aaccaattaa aacaaatgaa agaaatacaa gttctttgta    4560
tcatttgtaa caattaccct gtacaaacta aggtattgaa atcccacaat attcccaaag   4620
tccacccctt tccaaattgt catgcctaca actcatatac caagcactaa cctaccaaac   4680
accactaaaa ccccacaaaa tatatcttac cgaatataca gtaacaagct accaccacac   4740
```

```
tcgttgggtg cagtcgccag cttaaagata tctatccaca tcagccacaa ctcccttcct    4800
ttaataaacc gactacaccc ttggctattg aggttatgag tgaatatact gtagacaaga    4860
cactttcaag aagactgttt ccaaaacgta ccactgtcct ccactacaaa cacacccaat    4920
ctgcttcttc tagtcaaggt tgctacaccg gtaaattata aatcatcatt tcattagcag    4980
ggcagggccc tttttataga gtcttataca ctagcggacc ctgccggtag accaacccgc    5040
aggcgcgtca gtttgctcct tccatcaatg cgtcgtagaa acgacttact ccttcttgag    5100
cagctccttg accttgttgg caacaagtct ccgacctcgg aggtggagga agagcctccg    5160
atatcggcgg tagtgatacc agcctcgacg gactccttga cggcagcctc aacagcgtca    5220
ccggcgggct tcatgttaag agagaacttg agcatcatgg cggcagacag aatggtggca    5280
atggggttga ccttctgctt gccgagatcg ggggcagatc cgtgacaggg ctcgtacaga    5340
ccgaacgcct cgttggtgtc gggcagagaa gccagagagg cggagggcag cagacccaga    5400
gaaccgggga tgacggaggc ctcgtcggag atgatatcgc caaacatgtt ggtggtgatg    5460
atgataccat tcatcttgga gggctgcttg atgaggatca tggcggccga gtcgatcagc    5520
tggtggttga gctcgagctg ggggaattcg tccttgagga ctcgagtgac agtctttcgc    5580
caaagtcgag aggaggccag cacgttggcc ttgtcaagag accacacggg aagagggggg    5640
ttgtgctgaa gggccaggaa ggcggccatt cgggcaattc gctcaacctc aggaacggag    5700
taggtctcgg tgtcggaagc gacgccagat ccgtcatcct cctttcgctc tccaaagtag    5760
atacctccga cgagctctcg gacaatgatg aagtcggtgc cctcaacgtt tcggatgggg    5820
gagagatcgg cgagcttggg cgacagcagc tggcagggtc gcaggttggc gtacaggttc    5880
aggtcctttc gcagcttgag gagaccctgc tcgggtcgca cgtcggttcg tccgtcggga    5940
gtggtccata cggtgttggc agcgcctccg acagcaccga gcataataga gtcagccttt    6000
cggcagatgt cgagagtagc gtcggtgatg ggctcgccct ccttctcaat ggcagctcct    6060
ccaatgagtc ggtcctcaaa cacaaactcg gtgccgagg cctcagcaac agacttgagc    6120
accttgacgg cctcggcaat cacctcgggg ccacagaagt cgccgccgag aagaacaatc    6180
ttcttggagt cagtcttggt cttcttagtt tcgggttcca ttgtggatgt gtgtggttgt    6240
atgtgtgatg tggtgtgtgg agtgaaaatc tgtggctggc aaacgctctt gtatatatac    6300
gcacttttgc ccgtgctatg tggaagacta aacctccgaa gattgtgact caggtagtgc    6360
ggtatcggct agggacccaa accttgtcga tgccgatagc gctatcgaac gtaccccagc    6420
cggccgggag tatgtcggag gggacatacg agatcgtcaa gggtttgtgg ccaactggta    6480
aataaatgat gtcgacgttt aaacagtgta cgcagtacta tagaggaaca attgccccgg    6540
agaagacggc caggccgcct agatgacaaa ttcaacaact cacagctgac ttcctgccat    6600
tgccactagg gggggccttt tttatatggc caagccaagc tctccacgtc ggttgggctg    6660
cacccaacaa taaatgggta gggttgcacc aacaagggat tgggatgggg ggtagaagat    6720
acgaggataa cggggctcaa tggcacaaat aagaacgaat actgccatta agactcgtga    6780
tccagcgact gacaccattg catcatcatc atctaagggc ctcaaaacta cctcggaact    6840
gctgcgctga tctggacacc acagaggttc cgagcacttt aggttgcacc aaatgtccca    6900
ccaggtgcag gcagaaaacg ctggaacagc gtgtacagtt tgtcttaaca aaaagtgagg    6960
gcgctgaggt cgagcagggt ggtgtgactt gttatagcct ttagagctgc gaaagcgcgt    7020
atggatttgg ctcatcaggc cagattgagg gtctgtggac acatgtcatg ttagtgtact    7080
tcaatcgccc cctggatata gccccgacaa taggccgtgg cctcattttt ttgccttccg    7140
```

```
cacatttcca ttgctcggta cccacacctt gcttctcctg cacttgccaa ccttaatact    7200
ggtttacatt gaccaacatc ttacaagcgg ggggcttgtc tagggtatat ataaacagtg    7260
gctctcccaa tcggttgcca gtctcttttt tcctttcttt ccccacagat tcgaaatcta    7320
aactacacat cacaccatgg catgatggt acgtcctgta gaaacccccaa cccgtgaaat    7380 caaaaaactc gacggcctgt gggcattcag tctggatcgc gaaaactgtg gaattgatca    7440
gcgttggtgg gaaagcgcgt tacaagaaag ccgggcaatt gctgtgccag gcagttttaa    7500
cgatcagttc gccgatgcag atattcgtaa ttatgcgggc aacgtctggt atcagcgcga    7560
agtctttata ccgaaaggtt gggcaggcca gcgtatcgtg ctgcgtttcg atgcggtcac    7620
tcattacggc aaagtgtggg tcaataatca ggaagtgatg gagcatcagg gcggctatac    7680
gccatttgaa gccgatgtca cgccgtatgt tattgccggg aaaagtgtac gtatcaccgt    7740
ttgtgtgaac aacgaactga actggcagac tatcccgccg gaatggtga ttaccgacga    7800 aaacggcaag aaaaagcagt cttacttcca tgatttcttt aactatgccg ggatccatcg    7860
cagcgtaatg ctctacacca cgccgaacac ctgggtggac gatatcaccg tggtgacgca    7920
tgtcgcgcaa gactgtaacc acgcgtctgt tgactggcag gtggtggcca atggtgatgt    7980
cagcgttgaa ctgcgtgatg cggatcaaca ggtggttgca actggacaag gcactagcgg    8040
gactttgcaa gtggtgaatc cgcacctctg gcaaccgggt gaaggttatc tctatgaact    8100
gtgcgtcaca gccaaaagcc agacagagtg tgatatctac ccgcttcgcg tcggcatccg    8160
gtcagtggca gtgaagggcg aacagttcct gattaaccac aaaccgttct actttactgg    8220 cttttggtcgt catgaagatg cggacttacg tggcaaagga ttcgataacg tgctgatggt    8280
gcacgaccac gcattaatgg actggattgg ggccaactcc taccgtacct cgcattaccc    8340
ttacgctgaa gagatgctcg actgggcaga tgaacatggc atcgtggtga ttgatgaaac    8400
tgctgctgtc ggctttaacc tctctttagg cattggtttc gaagcgggca acaagccgaa    8460
agaactgtac agcgaagagg cagtcaacgg ggaaactcag caagcgcact acaggcgat    8520 taaagagctg atagcgcgtg acaaaaaacca cccaagcgtg gtgatgtgga gtattgccaa    8580
cgaaccggat acccgtccgc aagtgcacgg gaatatttcg ccactggcgg aagcaacgcg    8640
taaactcgac ccgacgcgtc cgatcaccct cgtcaatgta atgttctgcg acgctcacac    8700
cgataccatc agcgatctct ttgatgtgct gtgcctgaac cgttattacg gatggtatgt    8760
ccaaagcggc gatttggaaa cggcagagaa ggtactggaa aaagaacttc tggcctggca    8820
ggagaaactg catcagccga ttatcatcac cgaatacggc gtggatacgt tagccgggct    8880
gcactcaatg tacaccgaca tgtggagtga agagtatcag tgtgcatggc tggatatgta    8940
tcaccgcgtc tttgatcgcg tcagcgccgt cgtcggtgaa caggtatgga atttcgccga    9000
ttttgcgacc tcgcaaggca tattgcgcgt tggcggtaac aagaaaggga tcttcactcg    9060
cgaccgcaaa ccgaagtcgg cggctttct gctgcaaaaa cgctggactg gcatgaactt    9120
cggtgaaaaa ccgcagcagg gaggcaaaca atgattaatt aactagagcg gccgccaccg    9180
cggcccgaga ttccggcctc ttcggccgcc aagcgaccg ggtggacgtc tagaggtacc    9240
tagcaattaa cagatagttt gccggtgata attctcttaa cctcccacac tcctttgaca    9300
taacgattta tgtaacgaaa ctgaaatttg accagatatt gtgtccgc                9348

<210> SEQ ID NO 36
<211> LENGTH: 2845
<212> TYPE: DNA
```

<213> ORGANISM: Yarrowia lipolytica
<220> FEATURE:
<221> NAME/KEY: misc_feature
<222> LOCATION: (1)..(2845)
<223> OTHER INFORMATION: YALI0E32769g locus
<220> FEATURE:
<221> NAME/KEY: misc_feature
<222> LOCATION: (1001)..(1003)
<223> OTHER INFORMATION: translation initiation codon 'ATG'; nucleotide
      'A' (designated as +1)

<400> SEQUENCE: 36

```
atgctgcggg cggatcctgg tgcatttttg cttgcgattg ttgtgaaaat tagcacggtt      60
atattagccc gtaataaatg cccgtctcca tcttcatatg ccatcaccc cgcaaatagc      120
cggccaatca ggcgtatgtc acctgttgct cacacgcatg tcctcggacc gttgtattgt     180
gcaagtaggg gtacctcccc gatccatcct cgaccagtgg cacgctcaac cccatggttc     240
gcttttctct tttcgtctat cctgaactga gttttttttcc acgccaactg atatcccctt    300
acgttacccc ctcatcacct ggtgaggcga aactgtaagg tgaaagctaa aaatgacatc     360
tcagctgcac gaaggaccgg ggcttaaaag acgggctggt gcttgtgatt taaaactgga     420
caaatctcag cttgcttgaa attttggtct ccaactgttt ccgagcgaat cgcacacaaa     480
ccgggcttct ctctgcagac cacgcccccg aaactctttc tccaccacc accaacactc     540
cctttccatt cccacaccgt tcctctctcg tgcgtcatcc ttgcgcaatc atcttcgtct    600
gcgacatatt gtacgacata cagtaccacg gaacgtttca gaccgtcgac gtgaacacat    660
cttaggaaca gcaacctgag ctacagaaat ctatctatag gcggataaaa aaacgcaccc    720
actgctcgtc ctccttgctc ctcgaaaccg actcctctac acacgtcaaa tccgaggttg    780
aaatcttccc cacatttggc agccaaacca gcacatccca gcaacctcgc acagcgccga    840
aatcgacctg tcgacttggc cacaaaaaaa agcaccggct ctgcaacagt tctcacgacc    900
aattacgtac aagtacgaaa tcgttcgtgg accgtgactg ataagctccc acttttctt    960
ctaacaacag gcaacagaca agtcacacaa acaaaagct atgactatcg actcacaata    1020
ctacaagtcg cgagacaaaa acgacacggc acccaaaatc gcgggaatcc gatatgcccc    1080
gctatcgaca ccattactca accgatgtga gaccttctct ctggtctggc acattttcag    1140
cattcccact ttcctcacaa ttttcatgct atgctgcgca attccactgc tctggccatt    1200
tgtgattgcg tatgtagtgt acgctgttaa agacgactcc ccgtccaacg gaggagtggt    1260
caagcgatac tcgcctattt caagaaactt cttcatctgg aagctcttg gccgctactt    1320
ccccataact ctgcacaaga cggtggatct ggagcccacg cacacatact accctctgga    1380
cgtccaggag tatcacctga ttgctgagag atactggccg cagaacaagt acctccgagc    1440
aatcatctcc accatcgagt actttctgcc cgccttcatg aaacggtctc tttctatcaa    1500
cgagcaggag cagcctgccg agcgagatcc tctcctgtct cccgtttctc ccagctctcc    1560
gggttctcaa cctgacaagt ggattaacca cgacagcaga tatagccgtg gagaatcatc    1620
tggctccaac ggccacgcct cgggctccga acttaacggc aacggcaaca atggcaccac    1680
taaccgacga cctttgtcgt ccgcctctgc tggctccact gcatctgatt ccacgcttct    1740
taacgggtcc ctcaactcct acgccaacca gatcattggc gaaaacgacc acagctgtc    1800
gcccacaaaa ctcaagccca ctggcagaaa atacatcttc ggctaccacc cccacggcat    1860
tatcggcatg ggagccttg gtggaattgc caccgaggga gctggatggt ccaagctctt    1920
tccgggcatc cctgtttctc ttatgactct caccaacaac ttccgagtgc ctctctacag    1980
```

-continued

```
agagtacctc atgagtctgg gagtcgcttc tgtctccaag aagtcctgca aggccctcct    2040
caagcgaaac cagtctatct gcattgtcgt tggtggagca caggaaagtc ttctggccag    2100
acccggtgtc atggacctgg tgctactcaa gcgaaagggt tttgttcgac ttggtatgga    2160
ggtcggaaat gtcgcccttg ttcccatcat ggcctttggt gagaacgacc tctatgacca    2220
ggttagcaac gacaagtcgt ccaagctgta ccgattccag cagtttgtca agaacttcct    2280
tggattcacc cttcctttga tgcatgcccg aggcgtcttc aactacgatg tcggtcttgt    2340
cccctacagg cgacccgtca acattgtggt tggttccccc attgacttgc cttatctccc    2400 acacccacc gacgaagaag tgtccgaata ccacgaccga tacatcgccg agctgcagcg     2460
aatctacaac gagcacaagg atgaatattt catcgattgg accgaggagg gcaaaggagc    2520
cccagagttc cgaatgattg agtaaggaaa actgcctggg ttaggcaaat agctaatgag    2580
tatttttttg atggcaacca aatgtagaaa gaaaaaaaaa aaaaagaaa aaaaaagag      2640 aatattatat ctatgtaatt ctattaaaag ctctgttgag tgagcggaat aaatactgtt    2700
gaagagggga ttgtgtagag atctgtttac tcaatggcaa actcatctgg gggagatcct    2760
tccactgtgg gaagctcctg gatagccttt gcatcgggtt caagaagacc attgtgaaca    2820
gccttgacac tgtcgacaat gacag                                         2845
```